United States Patent
Oakley et al.

(10) Patent No.: US 7,214,496 B2
(45) Date of Patent: May 8, 2007

(54) MODIFIED G-PROTEIN COUPLED RECEPTORS

(75) Inventors: Robert H. Oakley, Durham, NC (US); Lawrence S. Barak, Durham, NC (US); Stephane A. Laporte, Outremont (CA); Marc G. Caron, Hillsborough, NC (US)

(73) Assignee: Duke University, Durham, NC (US)

( * ) Notice: Subject to any disclaimer, the term of this patent is extended or adjusted under 35 U.S.C. 154(b) by 182 days.

(21) Appl. No.: 11/026,435

(22) Filed: Dec. 30, 2004

(65) Prior Publication Data
US 2005/0106623 A1    May 19, 2005

Related U.S. Application Data

(62) Division of application No. 09/993,844, filed on Nov. 5, 2001, now Pat. No. 7,018,812.

(60) Provisional application No. 60/260,363, filed on Jan. 8, 2001, provisional application No. 60/245,772, filed on Nov. 3, 2000.

(51) Int. Cl.
*G01N 33/53* (2006.01)
(52) U.S. Cl. .................... 435/7.1; 435/7.21; 435/69.7; 435/252.3; 436/501
(58) Field of Classification Search .................... None
See application file for complete search history.

(56) References Cited

U.S. PATENT DOCUMENTS

| | | | |
|---|---|---|---|
| 3,654,090 A | 4/1972 | Schuurs et al. |
| 3,850,752 A | 11/1974 | Schuurs et al. |
| 4,016,043 A | 4/1977 | Schuurs et al. |
| 4,341,761 A | 7/1982 | Ganfield et al. |
| RE31,006 E | 8/1982 | Schuurs et al. |
| 4,342,566 A | 8/1982 | Theofilopoulous et al. |
| 4,399,121 A | 8/1983 | Albarella et al. |
| 4,427,783 A | 1/1984 | Newman et al. |
| 4,444,887 A | 4/1984 | Hoffmann |
| 4,451,570 A | 5/1984 | Royston et al. |
| 4,466,917 A | 8/1984 | Nussenzweig et al. |
| 4,472,500 A | 9/1984 | Milstein et al. |
| 4,491,632 A | 1/1985 | Wands et al. |
| 4,493,890 A | 1/1985 | Morris |
| 4,816,397 A | 3/1989 | Boss et al. |
| 4,816,567 A | 3/1989 | Cabilly et al. |
| 4,981,784 A | 1/1991 | Evans et al. |
| 5,284,746 A | 2/1994 | Sledziewski et al. |
| 5,366,889 A | 11/1994 | MacDonald et al. |
| 5,468,854 A | 11/1995 | McCabe et al. |
| 5,482,835 A | 1/1996 | King et al. |
| 5,491,084 A | 2/1996 | Chalfie et al. |
| 5,532,157 A | 7/1996 | Fink |
| 5,576,436 A | 11/1996 | McCabe et al. |
| 5,625,048 A | 4/1997 | Tsien et al. |
| 5,777,079 A | 7/1998 | Tsien et al. |
| 5,804,387 A | 9/1998 | Cormack et al. |
| 5,891,646 A | 4/1999 | Barak et al. |
| 5,958,713 A | 9/1999 | Thastrup et al. |
| 5,989,835 A | 11/1999 | Dunlay et al. |
| 6,066,476 A | 5/2000 | Tsien et al. |
| 6,107,324 A | 8/2000 | Behan et al. |
| 6,110,693 A | 8/2000 | Barak et al. |
| 6,140,509 A | 10/2000 | Behan et al. |
| 6,150,393 A | 11/2000 | Behan et al. |

FOREIGN PATENT DOCUMENTS

| | | |
|---|---|---|
| WO | WO88/03168 A1 | 5/1988 |
| WO | WO94/16684 A1 | 8/1994 |
| WO | WO98/12310 A1 | 3/1998 |
| WO | WO98/44350 A1 | 10/1998 |
| WO | WO99/66324 A2 | 12/1999 |
| WO | WO00/12704 A2 | 3/2000 |
| WO | WO01/58923 A2 | 8/2001 |

OTHER PUBLICATIONS

Angers, S., et al., Detection of $\beta_2$-Adrenergic receptor dimerization in living cells using bioluminescence resonance energy transfer (BRET), *Proceedings of the National Academy of Sciences*, vol. 97, No. 7, Mar. 28, 2000, pp. 3684-3689, Proc.Natl. Acad. Sci, USA.

(Continued)

*Primary Examiner*—John Ulm
(74) *Attorney, Agent, or Firm*—Morgan, Lewis & Bockius LLP; David J. Brezner

(57) ABSTRACT

The present invention relates to modified G-protein coupled receptors (GPCRs). The modified GPCRs of the present invention include GPCRs that have been modified to have carboxyl terminal tails comprising one or more sites of phosphorylation, preferably one or more clusters of phosphorylation sites. The modified GPCRs of the present invention may comprise a retained portion of a carboxyl-terminus region from a first GPCR fused to a polypeptide, wherein the polypeptide comprises the one or more clusters of phosphorylation. The present invention also relates to methods of screening compounds and sample solutions for GPCR activity using the modified GPCRs.

3 Claims, 25 Drawing Sheets

OTHER PUBLICATIONS

Attramadal, H., et al., β-*Arrestin2, a Novel Member of the Arrestin/β-Arrestin Gene Family*, Journal of Biological Chemistry, vol. 257, No. 25, Sep. 5, 1992, pp. 17882-17890, The American Society for Biochemistry and Molecular Biology, Inc., USA.

Barak, et al., Abstract #2484, *Molecular Biology of the Cell*, vol. 7, p. 427a Dec. 1996, 6th International Congress on Cell Biology & 36th American Society for Cell Biology Annual Meeting, Dec. 7-11, 1996, San Francisco, CA.

Barak, L.S., et al., Constitutive arrestin-mediated desensitization of a human vasopressin receptor mutant associated with nephrogenic diabetes insipidus, *Proceedings of the National Academy of Sciences*, vol. 98, No. 1, Jan. 2, 2001, pp. 93-98, Proc.Natl. Acad. Sci, USA.

Barak, L.S., et al., A highly Conserved Tyrosine Residue in G Protein-Coupled Receptors is Required for Agonist-mediated $β_2$-Adrenergic Receptor Sequestration, *Journal of Biological Chemistry*, vol. 269, No. 4, Jan. 28, 1994, pp. 2790-2795, The American Society for Biochemistry and Molecular Biology, Inc., USA.

Barak, L.S., et al., A β-Arrestin/Green Fluorescent Protein Biosensor for Detecting G Protein-coupled Receptor Activation, *Journal of Biological Chemistry*, vol. 272, No. 44, Oct. 31, 1997, pp. 27497-27500, The American Society for Biochemistry and Molecular Biology, Inc., USA.

Barak, L.S., et al., The Conserved Seven-Transmembrane Sequence $NP(X)_{2,3}Y$ of the G-Protein-Coupled Receptor Superfamily Regulates Multiple Properties of the $β_2$-Adrenergic Receptor, *Biochemistry*, vol. 34, No. 47, 1995, pp. 15407-15414.

Barak, L.S., et al., Internal Trafficking and Surface Mobility of a Functionally Intact $β_2$-Adrenergic Receptor-Green Fluorescent Protein Conjugate, *Molecular Pharmacology*, 51, 1997, pp. 177-184.

Barak, L.S., et al., Real-time Visualization of the Cellular Redistribution of G-Protein-coupled Receptor Kinase 2 and β-arrestin 2 during Homologous Desensitization of the Substance P Receptor, *Journal of Biological Chemistry*, vol. 274, No. 11, Mar. 12, 1999, pp. 7565-7569, The American Society for Biochemistry and Molecular Biology, Inc., USA.

Cubitt, A., et al., Understanding, Improving and Using Green Fluorescent Proteins, *Trends in Biochemical Sciences*, International Union of Biochemistry and Molecular Biology, 448-455,1995, Elsevier Trends Journals, Oxford, UK.

Drews, J., Drug Discovery: A Historical Perspective, *Science*, vol. 287, Mar. 17, 2000, pp. 1960-1964, American Association for the Advancement of Science, Washington, D.C.

Ferguson, S.S.G., et al., G-protein-coupled receptor regulation: role of G-protein-coupled receptor kinases and arrestins, *Can. J. Physiol, Pharmacol.*, vol. 74, 1996, pp. 1095-1110, NRC, Canada.

Ferguson, S.S.G., et al., Molecular Mechanisms of G-Protein-Coupled Receptor Desensitization and Resensitization, *Life Sciences*, XP-002076355, vol. 62, pp. 1561-1565, 1998, Elsevier Publication, USA.

Ferguson, S.S.G., et al., Role of Phosphorylation in Agonist-promoted $β_2$-Adrenergic Receptor Sequestration, *Journal of Biological Chemistry*, vol. 270, No. 42, Oct. 20, 1995, pp. 24782-24789, The American Society for Biochemistry and Molecular Biology, Inc., USA.

Ferguson, S.S.G., et al., Role of β-arrestin in Mediating Agonist-Promoted G Protein-Coupled Receptor Internalization, *Science*, vol. 271, Jan. 19, 1996, pp. 363-366.

Grady, E., et al., Mechanisms Attenuating Cellular Responses to Neuropeptides: Extracellular Degradation of Ligands and Desensitization of Receptors, *The Journal of Investigative Dermatology Symposium Proceedings*, vol. 21, No. 1, pp. 69-75, Aug. 1997, The Society of Investigative Dermatology, Inc.

Harris, E., et al., *Protein Purification Methods*, pp. 12-18, 1989, Oxford University Press, New York, U.S.

Hausdorff, W.P., et al., A Mutation of the $β^2$-Adrenergic Receptor Impairs Agonist Activation of Adenylyl Cyclase without Affecting High Affinity Agonist Binding, *Journal of Biological Chemistry*, vol. 265, No. 3, Jan. 25, 1990, pp. 1388-1393, The American Society for Biochemistry and Molecular Biology, Inc., USA.

Kim, K.-M., et al., Differential Regulation of the Dopamine $D_2$ and $D_3$ Receptors by G Protein-coupled Receptor Kinases and β-arrestins, *Journal of Biological Chemistry*, vol. 276 No. 40, Oct. 5, 2001, pp. 37409-97414, The American Society for Biochemistry and Molecular Biology, Inc., USA.

Laporte, S. A., et al., The Interaction of β-Arrestin with the AP-2 Adaptor is Required for the Clustering of $β_2$- Adrenergic Receptor into Clathrin-coated Pits, *Journal of Biological Chemistry*, vol. 275, No. 30, Jul. 28, 2000, pp. 23120-23126, The American Society for Biochemistry and Molecular Biology, Inc., USA.

Laporte, S.A., et al., The $β_2$-Adrenergic Receptor/βarrestin complex recruits the clathrin adaptor AP-2 during endocytosis, *Proceedings of the National Academy of Sciences*, vol. 96, No. 7, Mar. 30, 1999, pp. 3712-3717, Proc.Natl. Acad. Sci. USA.

Lohse, M., et al., β-Arrestin: A Protein That Regulates β-Adrenergic Receptor Function, *Science*, vol. 248, pp. 1547-1550, Jun. 22, 1990.

McConalogue, K., et al., Activation and Internalization of the μ-opioid Receptor by the Newly Discovered Endogenous Agonists, Endomorphin-1 and Endomorphin-2, *Neuroscience*, vol. 90, No. 3, pp. 1051-1059, 1999, Elsevier Science Ltd., Great Britain.

McConalogue, K., et al., Cellular and Subcellular Localization of G-Protein Receptor Kinases, Arrestins and G-Proteins: Implications for Receptor Regulation, *Supplement to Gastroenterology*, Digestive Disease Weel and the 96th Annual Meeting of the American Gastroenerological Association, vol. 110, No. 4, Apr. 1996.

McConalogue, K., et al., G Protein-Coupled Receptors in Gastrointestinal Physiology II. Regulation of Neuropeptide receptors in enteric neurons, *Receptor Regulation*, pp. G792-G796, 1998, American Physiological Society.

McConalogue, K., et al., Substance P-Induced Trafficking of β-arrestins, *Journal of Biological Chemistry*, vol. 274, No. 23, pp. 16257-16268, Jun .4, 1999, The American Society for Biochemistry and Molecular Biology, Inc., USA.

Ménard, L., et al., Members the G Protein-Coupled Receptor Kinase Family that Phosphorylate the $β_2$-Adrenergic Receptor FacilitateSequestration, *Biochemistry*, vol. 35, No. 13, 1996, pp. 4155-4160, The American Chemical Society.

Ménard, L., et al., Synergistic Regulation of $B_2$-Adrenergic Receptor Sequestration: Intracellular Complement of $β_2$-Adrenergic Receptor Kinase and β-Arrestin Determine Kinetics of Internalization, *Molecular Pharmacology*, vol. 51, No. 5, May 1997, pp. 800-808, The American Society for Pharmacology and Experimental Therapeutics.

Mhaouty-Kodja, S., et al., Constitutively Active Alpha-1b Adrenergic Receptor Mutants Display Different Phosphorylation and Internalization Features, *Molecular Pharmacology*, vol. 55, No. 2, Feb. 1999, pp. 339-347, The American Society for Pharmacology and Experimental Therapeutics.

Ormö, M., et al., Crystal Structure of the Aequorea victoria Green Fluorescent Proteins, *Science* vol. 273, pp. 1392-1395, 1996, American Association for the Advancement of Science, Washington, D.C.

Oakley, R.H., et al., Association of β-Arrestin with G Protein-coupled Receptors during Clathrin-mediated Endocytosis Dictates the Profile of Receptor Resensitization, *Journal of Biological Chemistry*, vol. 274, No. 45, Nov. 5, 1999, pp. 32248-32257, The American Society for Biochemistry and Molecular Biology, Inc., USA.

Oakley, R.H., et al., Differential Affinities of Visual Arrestin, β-Arrestin1, and β-Arrestin2 for G Protien-coupled Receptors Delineate Two Major Classes of Receptors, *Journal of Biological Chemistry*, vol. 275, No. 22, Jun. 2, 2000, pp. 17201-17210, The American Society for Biochemistry and Molecular Biology, Inc., USA.

Oakley, R.H., et al., Molecular Determinatnts Underlying the Formation of Stable Intracellular G Protein-coupled Receptor—β-Arrestin Complexes after Receptor Endocytosis, *Journal of Biological Chemistry*, vol. 276, No. 22, Jun. 1, 2001, pp. 19452-19460, The American Society for Biochemistry and Molecular Biology, Inc., USA.

Yokoe, Spatial Dynamics of GFP-tagged proteins investigated by local fluorescence enhancement, *Nature Biotechnology*, vol. 14, pp. 1252-1256, Oct. 14, 1996.

Zhang, J., et al., Cellular Trafficking of G Protein-coupled Receptor/β-Arrestin Endocytic Complexes, *Journal of Biological Chemistry*, vol. 274, No. 16, Apr. 16, 1999, pp. 10999-11006, The American Society for Biochemistry and Molecular Biology, Inc., USA.

Zhang, J., et al., A Central Role for β-Arrestins and Clathrin-coated Vesicle-mediated Endocytosis and $\beta_2$-Adrenergic Receptor Resensitization, *Journal of Biological Chemistry*, vol. 272, No. 43, Oct. 24, 1997, pp. 27005-27014, The American Society for Biochemistry and Molecular Biology, Inc., USA.

Borle, A.B., An Overview of Techniques for the Measurement of Calcium Distribution, Calcium Fluxes, and Cytosolic Free Calcium in Mammalian Cells, *Environmental Health Perspectives*, Mar. 1990, pp. 45-56, vol. 84, U.S. Dept of Health and Human Services, U.S.A.

Boss, V., et al., Induction of NFAT-mediated Transcription by $G_q$-coupled Receptors in Lymphoid and Non-lymphoid Cells, *The Journal of Biological Chemistry*, May 3, 1996, pp. 10429-10432, vol. 271, No. 18, The American Society for Biochemistry and Molecular Biology, Inc., USA.

Chen, W., et al., β-Arrestin 2 Mediates Endocytosis of Type III TGF-β Receptor and Down-Regulation of Its Signaling, *Science*, Sep. 5, 2003, pp. 1394-1397, vol. 301, American Association for the Advancement of Science, USA.

Edge, M.D., et al., Total synthesis of a human leukocyte interferon gene, *NATURE*, Aug. 20, 1981, pp. 756-762, vol. 292, No. 5825, American Chemical Society, Macmillian Journals, Ltd.

Inglese, J., et al., Isoprenylation in regulation of signal transduction by G-protein-coupled receptor kinases, *Nature*, Sep. 10, 1992, pp. 147-150, vol. 359, No. 6391, Macmillian Journals, Ltd.

Jay, E., et al., Chemical Synthesis of a Biologically Active Gene for Human Immune Interferon-γ, *The Journal of Biological Chemistry*, May 25, 1984, pp. 6311-6317, vol. 259, No. 10, The American Society of Biological Chemists, Inc., USA.

Lyons, S., et al., An immunological method for detecting gene expression in yeast colonies, *Proceedings of the National Academy of Sciences USA*, Dec. 1984, pp. 7426-7430, vol. 81.

Nambiar, K.P., et al., Total Synthesis and Cloning of a Gene Coding for the Ribonuclease S Protein, *Science*, 1984, pp. 1299-1301, vol. 223, Elsevier Science Inc., USA.

Noren, C.J., et al., A General Method for Site-Specific Incorporation of Unnatural Amino Acids into Proteins, *Science*, Apr. 14, 1989, pp. 182-188. vol. 244, American Association for the Advancement of Science, USA.

FIGURE 1A

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I Rhodopsin like | | | | | |
| | •Amine | | | | |
| | •Acetylcholine (muscarinic & nicotinic) | 5 | Brain, Nerves, Heart | Neurotransmitter | Acuity, Alzheimer's |
| | •Adrenoceptors | | | | |
| | •Alpha Adrenoceptors | 6 | Brain, Kidney, Lung | Gluconeogenesis | Diabetes, Cardiovascular |
| | •Beta Adrenoceptors | 3 | Kidney, Heart | Muscle Contraction | Cardiovascular, Respiratory |
| | •Dopamine | 5 | Brain, Kidney, GI | Neurotransmitter | Cardiovascular, Parkinson's |
| | •Histamine | 2 | Vascular, Heart, Brain | Vascular Permeability | Anti-inflammatory, Ulcers |
| | •Serotonin (5-HT) | 16 | Most Tissues | Neurotransmitter | Depression, Insomnia, Analgesic |
| | •Peptide | | | | |
| | •Angiotensin | 2 | Vascular, Liver, Kidney | Vasoconstriction | Cardiovascular, Endocrine |
| | •Bradykinin | 1 | Liver, Blood | Vasodilation, | Anti-inflammatory, Asthma |
| | •C5a anaphylatoxin | 1 | Blood | Immune System | Anti-inflammatory |
| | •Fmet-leu-phe | 3 | Blood | Chemoattractant | Anti-inflammatory |
| | •Interleukin-8 | 1 | Blood | Chemoattractant | Anti-inflammatory |
| | •Chemokine | 6 | Blood | Chemoattractant | Anti-inflammatory |
| | •Orexin | 2 | Brain | Fat Metabolism | Obesity |
| | •Nociceptin | 1 | Brain | Bronchodilator, Pain | Airway Diseases, Anesthetic |
| | •CCK (Gastrin) | 2 | Gastrointestinal | Motility, Fat Absorption | Gastrointestinal, Obesity, Parkinson's |
| | •Endothelin | 2 | Heart, Bronchus, Brain | Muscle Contraction | Cardiovascular, Respiratory |
| | •Melanocortin | 5 | Kidney, Brain | Metabolic Regulation | Anti-inflammatory, Analgesics |
| | •Neuropeptide Y | 5 | Nerves, Intestine, Blood | Neurotransmitter | Behavior, Memory, Cardiovascular |
| | •Neurotensin | 1 | Brain, | CNS | Cardiovascular, Analgesic |
| | •Opioid | 3 | Brain, | CNS | Depression, Analgesic |
| | •Somatostatin | 5 | Brain, Gastrointestinal | Neurotransmitter | Oncology, Alzheimer's |
| | •Tachykinin (Substance P, NKA₁) | 3 | Brain Nerves | Neurohormone | Depression, Analgesic |

FIGURE 1B

| | | | |
|---|---|---|---|
| •Thrombin | 3 | Platelets, Blood Vessels | Coagulation | Anti-coagulant, Anti-inflammatory |
| •Vasopressin-like | 4 | Arteries, Heart, Bladder | Water Balance | Anti-diuretic, Diabetic Complications |
| •Galanin | 1 | Brain, Pancreas | Neurotransmitter | Analgesics, Alzheimer's |
| •Hormone protein | | | | |
| •Follicle stimulating hormone | 1 | Ovary, Testis | Endocrine | Infertility |
| •Lutropin-choriogonadotropic | 1 | Ovary, Testis | Endocrine | Infertility |
| •Thyrotropin | 1 | Thyroid | Endocrine | Thyroidism, Metabolism |
| •(Rhod)opsin | | | | |
| •Opsin | 5 | Eye | Photoreception | Ophthalmic Diseases |
| •Olfactory | 4(~1000) | Nose | Smell | Olfactory Diseases |
| •Prostanoid | | | | |
| •Prostaglandin | 5 | Arterial, Gastrointestinal | Vasodilation, Pain | Cardiovascular, Analgesic |
| •Lysophosphatidic Acid | 2 | Vessels, Heart, Lung | Inflammation | Cancer, Anti-Inflammatory |
| •Sphingosine-1-phosphate | 2 | Most Cells | Cell proliferation | Cancer |
| •Leukotriene | 1 | White Blood Cells, Bronchus | Inflammation | Asthma, Rheumatoid Arthritis |
| •Prostacyclin | 1 | Arterial, Gastrointestinal | Platelet Regulation | Cardiovascular |
| •Thromboxane | 1 | Arterial, Bronchus | Vasoconstriction | Cardiovascular, Respiratory |
| •Nucleotide-like | | | | |
| •Adenosine | 4 | Vascular, Bronchus | Multiple Effects | Cardiovascular, Respiratory |
| •Purinoceptors | 4 | Vascular, Platelets | Relaxes Muscle | Cardiovascular, Respiratory |
| •Cannabis | 2 | Brain | Sensory Perception | Analgesics, Memory |
| •Platelet activating factor | 1 | Most Peripheral Tissues | Inflammation | Anti-inflammatory, Anti-asthmatic |
| •Gonadotropin-releasing hormone like | | | | |
| •Gonadotropin-releasing hormone | 1 | Reproductive Organs, Pituitary | Reproduction | Prostate Cancer, Endometriosis |
| •Thyrotropin-releasing hormone | 1 | Pituitary, Brain | Thyroid Regulation | Metabolic Regulation |
| •Growth hormone- inhibiting factor | 1 | Gastrointestinal | Neuroendocrine | Oncology, Alzheimer's |
| •Melatonin | 1 | Brain, Eye, Pituitary | Neuroendocrine | Regulation of Circadian Cycle |
| •Class II Secretin like | | | | |
| •Secretin | 1 | Gastrointestinal, Heart | Digestion | Obesity, Gastrointestinal |
| •Calcitonin | 1 | Bone, Brain | Calcium Resorption | Osteoporosis |
| •Corticotropin releasing factor/urocortin | 1 | Adrenal, Vascular, Brain | Neuroendocrine | Stress, Mood, Obesity |
| •Gastric inhibitory peptide (GIP) | 1 | Adrenals, Fat Cells | Sugar/Fat Metabolism | Diabetes, Obesity |
| •Glucagon | 1 | Liver, Fat Cells, Heart | Gluconeogenesis | Cardiovascular |

FIGURE 1C

- Glucagon-like Peptide 1 (GLP-1) — 1 — Pancreas, Stomach, Lung — Gluconeogenesis — Cardiovascular, Diabetes, Obesity
- Growth hormone-releasing hormone — 1 — Brain — Neuroendocrine — Growth Regulation
- Parathyroid hormone — 1 — Bone, Kidney — Calcium Regulation — Osteoporosis
- PACAP — 1 — Brain, Pancreas, Adrenals — Metabolism — Metabolic Regulation
- Vasoactive intestinal polypeptide (VIP) — 1 — Gastrointestinal — Motility — Gastrointestinal

• Class III
- Metabotropic Glutamate — 7 — Brain — Sensory Perception — Hearing, Vision
- GABA$_B$ — 1 — Brain — Neurotransmitter — Mood Disorders
- Extracellular Calcium Sensing — 1 — Parathyroid, Kidney, GI Tract — Calcium Regulation — Cataracts, GI Tumors

FIGURE 2A

G protein-coupled receptors:
(Division into Class A
Or Class B)

1. A1 adenosine receptor [Homo sapiens]. ACCESSION AAB25533
   npivyaf riqkfrvtfl kiwndhfrcq pappidedlp eerpdd
   Class A 2. adrenergic, alpha -1B-, receptor [Homo sapiens]. ACCESSION NP_000670
   npiiypc sskefkrafv rilgcqcrgr grrrrrrrr lggcaytyrp wtrggslers qsrkdsldds gsclsgsqrt
   lpsaspspgy lgrgapppve lcafpewkap gallslpape ppgrrgrhds gplftfkllt epespgtdgg asnggceaaa
   dvangqpgfk snrnplapgqf
   Class A 3. adrenergic receptor alpha-2A [Homo sapiens]. ACCESSION AAG00447
   npviytifn hdfrrafkki lcrgdrkriv
   Class A 4. alpha-2B-adrenergic receptor - human. ACCESSION A37223
   npviytifn qdfrrafrri lcrpwtqtaw
   Class A 5. alpha-2C-adrenergic receptor - human. ACCESSION A31237
   npviytvfn qdfrpsfkhi lfrrrrgfr q
   Class A 6. beta-1-adrenergic receptor [Homo sapiens]. ACCESSION NP_000675
   npiiycrs pdfrkafqgl lccarraarr rhathgdrpr asgclarpgp ppspgaasdd ddddvvgatp parllepwag
   cnggaaadsd ssldepcrpg faseskv
   Class A 7. beta-2 adrenergic receptor. ACCESSION P07550
   npliycrsp dfriafqell clrrsslkay gngyssngnt 361 geqsgyhveq ekenkllced lpgtedfvgh qgtvpsdnid
   sqgrncstnd sll
   Class A 8. dopamine receptor D1 [Homo sapiens]. ACCESSION NP_000785
   npii yafnadfrka fstllgcyrl cpatnnaiet vsinnngaam fsshheprgs iskecnlvyl iphavgssed
   lkkeeaagia rpleklspal svildydtdv slekiqpitq ngqhpt
   Class A 9. D(2) dopamine receptor. ACCESSION P14416
   npiiyttfn iefrkaflki lhc
   Class A

FIGURE 2B

10. d3 dopamine receptor - human. ACCESSION G01977
    np viyttfnief rkaflkilsc
    Class A 11. dopamine receptor D4 - human. ACCESSION DYHUD4
    npviytv fnaefmvfr kalracc
    Class A 12. dopamine receptor D5 - human. ACCESSION DYHUD5
    npviya fnadfqkvfa qllgcshfcs rtpvetvnis nelisynqdi vfhkeiaaay ihmmpnavtp gnrevdndee
    egpfdrmfqi yqtspdgdpv aesvweldce geisldkitp ftpngfh
    Class A 13. muscarinic acetylcholine receptor M1 [Homo sapiens]. ACCESSION NP_000729
    npmcyal cnkafrdtfr llllcrwdkr rwrkipkrpg svhrtpsrqc
    Class A 14. muscarinic acetylcholine receptor M2 [Homo sapiens]. ACCESSION NP_000730
    npacy alcnatfkkt fkhllmchyk nigatr
    Class A 15. muscarinic acetylcholine receptor M3 [Homo sapiens]. ACCESSION NP_000731
    n pvcyalcnkt frttfkmlll cqcdkkkrrk qqyqqrqsvi fhkrapeqal
    Class A 16. muscarinic acetylcholine receptor M4 [Homo sapiens]. ACCESSION NP_000732
    npa cyalcnatfk ktfrhlllcq yrnigtar
    Class A 17. m5 muscarinic receptor. locus HUMACHRM ACCESSION AAA51569
    npicyalcnr tfrktfkmll lcrwkkkkve eklywqgnsk lp
    Class A 18. 5-hydroxytryptamine (serotonin) receptor 1A [Homo sapiens]. ACCESSION BAA90449
    npviy ayfnkdfqna fkkiikckf
    Class A 19. 5-hydroxytryptamine (serotonin) receptor 1B [Homo sapiens]. ACCESSION BAA94455
    npiiyt msnedfkqaf hklirfkcts
    Class A 20. 5-hydroxytryptamine (serotonin) receptor 1E [Homo sapiens]. ACCESSION BAA94458
    n pllytsfned fklafkkkir cre
    Class A

FIGURE 2C

21. OLFACTORY RECEPTOR 6A1. ACCESSION O95222
    npiiyclmq evkralccil hlyqhqdpdp kkgsmv
       Class A 22. OLFACTORY RECEPTOR 2C1. ACCESSION O95371
    npliy tlmmevkga lrrllgkgre vg
       Class A 23. angiotensin receptor 1 [Homo sapiens]. ACCESSION NP_033611
    npl fygflgkkdk ryflqlllkyi ppkakshsnl sfkmsflsyr psdnvssstk kpapcfeve
       Class B 24. angiotensin receptor 2 [Homo sapiens]. ACCESSION NP_000677
    npflycf vgnrfqqklr svfrvpitwl qgkresmscr kssslremet fvs
       Class B 25. interleukin 8 receptor beta (CXCR2) [Homo sapiens]. ACCESSION NM_001557
    NPLIYAFIGQKFRHGLLKILAIHGLISKDSLPKDSRPSFVGSSSGHTSTTL
       Class B 26. cx3c chemokine receptor 1 (cx3cr1) (fractalkine receptor)
    ACCESSION P49238
    np liyafagekf rrylyhlygk clavlcgrsv hvdfsssesq rsrhgsvlss nftyhtsdgd alll
       Class B 27. neurotensin receptor - human. ACCESSION S29506
    n pilynlvsan frhiflatla clcpvwrrrr krpafsrkad svssnhflss natretly
       Class B 28. SUBSTANCE-P RECEPTOR (SPR) (NK-1 RECEPTOR) (NK-1R). ACCESSION P25103
    npiiyccclnd rfrlgfkhaf rccpfisagd yeglemkstr ylqtqgsvyk vsrletfistvvgaheeepe dgpkafpssl
    dltsncssrs dsktmtesfs fssnvls
       Class B 29. vasopressin receptor type 2 [Homo sapiens]. ACCESSION AAD16444
    npwiyasfss svsselrsll ccargrtpps lgpqdescff assslakdts s
       Class B 30. thyrotropin-releasing hormone receptor - human. ACCESSION JN0708
    npviy nlmsqkfraa frklcnckqk ptekpanysv alnysvikes dhfsfelddi tvtdtylsaf kvsfddtcla sevsfsqs
       Class B 31. oxytocin receptor - human. ACCESSION A55493
    npwiym lftghlfhel vqrflccsas ylkgrrlget saskksnsss fvlshrsssq rscsqpsta
       Class B

FIGURE 2D

32. neuromedin U receptor [Homo sapiens]. ACCESSION AAG24793
    npvlyslmssrfretfqealclgacchrlrprhsshslsrmttgstlcdvgslgswvhplagndgpeaqqetdps
    Class B 33. gastrin receptor. ACCESSION AAC37528
    nplvy cfmhrrfrqa cletcarccp rpprarpral pdedpptpsi aslsrlsytt isflgpg
    Class B 34. galanin receptor 3 [Homo sapiens]. ACCESSION 10879541
    nplv yalasrhfra rfrrlwpcgr rrrhrarral rrvrpassgp pgcpgdarps grllagggqg pepregpvhg geaargpe
    Class A 35. edg-1 - human. ACCESSION A35300
    npiiy tltnkemrra firimscckc psgdsagkfk rpiiagmefs rsksdnsshp 361 qkdegdnpet imssgnvnss s
    Class A 36. central cannabinoid receptor [Homo sapiens]. ACCESSION NP_057167
    npiiyalr skdlrhafrs mfpscegtaq pldnsmgdsd clhkhannaa svhraaesci kstvkiakvt msvstdtsae al
    Class A 37. delta opioid receptor - human. ACCESSION I38532
    npvlyaf ldenfkrcfr qlcrkpcgrp dpssfsrpre atarervtac tpsdgpgggr aa
    Class A 38. proteinase activated receptor 2 (PAR-2) human. ACCESSION P55085
    dpfvyyfvshdfrdhaknallcrsvrtvkqmqvsltskkhsrksssysssttvktsy
    Class A 39. vasopressive intestinal peptide receptor (VIPR) rat. ACCESSION NM_012685
    NGEVQAELRRKWRRWHLQGVLGWSSKSQHPWGGSNGATCSTQVSMLTRVSPSARR
    SSSFQAEVSLV
    Class B

FIGURE 3A

Human V2R DNA (nucleotides encoding the last 29 amino acids of the V2R and the adjacent stop codon):

gcccggggacgcaccccacccagcctgggtccccaagatgagtcctgcaccaccgccagctcct
ccctggccaaggacacttcatcgtga

FIGURE 3B

PCR amplified human V2R DNA fragment:

gcggccgcacggggacgcaccccacccagcctgggtccccaagatgagtcctgcaccaccgcc
agctcctccctggccaaggacacttcatcgtgaagatctccgcggtctaga

*Additions and changes to the V2R DNA are underlined.

*The Sma I (cccggg) restriction enzyme site (underlined in Fig. 3A) was eliminated in the amplified DNA fragment by changing a cytosine to an adenine.

*A Not I restriction site (gcggccgc) was incorporated into the amplified DNA fragment by adding 6 nucleotides (gcggcc) to the 5' end of the V2R DNA.

*Bgl II (agatct), Sac II (ccgcgg), and Xba I (tctaga) restriction enzyme sites were added to the 3' end of the V2R DNA.

FIGURE 4A
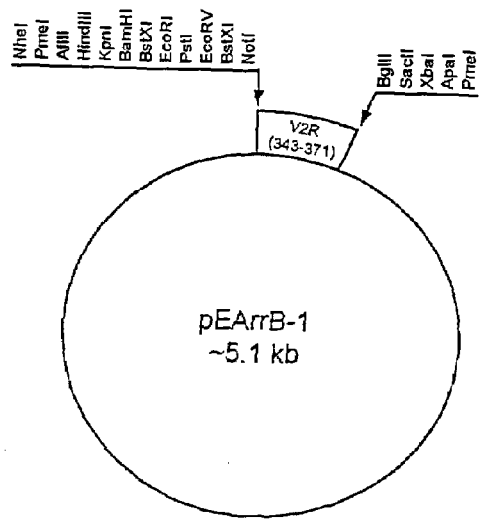
FIGURE 4B
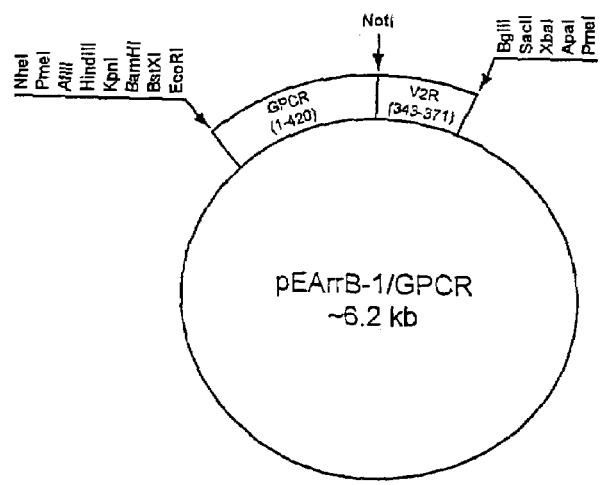
FIGURE 4C
...AAARGRTPPSLGPQDESCTTASSSLAKDTSS

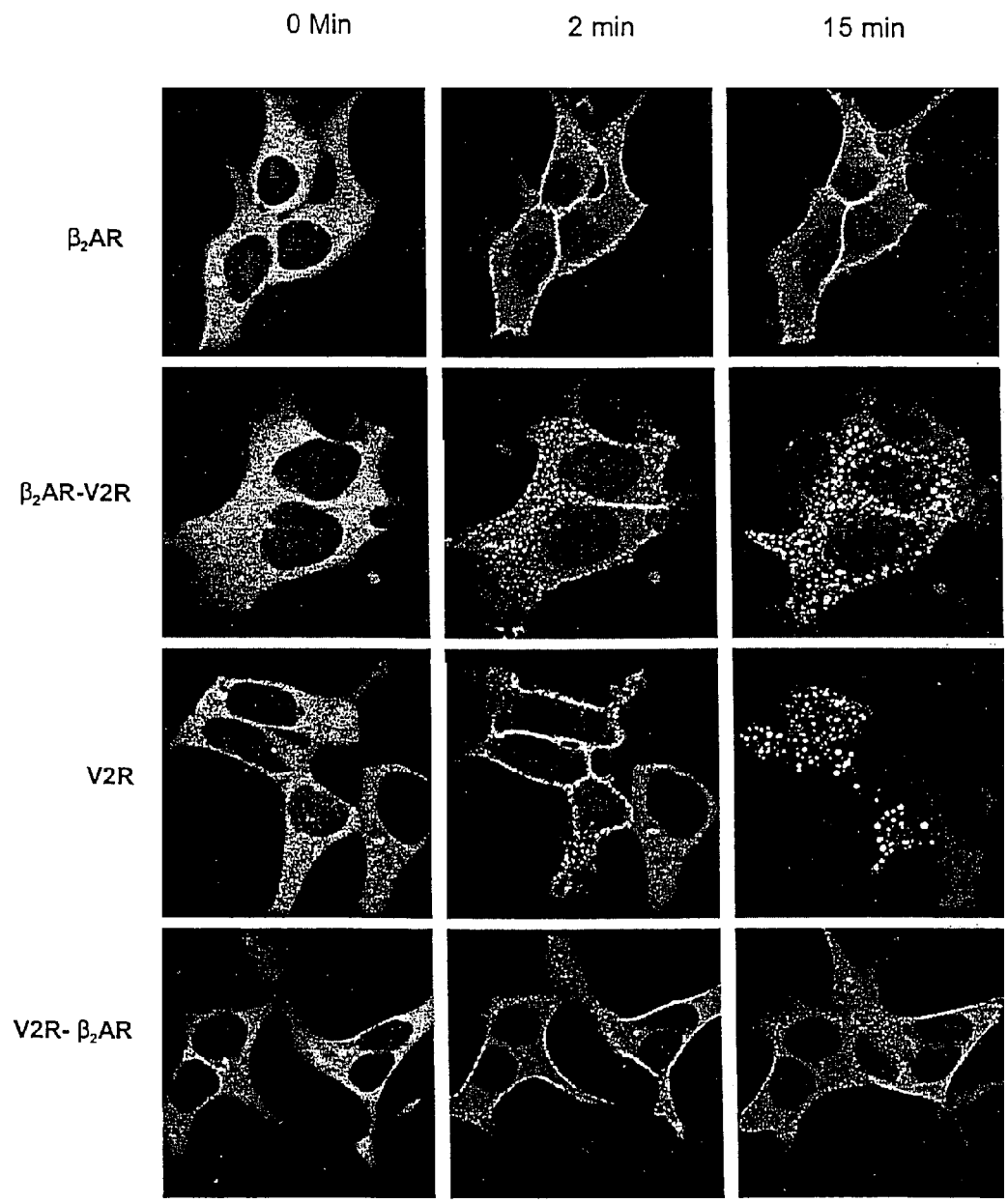

FIGURE 8A

1) V2R               CARGRTPPSLGPQDESCTTASSSLAKDTSS
2) V2R-S362X         CARGRTPPSLGPQDESCTTA
3) V2R-SSSTSS/AAAAAA CARGRTPPSLGPQDESCTTAAAAALAKDAAA
4) V2R-TSS/AAA       CARGRTPPSLGPQDESCTTASSSLAKDAAA
5) V24-SSS/AAA       CARGRTPPSLGPQDESCTTAAAALAKDTSS
6) β$_2$AR-V2R-SSS/AAA  CARGRTPPSLGPQDESCTTAAAAALAKDTSS
7) β$_2$AR           CLRRSSLKAYGNGYSSNGNTGEQSGYHVEQEKENKLLCEDLP-
                     GTEDFVGHQGTVPSDNIDSQGRNCSTNDSLL
8) β$_2$AR413-V2R10  CLRRSSLKAYGNGYSSNGNTGEQSGYHVEQEKENKLLCEDLP-
                     GTEDFVGHQGTVPSDNIDSQGRNCSTNDSLLSSSLAKDTSS
9) β$_2$AR360-V2R10  CLRRSSLKAYGNGYSSNGNTSSSLAKDTSS

FIGURE 8B

V2R    NPWIYASFSSSVSSELRSLLCCARGRTPPSLGPQDESCTTASSSLAKDTSS
AAA-1  -------------------------------------------AAA------
AAA-2  ---------------------------------------------------AAA

NTR-1  NPILYNLVSANFRQVFLSTLACLCPGWRHRRKKRPTFSRKPNSMSSNHAFSTSATRETLY
AMAA   -------------------------------------------A-AA------------
AAA    ---------------------------------------------------AAA------

OTR    NPWIYMLFTGHLFHELVQRFLCCSASYLKGRRLGETSASKKSNSSSFVLSHRSSQRSCSQPSTA
AAAA   --------------------------------AAAA---------------------------
AAA-1  -------------------------------------------AAA-----------------
AAA-2  ---------------------------------------------------AAA---------

FIGURE 8C

```
SPR   NPIIYCCLNDRFRLGFKHAFRCCPFISAGDYEGLEMKSTRYLQTQGVYKVSRLETTISTVVGAHEEPEDGPKATPSSLKLTSNCSSRSDSKTMTESFSFSSNVLS
383X  ------------------------------------------------------------------------------------------------X---------
355X  ------------------------------------------------------------------------------------------X---------------
325X  -----X---------------------------------------------------------------------------------------------------
AAIAA -----------------------------------------------------AA-AA---------------------------------------------
APAA  ------------------------------------------------------------------------A-AA----------------------------
```

FIGURE 9A

Amino Acid Sequence of the Wild-Type Receptors

Amino acid sequence of the wild-type V2R

MLMASTTSAVPGHPSLPSLPSNSSQERPLDTRDPLLARAELALLSIVFVAVALSNGLVLAA
LARRGRRGHWAPIHVFIGHLCLADLAVALFQVLPQLAWKATDRFRGPDALCRAVKYLQMVG
MYASSYMILAMTLDRHRAICRPMLAYRHGSGAHWNRPVLVAWAFSLLLSLPQLFIFAQRNV
EGGSGVTDCWACFAEPWGRRTYVTWIALMVFVAPTLGIAACQVLIFREIHASLVPGPSERP
GGRRRGRRTGSPGEGAHVSAAVAKTVRMTLVIVVVYVLCWAPFFLVQLWAAWDPEAPLEGA
PFVLLMLLASLNSCTNPWIYASFSSSVSSELRSLLCCARGRTPPSLGPQDESCTTASSSLA
KDTSS
(Seq.ID No.1)

FIGURE 9B

Amino acid sequence of the wild-type β₂AR

MGQPGNGSAFLLAPNRSHAPDHDVTQQRDEVWVVGMGIVMSLIVLAIVFGNVLVITAIAKF
ERLQTVTNYFITSLACADLVMGLAVVPFGAAHILMKMWTFGNFWCEFWTSIDVLCVTASIE
TLCVIAVDRYFAITSPFKYQSLLTKNKARVIILMVWIVSGLTSFLPIQMHWYRATHQEAIN
CYANETCCDFFTNQAYAIASSIVSFYVPLVIMVFVYSRVFQEAKRQLQKIDKSEGRFHVQN
LSQVEQDGRTGHGLRRSSKFCLKEHKALKTLGIIMGTFTLCWLPFFIVNIVHVIQDNLIRK
EVYILLNWIGYVNSGFNPLIYCRSPDFRIAFQELLCLRRSSLKAYGNGYSSNGNTGEQSGY
HVEQEKENKLLCEDLPGTEDFVGHQGTVPSDNIDSQGRNCSTNDSLL
(Seq. ID No. 2)

FIGURE 9C

Amino Acid Sequence of the Chimeric Receptors

Amino acid sequence of the β₂AR-V2R chimera (Oakley et al.)

MGQPGNGSAFLLAPNRSHAPDHDVTQQRDEVWVVGMGIVMSLIVLAIVFGNVLVITAIAKF
ERLQTVTNYFITSLACADLVMGLAVVPFGAAHILMKMWTFGNFWCEFWTSIDVLCVTASIE
TLCVIAVDRYFAITSPFKYQSLLTKNKARVIILMVWIVSGLTSFLPIQMHWYRATHQEAIN
CYANETCCDFFTNQAYAIASSIVSFYVPLVIMVFVYSRVFQEAKRQLQKIDKSEGRFHVQN
LSQVEQDGRTGHGLRRSSKFCLKEHKALKTLGIIMGTFTLCWLPFFIVNIVHVIQDNLIRK
EVYILLNWIGYVNSGFNPLIYCRSPDFRIAFQELLCARGRTPPSLGPQDESCTTASSSLAK
DTSS
(Seq. ID No. 3)

*shown in bold are the amino acids that were moved to the β₂AR to increase its affinity for arrestin.

FIGURE 10A

Amino acid sequence of the MOR-V2R chimera expressed from the pEArrB-1/MOR vector MDSSTGPGNTSDCSDPLAQASCSPAPGSWLNLSHVDGNQSDPCGLNRTGLG
GNDSLCPQTGSPSMVTAITIMALYSIVCVVGLFGNFLVMYVIVRYTKMKTA
TNIYIFNLALADALATSTLPFQSVNYLMGTWPFGTILCKIVISIDYYNMFT
SIFTLCTMSVDRYIAVCHPVKALDFRTPRNAKIVNVCNWILSSAIGLPVMF
MATTKYRQGSIDCTLTFSHPTWYWENLLKICVFIFAFIMPILIITVCYGLM
ILRLKSVRMLSGSKEKDRNLRRITRMVLVVVAVFIVCWTPIHIYVIIKALI
TIPETTFQTVSWHFCIALGYTNSCLNPVLYAFLDENFKRCFREFCAAARGR
TPPSLGPQDESCTTASSSLAKDTSS (Seq. ID No. 4)

FIGURE 10B

Amino acid sequence of the D1AR-V2R chimera expressed from the pEArrB-1/D1AR vector MAPNTSTMDEAGLPAERDFSFRILTACFLSLLILSTLLGNTLVCAAVIRFR
HLRSKVTNFFVISLAVSDLLVAVLVMPWKAVAEIAGFWPFGSFCNIWVAFD
IMCSTASILNLCVISVDRYWAISSPFQYERKMTPKAAFILISVAWTLSVLI
SFIPVQLSWHKAKPTWPLDGNFTSLEDTEDDNCDTRLSRTYAISSSLISFY
IPVAIMIVTYTSIYRIAQKQIRRISALERAAVHAKNCQTTAGNGNPVECAQ
SESSFKMSFKRETKVLKTLSVIMGVFVCCWLPFFISNCMVPFCGSEETQPF
CIDSITFDVFVWFGWANSSLNPIIYAFNADFQKAFSTLLGCYRLCAAARGR
TPPSLGPQDESCTTASSSLAKDTSS (Seq. ID No. 5)

FIGURE 10C

Amino acid sequence of the 5HT1AR-V2R chimera expressed from the pEArrB-1/5HT1AR vector MDVLSPGQGNNTTSPPAPFETGGNTTGISDVTVSYQVITSLLLGTLIFCAV
LGNACVVAAIALERSLQNVANYLIGSLAVTDLMVSVLVLPMAALYQVLNKW
TLGQVTCDLFIALDVLCCTSSILHLCAIALDRYWAITDPIDYVNKRTPRRA
AALISLTWLIGFLISIPPMLGWRTPEDRSDPDACTISKDHGYTIYSTFGAF
YIPLLLMLVLYGRIFRAARFRIRKTVKKVEKTGADTRHGASPAPQPKKSVN
GESGSRNWRLGVESKAGGALCANGAVRQGDDGAALEVIEVHRVGNSKEHLP
LPSEAGPTCAPASFERKNERNAEAKRKMALARERKTVKTLGIIMGTFILC
WLPFFIVALVLPFCESSCHMPTLLGAI
INWLGYSNSLLNPVIYAYFNKDFQNAFKKIIKCNFCAAARGRTPPSLGPQD
ESCTTASSSLAKDTSS
(Seq. ID No. 6)

FIGURE 10D

Amino acid sequence of the β3AR-V2R chimera expressed from the pEArrB-1/β3AR vector MAPWPHENSSLAPWPDLPTLAPNTANTSGLPGVPWEAALAGALLALAVLAT
VGGNLLVIVAIAWTPRLQTMTNVFVTSLAAADLVMGLLVVPPAATLALTGH
WPLGATGCELWTSVDVLCVTASIETLCALAVDRYLAVTNPLRYGALVTKRC
ARTAVVLVWVVSAAVSFAPIMSQWWRVGADAEAQRCHSNPRCCAFASNMPY
VLLSSSVSFYLPLLVMLFVYARVFVVATRQLRLLRGELGRFPPEESPPAPS
RSLAPAPVGTCAPPEGVPACGRRPARLLPLREHRALCTLGLIMGTFTLCWL
PFFLANVLRALGGPSLVPGPAFLALNWLGYANSAFNPLIYCRSPDFRSAFR
RLLCRCAAARGRTPPSLGPQDESCTTASSSLAKDTSS
(Seq. ID No. 7)

FIGURE 10E

Amino acid sequence of the Edg1R-V2R chimera expressed from the pEArrB-1/Edg1R vector MGPTSVPLVKAHRSSVSDYVNYDIIVRHYNYTGKLNISADKENSIKLTSVV
FILICCFIILENIFVLLTIWKTKKFHRPMYYFIGNLALSDLLAGVAYTANL
LLSGATTYKLTPAQWFLREGSMFVALSASVFSLLAIAIERYITMLKMKLHN
GSNNFRLFLLISACWVISLILGGLPIMGWNCISALSSCSTVLPLYHKHYIL
FCTTVFTLLLLSIVILYCRIYSLVRTRSRRLTFRKNISKASRSSEKSLALL
KTVIIVLSVFIACWAPLFILLLLDVGCKVKTCDILFRAEYFLVLAVLNSGT
NPIIYTLTNKEMRRAFIRIMSCCKCAAARGRTPPSLGPQDESCTTASSSLA
KDTSS
(Seq. ID No. 8)

FIGURE 11A

Nucleotide sequence of the β2AR-V2R chimera atggggcaacccgggaacggcagcgccttcttgctggcacccaatagaagccatgcgccggacc
acgacgtcacgcagcaaagggacgaggtgtgggtggtgggcatgggcatcgtcatgtctctcat
cgtcctggccatcgtgtttggcaatgtgctggtcatcacagccattgccaagttcgagcgtctg
cagacggtcaccaactacttcatcacttcactggcctgtgctgatctggtcatgggcctggcag
tggtgccctttggggccgcccatattcttatgaaatgtggacttttggcaacttctggtgcga
gttttggacttccattgatgtgctgtgcgtcacggccagcattgagaccctgtgcgtgatcgca
gtggatcgctactttgccattacttcacctttcaagtaccagagcctgctgaccaagaataagg
cccgggtgatcattctgatggtgtggattgtgtcaggccttacctccttcttgcccattcagat
gcactggtaccgggccacccaccaggaagccatcaactgctatgccaatgagacctgctgtgac
ttcttcacgaaccaagcctatgccattgcctcttccatcgtgtccttctacgttcccctggtga
tcatggtcttcgtctactccagggtctttcaggaggccaaaaggcagctccagaagattgacaa
atctgagggccgcttccatgtccagaaccttagccaggtggagcaggatgggcggacggggcat
ggactccgcagatcttccaagttctgcttgaaggagcacaaagccctcaagacgttaggcatca
tcatgggcactttcacccttctgctggctgcccttcttcatcgttaacattgtgcatgtgatcca
ggataacctcatccgtaaggaagtttacatcctcctaaattggataggctatgtcaattctggt
ttcaatccccttatctactgccggagcccagatttcaggattgccttccaggagcttctgtgcg
cccggggacgcaccccacccagcctgggtccccaagatgagtcctgcaccaccgccagctcctc
cctggccaaggacacttcatcgtga
(SEQ ID No. 9)

FIGURE 11B

Nucleotide sequence of the MOR-V2R chimera atggacagcagcaccggcccagggaacaccagcgactgctcagacccccttagctcaggcaagtt
gctccccagcacctggctcctggctcaacttgtcccacgttgatggcaaccagtccgatccatg
cggtctgaaccgcaccgggcttggcgggaacgacagcctgtgccctcagaccggcagcccttcc
atggtcacagccattaccatcatggccctctactctatcgtgtgtgtagtgggcctcttcggaa
acttcctggtcatgtatgtgattgtaagatacaccaaaatgaagactgccaccaacatctacat
tttcaaccttgctctggcagacgccttagcgaccagtacactgcccttcagagtgtcaactac
ctgatgggaacatggcccttcggaaccatcctctgcaagatcgtgatctcaatagattactaca
acatgttcaccagcatattcaccctctgcaccatgagcgtggaccgctacattgctgtctgcca
cccagtcaaagccctggatttccgtaccccccgaaatgccaaaatcgtcaacgtctgcaactgg
atcctctcttctgccatcggtctgcctgtaatgttcatggcaaccacaaaatacaggcagggt
ccatagattgcaccctcacgttctcccacccaacctggtactgggagaacctgctcaaaatctg
tgtctttatcttcgctttcatcatgccgatcctcatcatcactgtgtgttacggcctgatgatc
ttacgactcaagagcgttcgcatgctatcgggctccaaagaaaaggacaggaatctgcgcagga
tcacccggatggtgctggtggtcgtggctgtatttatcgtctgctggacccccatccacatcta
cgtcatcatcaaagcgctgatcacgattccagaaaccacatttcagaccgtttcctggcacttc
tgcattgctttgggttacacgaacagctgcctgaatccagttctttacgccttcctggatgaaa
acttcaagcgatgcttcagagagttctgcgcggccgcacggggacgcacccccaccagcctggg
tccccaagatgagtcctgcaccaccgccagctcctcctggccaaggacacttcatcgtga
(SEQ ID No. 10)

FIGURE 11C

Nucleotide sequence of the D1AR-V2R chimera atggctcctaacacttctaccatggatgaggccgggctgccagcggagagggatttctcctttc
gcatcctcacggcctgtttcctgtcactgctcatcctgtccactctcctgggcaataccttgt
ctgtgcggccgtcatccggtttcgacacctgaggtccaaggtgaccaacttctttgtcatctct
ttagctgtgtcagatctcttggtggctgtcctggtcatgccctggaaagctgtggccgagattg
ctggcttttggcctttgggtccttttgtaacatctgggtagcctttgacatcatgtgctctac
ggcgtccattctgaacctctgcgtgatcagcgtggacaggtactgggctatctccagcccttc
cagtatgagaggaagatgaccccccaaagcagccttcatcctgattagcgtagcatggactctgt
ctgtccttatatccttcatcccagtacagctaagctggcacaaggcaaagcccacatggcccctt
ggatggcaattttacctccctggaggacaccgaggatgacaactgtgacacaaggttgagcagg
acgtatgccatttcatcgtccctcatcagcttttacatccccgtagccattatgatcgtcacct
acaccagtatctacaggattgcccagaagcaaaccggcgcatctcagccttggagagggcagca
gtccatgccaagaattgccagaccaccgcaggtaacgggaaccccgtcgaatgcgcccagtctg
aaagttccttaagatgtccttcaagagggagacgaaagttctaaagacgctgtctgtgatcat
gggggtgtttgtgtgctgctggctccctttcttcatctcgaactgtatggtgcccttctgtggc
tctgaggagacccagccattctgcatcgattccatcaccttcgatgtgtttgtgtggtttgggt
gggcgaattcttccctgaacccattatttatgcttttaatgctgacttccagaaggcgttctc
aaccctcttaggatgctacagactctgcgcggccgcacggggacgcacccaccccagcctgggt
ccccaagatgagtcctgcaccaccgccagctcctccctggccaaggacacttcatcgtga
(SEQ ID No. 11)

FIGURE 11D

Nucleotide sequence of the 5HT1AR-V2R chimera atggatgtgctcagccctggtcagggcaacaacaccacatcaccaccggctccctttgagaccg
gcggcaacactactggtatctccgacgtgaccgtcagctaccaagtgatcacctctctgctgct
gggcacgctcatcttctgcgcggtgctgggcaatgcgtgcgtggtggctgccatcgccttggag
cgctccctgcagaacgtggccaattatcttattggctcttggcggtcaccgacctcatggtgt
cggtgttggtgctgcccatggccgcgctgtatcaggtgctcaacaagtggacactgggccaggt
aacctgcgacctgttcatcgccctcgacgtgctgtgctgcacctcatccatcttgcacctgtgc
gccatcgcgctggacaggtactgggccatcacggaccccatcgactacgtgaacaagaggacgc
ccggcgcgccgctgcgctcatctcgctcacttggcttattggcttcctcatctctatcccgcc
catgctgggctggcgcaccccggaagacgctcggaccccgacgcatgcaccattagcaaggat
catggctacactatctattccaccttggagctttctacatcccgctgctgctcatgctggttc
tctatgggcgcatattccgagctgcgcgcttccgcatccgcaagacggtcaaaaaggtggagaa
gaccggagcggacacccgccatggagcatctcccgccccgcagcccaagaagagtgtgaatgga
gagtcggggagcaggaactggaggctgggcgtggagagcaaggctgggggtgctctgtgcgcca
atggcgcggtgaggcaaggtgacgatggcgccgccctggaggtgatcgaggtgcaccgagtggg
caactccaaagagcacttgcctctgcccagcgaggctggtcctaccccttgtgcccccgcctct
ttcgagaggaaaaatgagcgcaacgccgaggcgaagcgcaagatggccctggcccgagagagga
agacagtgaagacgctgggcatcatcatgggcaccttcatcctctgctggctgcccttcttcat
cgtggctcttgttctgcccttctgcgagagcagctgccacatgcccaccctgttgggcgccata
atcaattggctgggctactccaactctctgcttaacccgtcatttacgcatacttcaacaagg
actttcaaaacgcgtttaagaagatcattaagtgtaacttctgcgcggccgcacggggacgcac
cccacccagcctgggtccccaagatgagtcctgcaccaccgccagctcctccctggccaaggac
acttcatcgtga
(SEQ ID No. 12)

FIGURE 11E

Nucleotide sequence of the β3AR-V2R chimera atggctccgtggcctcacgagaacagctctcttgcccatggccggacctcccacctggcgc
ccaataccgccaacaccagtgggctgccaggggttccgtgggaggcggccctagccggggccct
gctggcgctggcggtgctcgccaccgtggggaggcaacctgctggtcatcgtggccatcgcctgg
actccgagactccagaccatgaccaacgtgttcgtgacttcgctggccgcagccgacctggtga
tgggactcctggtggtgccgccggcggccaccttggcgctgactggccactggccgttgggcgc
cactggctgcgagctgtggacctcggtggacgtgctgtgtgtgaccgccagcatcgaaaccctg
tgcgccctggccgtggaccgctacctggctgtgaccaacccgctgcgttacggcgcactggtca
ccaagcgctgcgcccggacagctgtggtcctggtgtgggtcgtgtcggccgcggtgtcgtttgc
gcccatcatgagccagtggtggcgcgtaggggccgacgccgaggcgcagcgctgccactccaac
ccgcgctgctgtgccttcgcctccaacatgccctacgtgctgctgtcctcctccgtctccttct
accttcctcttctcgtgatgctcttcgtctacgcgcgggttttcgtggtggctacgcgccagct
gcgcttgctgcgcggggagctgggccgctttccgcccgaggagtctccgccggcgccgtcgcgc
tctctggccccggccccggtggggacgtgcgctccgcccgaaggggtgcccgcctgcggcggc
ggccgcgcgcctcctgcctctcgggaacaccgggccctgtgcaccttgggtctcatcatggg
caccttcactctctgctggttgcccttctttctggccaacgtgctgcgcgccctgggggggcccc
tctctagtcccgggcccggctttccttgccctgaactggctaggttatgccaattctgccttca
acccgctcatctactgccgcagcccggactttcgcagcgccttccgccgtcttctgtgccgctg
cgcggccgcacggggacgcacccaccagcctgggtccccaagatgagtcctgcaccaccgcca
gctcctccctggccaaggacacttcatcgtga
(SEQ ID No. 13)

FIGURE 11F

Nucleotide sequence of the Edg1-V2R chimera atggggcccaccagcgtcccgctggtcaaggccaccgcagctcggtctctgactacgtcaact
atgatatcatcgtccggcattacaactacacgggaaagctgaatatcagcgcggacaaggagaa
cagcattaaactgacctcggtggtgttcattctcatctgctgctttatcatcctggagaacatc
tttgtcttgctgaccatttggaaaaccaagaaattccaccgacccatgtactatttattggca
atctggccctctcagacctgttggcaggagtagcctacacagctaacctgctcttgtctggggc
caccacctacaagctcactcccgcccagtggtttctgcgggaagggagtatgtttgtggccctg
tcagcctccgtgttcagtctcctcgccatcgccattgagcgctatatcacaatgctgaaaatga
aactccacaacgggagcaataacttccgcctcttcctgctaatcagcgcctgctgggtcatctc
cctcatcctgggtggcctgcctatcatgggctggaactgcatcagtgcgctgtccagctgctcc
accgtgctgccgctctaccacaagcactatatcctcttctgcaccacggtcttcactctgcttc
tgctctccatcgtcattctgtactgcagaatctactccttggtcaggactcggagccgcgcct
gacgttccgcaagaacatttccaaggccagccgcagctctgagaagtcgctggcgctgctcaag
accgtaattatcgtcctgagcgtcttcatcgcctgctgggcaccgctcttcatcctgctcctgc
tggatgtgggctgcaaggtgaagacctgtgacatcctcttcagagcggagtacttcctggtgtt
agctgtgctcaactccggcaccaacccatcatttacactctgaccaacaaggagatgcgtcgg
gccttcatccggatcatgtcctgctgcaagtgcgcggccgcacggggacgcacccacccagcc
tgggtccccaagatgagtcctgcaccaccgccagctcctccctggccaaggacacttcatcgtg
a
(SEQ ID No. 14)

βarr2-GFP Translocation to the MOR and MOR-V2R Chimera in Response to Morphine

βarr2-GFP Translocation to the D1AR and D1AR-V2R Chimera in Response to Dopamine βarr2-GFP Translocation to the 5HT1AR and 5HT1AR-V2R Chimera in Response to Serotonin βarr2-GFP Translocation to the β3AR and β3AR-V2R Chimera in Response to Isoproterenol βarr2-GFP Translocation to the Edg1 and Edg1-V2R Chimera in Response to Sphingosine-1-Phosphate

SEQUENCE LISTING

<160> NUMBER OF SEQ ID NOS: 82

<210> SEQ ID NO 1
<211> LENGTH: 371
<212> TYPE: PRT
<213> ORGANISM: Artificial Sequence
<220> FEATURE:
<223> OTHER INFORMATION: amino acid sequence of wild-type V2R

<400> SEQUENCE: 1

```
Met Leu Met Ala Ser Thr Thr Ser Ala Val Pro Gly His Pro Ser Leu
 1               5                  10                  15

Pro Ser Leu Pro Ser Asn Ser Ser Gln Glu Arg Pro Leu Asp Thr Arg
            20                  25                  30

Asp Pro Leu Leu Ala Arg Ala Glu Leu Ala Leu Leu Ser Ile Val Phe
        35                  40                  45

Val Ala Val Ala Leu Ser Asn Gly Leu Val Leu Ala Ala Leu Ala Arg
    50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
        115                 120                 125

Met Ile Leu Ala Met Thr Leu Asp Arg His Arg Ala Ile Cys Arg Pro
    130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
        195                 200                 205

Ile Ala Leu Met Val Phe Val Ala Pro Thr Leu Gly Ile Ala Ala Cys
    210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Ala Val Ala Lys Thr Val Arg Met
            260                 265                 270
```

```
Thr Leu Val Ile Val Val Tyr Val Leu Cys Trp Ala Pro Phe Phe
            275                 280                 285

Leu Val Gln Leu Trp Ala Ala Trp Asp Pro Glu Ala Pro Leu Glu Gly
        290                 295                 300

Ala Pro Phe Val Leu Leu Met Leu Leu Ala Ser Leu Asn Ser Cys Thr
305                 310                 315                 320

Asn Pro Trp Ile Tyr Ala Ser Phe Ser Ser Val Ser Ser Glu Leu
            325                 330                 335

Arg Ser Leu Leu Cys Cys Ala Arg Gly Arg Thr Pro Pro Ser Leu Gly
            340                 345                 350

Pro Gln Asp Glu Ser Cys Thr Thr Ala Ser Ser Ser Leu Ala Lys Asp
            355                 360                 365

Thr Ser Ser
    370
```

<210> SEQ ID NO 2
<211> LENGTH: 413
<212> TYPE: PRT
<213> ORGANISM: Artificial Sequence
<220> FEATURE:
<223> OTHER INFORMATION: amino acid sequence of wild-type beta2AR

<400> SEQUENCE: 2

```
Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255
```

```
Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410
```

<210> SEQ ID NO 3
<211> LENGTH: 370
<212> TYPE: PRT
<213> ORGANISM: Artificial Sequence
<220> FEATURE:
<223> OTHER INFORMATION: amino acid sequence of beta2-AR-V2R chimera

<400> SEQUENCE: 3

```
Met Gly Gln Pro Gly Asn Gly Ser Ala Phe Leu Leu Ala Pro Asn Arg
 1               5                  10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
            35                  40                  45

Phe Gly Asn Val Leu Val Ile Thr Ala Ile Ala Lys Phe Glu Arg Leu
 50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
            85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
            130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
            165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
            195                 200                 205
```

-continued

```
Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Ala Arg Gly Arg Thr Pro Pro Ser Leu Gly Pro
            340                 345                 350

Gln Asp Glu Ser Cys Thr Thr Ala Ser Ser Ser Leu Ala Lys Asp Thr
        355                 360                 365

Ser Ser
    370
```

<210> SEQ ID NO 4
<211> LENGTH: 382
<212> TYPE: PRT
<213> ORGANISM: Artificial Sequence
<220> FEATURE:
<223> OTHER INFORMATION: amino acid sequence of MOR-V2R chimera expressed from the pEArrB-1/MOR vector

<400> SEQUENCE: 4

```
Met Asp Ser Ser Thr Gly Pro Gly Asn Thr Ser Asp Cys Ser Asp Pro
 1               5                  10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
```

```
                    180                 185                 190
Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Ile Leu Ile Thr Val Cys Tyr Gly Leu Met Ile
            245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Lys Ala
            290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ala
            340                 345                 350

Ala Ala Arg Gly Arg Thr Pro Pro Ser Leu Gly Pro Gln Asp Glu Ser
            355                 360                 365

Cys Thr Thr Ala Ser Ser Ser Leu Ala Lys Asp Thr Ser Ser
370                 375                 380

<210> SEQ ID NO 5
<211> LENGTH: 382
<212> TYPE: PRT
<213> ORGANISM: Artificial Sequence
<220> FEATURE:
<223> OTHER INFORMATION: amino acid sequence of D1AR-V2R chimera
      expressed from the pEArrB-1/D1AR vector

<400> SEQUENCE: 5

Met Ala Pro Asn Thr Ser Thr Met Asp Glu Ala Gly Leu Pro Ala Glu
1               5                   10                  15

Arg Asp Phe Ser Phe Arg Ile Leu Thr Ala Cys Phe Leu Ser Leu Leu
            20                  25                  30

Ile Leu Ser Thr Leu Leu Gly Asn Thr Leu Val Cys Ala Ala Val Ile
        35                  40                  45

Arg Phe Arg His Leu Arg Ser Lys Val Thr Asn Phe Phe Val Ile Ser
50                  55                  60

Leu Ala Val Ser Asp Leu Leu Val Ala Val Leu Val Met Pro Trp Lys
65                  70                  75                  80

Ala Val Ala Glu Ile Ala Gly Phe Trp Pro Phe Gly Ser Phe Cys Asn
                85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Gln Tyr Glu Arg Lys Met Thr Pro Lys Ala Ala Phe Ile Leu Ile Ser
    130                 135                 140

Val Ala Trp Thr Leu Ser Val Leu Ile Ser Phe Ile Pro Val Gln Leu
145                 150                 155                 160
```

-continued

```
Ser Trp His Lys Ala Lys Pro Thr Trp Pro Leu Asp Gly Asn Phe Thr
                165                 170                 175

Ser Leu Glu Asp Thr Glu Asp Asn Cys Asp Thr Arg Leu Ser Arg
            180                 185                 190

Thr Tyr Ala Ile Ser Ser Leu Ile Ser Phe Tyr Ile Pro Val Ala
        195                 200                 205

Ile Met Ile Val Thr Tyr Thr Ser Ile Tyr Arg Ile Ala Gln Lys Gln
210                 215                 220

Ile Arg Arg Ile Ser Ala Leu Glu Arg Ala Ala Val His Ala Lys Asn
225                 230                 235                 240

Cys Gln Thr Thr Ala Gly Asn Gly Asn Pro Val Glu Cys Ala Gln Ser
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Ser Asn Cys Met Val Pro Phe Cys Gly Ser Glu Glu Thr Gln
290                 295                 300

Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Gln Lys Ala Phe Ser Thr Leu Leu Gly Cys Tyr Arg Leu Cys Ala
            340                 345                 350

Ala Ala Arg Gly Arg Thr Pro Pro Ser Leu Gly Pro Gln Asp Glu Ser
        355                 360                 365

Cys Thr Thr Ala Ser Ser Ser Leu Ala Lys Asp Thr Ser Ser
        370                 375                 380

<210> SEQ ID NO 6
<211> LENGTH: 451
<212> TYPE: PRT
<213> ORGANISM: Artificial Sequence
<220> FEATURE:
<223> OTHER INFORMATION: amino acid sequence of 5HT1AR-V2R chimera
      expressed from the pEArrB-1/5HT1AR vector

<400> SEQUENCE: 6

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Leu Gly Thr Leu Ile Phe
        35                  40                  45

Cys Ala Val Leu Gly Asn Ala Cys Val Val Ala Ala Ile Ala Leu Glu
    50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140
```

Val Asn Lys Arg Thr Pro Arg Arg Ala Ala Leu Ile Ser Leu Thr
145                 150                 155                 160

Trp Leu Ile Gly Phe Leu Ile Ser Ile Pro Pro Met Leu Gly Trp Arg
            165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
            195                 200                 205

Leu Leu Met Leu Val Leu Tyr Gly Arg Ile Phe Arg Ala Ala Arg Phe
210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
            245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
            275                 280                 285

Ala Leu Glu Val Ile Glu Val His Arg Val Gly Asn Ser Lys Glu His
290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
            325                 330                 335

Leu Ala Arg Glu Phe Lys Thr Val Lys Thr Leu Gly Ile Ile Met Gly
            340                 345                 350

Thr Phe Ile Leu Cys Trp Leu Pro Phe Phe Ile Val Ala Leu Val Leu
            355                 360                 365

Pro Phe Cys Glu Ser Ser Cys His Met Pro Thr Leu Leu Gly Ala Ile
            370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
            405                 410                 415

Cys Asn Phe Cys Ala Ala Ala Arg Gly Arg Thr Pro Pro Ser Leu Gly
            420                 425                 430

Pro Gln Asp Glu Ser Cys Thr Thr Ala Ser Ser Ser Leu Ala Lys Asp
            435                 440                 445

Thr Ser Ser
    450

<210> SEQ ID NO 7
<211> LENGTH: 394
<212> TYPE: PRT
<213> ORGANISM: Artificial Sequence
<220> FEATURE:
<223> OTHER INFORMATION: amino acid sequence of beta3AR-V2R chimera
      expressed from pEArrB-1/beta3AR vector

<400> SEQUENCE: 7

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
            20                  25                  30

Val Pro Trp Glu Ala Ala Leu Ala Gly Ala Leu Leu Ala Leu Ala Val

```
                    35                  40                  45
Leu Ala Thr Val Gly Gly Asn Leu Leu Val Ile Val Ala Ile Ala Trp
 50                  55                  60

Thr Pro Arg Leu Gln Thr Met Thr Asn Val Phe Val Thr Ser Leu Ala
 65                  70                  75                  80

Ala Ala Asp Leu Val Met Gly Leu Leu Val Val Pro Ala Ala Thr
                     85                  90                  95

Leu Ala Leu Thr Gly His Trp Pro Leu Gly Ala Thr Gly Cys Glu Leu
                    100                 105                 110

Trp Thr Ser Val Asp Val Leu Cys Val Thr Ala Ser Ile Glu Thr Leu
                    115                 120                 125

Cys Ala Leu Ala Val Asp Arg Tyr Leu Ala Val Thr Asn Pro Leu Arg
                    130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                    165                 170                 175

Trp Trp Arg Val Gly Ala Asp Ala Glu Ala Gln Arg Cys His Ser Asn
                    180                 185                 190

Pro Arg Cys Cys Ala Phe Ala Ser Asn Met Pro Tyr Val Leu Leu Ser
                    195                 200                 205

Ser Ser Val Ser Phe Tyr Leu Pro Leu Leu Val Met Leu Phe Val Tyr
                    210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Ser Pro Ala Pro Ser Arg
                    245                 250                 255

Ser Leu Ala Pro Ala Pro Val Gly Thr Cys Ala Pro Glu Gly Val
                    260                 265                 270

Pro Ala Cys Gly Arg Arg Pro Ala Arg Leu Leu Pro Leu Arg Glu His
                    275                 280                 285

Arg Ala Leu Cys Thr Leu Gly Leu Ile Met Gly Thr Phe Thr Leu Cys
                    290                 295                 300

Trp Leu Pro Phe Phe Leu Ala Asn Val Leu Arg Ala Leu Gly Pro
305                 310                 315                 320

Ser Leu Val Pro Gly Pro Ala Phe Leu Ala Leu Asn Trp Leu Gly Tyr
                    325                 330                 335

Ala Asn Ser Ala Phe Asn Pro Leu Ile Tyr Cys Arg Ser Pro Asp Phe
                    340                 345                 350

Arg Ser Ala Phe Arg Arg Leu Leu Cys Arg Cys Ala Ala Ala Arg Gly
                    355                 360                 365

Arg Thr Pro Pro Ser Leu Gly Pro Gln Asp Glu Ser Cys Thr Thr Ala
                    370                 375                 380

Ser Ser Ser Leu Ala Lys Asp Thr Ser Ser
385                 390
```

<210> SEQ ID NO 8
<211> LENGTH: 362
<212> TYPE: PRT
<213> ORGANISM: Artificial Sequence
<220> FEATURE:
<223> OTHER INFORMATION: amino acid sequence of Edg1R-V2R chimera
      expressed from pEArrB-1/Edg1R vector

<400> SEQUENCE: 8

```
Met Gly Pro Thr Ser Val Pro Leu Val Lys Ala His Arg Ser Ser Val
 1               5                  10                  15

Ser Asp Tyr Val Asn Tyr Asp Ile Ile Val Arg His Tyr Asn Tyr Thr
             20                  25                  30

Gly Lys Leu Asn Ile Ser Ala Asp Lys Glu Asn Ser Ile Lys Leu Thr
         35                  40                  45

Ser Val Val Phe Ile Leu Ile Cys Cys Phe Ile Ile Leu Glu Asn Ile
 50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
                 85                  90                  95

Ala Tyr Thr Ala Asn Leu Leu Leu Ser Gly Ala Thr Thr Tyr Lys Leu
             100                 105                 110

Thr Pro Ala Gln Trp Phe Leu Arg Glu Gly Ser Met Phe Val Ala Leu
             115                 120                 125

Ser Ala Ser Val Phe Ser Leu Leu Ala Ile Ala Ile Glu Arg Tyr Ile
     130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                 165                 170                 175

Leu Pro Ile Met Gly Trp Asn Cys Ile Ser Ala Leu Ser Ser Cys Ser
             180                 185                 190

Thr Val Leu Pro Leu Tyr His Lys His Tyr Ile Leu Phe Cys Thr Thr
         195                 200                 205

Val Phe Thr Leu Leu Leu Ser Ile Val Ile Leu Tyr Cys Arg Ile
 210                 215                 220

Tyr Ser Leu Val Arg Thr Arg Ser Arg Leu Thr Phe Arg Lys Asn
225                 230                 235                 240

Ile Ser Lys Ala Ser Arg Ser Ser Glu Lys Ser Leu Ala Leu Leu Lys
             245                 250                 255

Thr Val Ile Ile Val Leu Ser Val Phe Ile Ala Cys Trp Ala Pro Leu
             260                 265                 270

Phe Ile Leu Leu Leu Leu Asp Val Gly Cys Lys Val Lys Thr Cys Asp
             275                 280                 285

Ile Leu Phe Arg Ala Glu Tyr Phe Leu Val Leu Ala Val Leu Asn Ser
 290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Ala Ala Ala Arg Gly
                 325                 330                 335

Arg Thr Pro Pro Ser Leu Gly Pro Gln Asp Glu Ser Cys Thr Thr Ala
             340                 345                 350

Ser Ser Ser Leu Ala Lys Asp Thr Ser Ser
         355                 360
```

<210> SEQ ID NO 9
<211> LENGTH: 1113
<212> TYPE: DNA
<213> ORGANISM: Artificial Sequence
<220> FEATURE:
<223> OTHER INFORMATION: nucleotide sequence of beta2AR-V2R chimera

<400> SEQUENCE: 9

-continued

```
atggggcaac ccgggaacgg cagcgccttc ttgctggcac ccaatagaag ccatgcgccg      60
gaccacgacg tcacgcagca aagggacgag gtgtgggtgg tgggcatggg catcgtcatg     120
tctctcatcg tcctggccat cgtgtttggc aatgtgctgg tcatcacagc cattgccaag     180
ttcgagcgtc tgcagacggt caccaactac ttcatcactt cactggcctg tgctgatctg     240
gtcatgggcc tggcagtggt gccctttggg gccgcccata ttcttatgaa aatgtggact     300
tttggcaact tctggtgcga gttttggact tccattgatg tgctgtgcgt cacggccagc     360
attgagaccc tgtgcgtgat cgcagtggat cgctactttg ccattacttc acctttcaag     420
taccagagcc tgctgaccaa gaataaggcc cgggtgatca ttctgatggt gtggattgtg     480
tcaggcctta cctccttctt gcccattcag atgcactggt accgggccac ccaccaggaa     540
gccatcaact gctatgccaa tgagacctgc tgtgacttct tcacgaacca agcctatgcc     600
attgcctctt ccatcgtgtc cttctacgtt cccctggtga tcatggtctt cgtctactcc     660
agggtctttc aggaggccaa aaggcagctc cagaagattg acaaatctga gggccgcttc     720
catgtccaga accttagcca ggtggagcag gatgggcgga cggggcatgg actccgcaga     780
tcttccaagt tctgcttgaa ggagcacaaa gccctcaaga cgttaggcat catcatgggc     840
actttcaccc tctgctggct gcccttcttc atcgttaaca ttgtgcatgt gatccaggat     900
aacctcatcc gtaaggaagt ttacatcctc ctaaattgga taggctatgt caattctggt     960
ttcaatcccc ttatctactg ccggagccca gatttcagga ttgccttcca ggagcttctg    1020
tgcgcccggg gacgcacccc acccagcctg ggtccccaag atgagtcctg caccaccgcc    1080
agctcctccc tggccaagga cacttcatcg tga                                 1113
```

```
<210> SEQ ID NO 10
<211> LENGTH: 1149
<212> TYPE: DNA
<213> ORGANISM: Artificial Sequence
<220> FEATURE:
<223> OTHER INFORMATION: nucleotide sequence of MOR-V2R chimera

<400> SEQUENCE: 10
atggacagca gcaccggccc agggaacacc agcgactgct cagacccctt agctcaggca      60
agttgctccc cagcacctgg ctcctggctc aacttgtccc acgttgatgg caaccagtcc     120
gatccatgcg gtctgaaccg caccgggctt ggcgggaacg acagcctgtg ccctcagacc     180
ggcagccctt ccatggtcac agccattacc atcatggccc tctactctat cgtgtgtgta     240
gtgggcctct tcggaaactt cctggtcatg tatgtgattg taagatacac caaaatgaag     300
actgccacca acatctacat tttcaacctt gctctggcag acgccttagc gaccagtaca     360
ctgccctttc agagtgtcaa ctacctgatg ggaacatggc ccttcggaac catcctctgc     420
aagatcgtga tctcaataga ttactacaac atgttcacca gcatattcac cctctgcacc     480
atgagcgtgg accgctacat tgctgtctgc cacccagtca aagccctgga tttccgtacc     540
ccccgaaatg ccaaaatcgt caacgtctgc aactggatcc tctcttctgc catcggtctg     600
cctgtaatgt tcatggcaac cacaaaatac aggcaggggt ccatagattg caccctcacg     660
ttctcccacc caacctggta ctgggagaac ctgctcaaaa tctgtgtctt tatcttcgct     720
ttcatcatgc cgatcctcat catcactgtg tgttacggcc tgatgatctt acgactcaag     780
agcgttcgca tgctatcggg ctccaaagaa aaggacagga atctgcgcag gatcacccgg     840
atggtgctgg tggtcgtggc tgtatttatc gtctgctgga cccccatcca catctacgtc     900
atcatcaaag cgctgatcac gattccagaa accacatttc agaccgtttc ctggcacttc     960
```

```
tgcattgctt tgggttacac gaacagctgc ctgaatccag ttctttacgc cttcctggat   1020
gaaaacttca agcgatgctt cagagagttc tgcgcggccg cacggggacg caccccaccc   1080
agcctgggtc cccaagatga gtcctgcacc accgccagct cctccctggc caaggacact   1140
tcatcgtga                                                            1149

<210> SEQ ID NO 11
<211> LENGTH: 1148
<212> TYPE: DNA
<213> ORGANISM: Artificial Sequence
<220> FEATURE:
<223> OTHER INFORMATION: nucleotide sequence of D1AR-V2R chimera

<400> SEQUENCE: 11
atggctccta acacttctac catggatgag gccgggctgc cagcggagag ggatttctcc     60
tttcgcatcc tcacggcctg tttcctgtca ctgctcatcc tgtccactct cctgggcaat   120
acccttgtct gtgcggccgt catccggttt cgacacctga ggtccaaggt gaccaacttc   180
tttgtcatct ctttagctgt gtcagatctc ttggtggctg tcctggtcat gcccctggaaa  240 gctgtggccg agattgctgg cttttggccc tttgggtcct tttgtaacat ctgggtagcc   300
tttgacatca tgtgctctac ggcgtccatt ctgaacctct gcgtgatcag cgtggacagg   360
tactgggcta tctccagccc tttccagtat gagaggaaga tgacccccaa agcagccttc   420
atcctgatta gcgtagcatg gactctgtct gtccttatat ccttcatccc agtacagcta   480
agctggcaca aggcaaagcc cacatggccc ttggatggca attttacctc cctggaggac   540
accgaggatg acaactgtga cacaaggttg agcaggacgt atgccatttc atcgtccctc   600
atcagctttt acatccccgt agccattatg atcgtcacct acaccagtat ctacaggatt   660
gcccagaagc aaaccggcgc atctcagcct tggagagggc agcagtccat gccaagaatt   720
gccagaccac gcaggtaac gggaacccccg tcgaatgcgc ccagtctgaa agttcctta    780 agatgtcctt caagagggag acgaaagttc taaagacgct gtctgtgatc atggggtgt   840 ttgtgtgctg ctggctccct ttcttcatct cgaactgtat ggtgcccttc gtggctctg    900 aggagaccca gccattctgc atcgattcca tcaccttcga tgtgtttgtg tggtttgggt   960
gggcgaattc ttccctgaac cccattattt atgcttttaa tgctgacttc cagaaggcgt   1020
tctcaaccct cttaggatgc tacagactct gcgcggccgc acggggacgc accccaccca   1080
gcctgggtcc ccaagatgag tcctgcacca ccgccagctc ctccctggcc aaggacactt   1140
catcgtga                                                             1148

<210> SEQ ID NO 12
<211> LENGTH: 1356
<212> TYPE: DNA
<213> ORGANISM: Artificial Sequence
<220> FEATURE:
<223> OTHER INFORMATION: nucleotide sequence of 5HT1AR-V2R chimera

<400> SEQUENCE: 12
atggatgtgc tcagccctgg tcagggcaac aacaccacat caccaccggc tccctttgag    60
accggcggca acactactgg tatctccgac gtgaccgtca gctaccaagt gatcacctct   120
ctgctgctgg gcacgctcat cttctgcgcg gtgctgggca atgcgtgcgt ggtggctgcc   180
atcgccttgg agcgctccct gcagaacgtg gccaattatc ttattggctc tttggcggtc   240
accgacctca tggtgtcggt gttggtgctg cccatggccg cgctgtatca ggtgctcaac   300
```

-continued

| | |
|---|---|
| aagtggacac tgggccaggt aacctgcgac ctgttcatcg ccctcgacgt gctgtgctgc | 360 |
| acctcatcca tcttgcacct gtgcgccatc gcgctggaca ggtactgggc catcacggac | 420 |
| cccatcgact acgtgaacaa gaggacgccc cggcgcgccg ctgcgctcat ctcgctcact | 480 |
| tggcttattg gcttcctcat ctctatcccg cccatgctgg gctggcgcac cccggaagac | 540 |
| cgctcggacc ccgacgcatg caccattagc aaggatcatg gctacactat ctattccacc | 600 |
| tttggagctt tctacatccc gctgctgctc atgctggttc tctatggcg catattccga | 660 |
| gctgcgcgct tccgcatccg caagacggtc aaaaaggtgg agaagaccgg agcggacacc | 720 |
| cgccatggag catctcccgc cccgcagccc aagaagagtg tgaatggaga gtcggggagc | 780 |
| aggaactgga ggctgggcgt ggagagcaag gctgggggtg ctctgtgcgc caatggcgcg | 840 |
| gtgaggcaag gtgacgatgg cgccgccctg gaggtgatcg aggtgcaccg agtgggcaac | 900 |
| tccaaagagc acttgcctct gcccagcgag gctggtccta ccccttgtgc cccgcctct | 960 |
| ttcgagagga aaaatgagcg caacgccgag gcgaagcgca agatggccct ggcccgagag | 1020 |
| aggaagacag tgaagacgct gggcatcatc atgggcacct tcatcctctg ctggctgccc | 1080 |
| ttcttcatcg tggctcttgt tctgcccttc tgcgagagca gctgccacat gcccaccctg | 1140 |
| ttgggcgcca taatcaattg gctgggctac tccaactctc tgcttaaccc cgtcatttac | 1200 |
| gcatacttca acaaggactt tcaaaacgcg tttaagaaga tcattaagtg taacttctgc | 1260 |
| gcggccgcac ggggacgcac cccacccagc ctgggtcccc aagatgagtc ctgcaccacc | 1320 |
| gccagctcct ccctggccaa ggacacttca tcgtga | 1356 |

<210> SEQ ID NO 13
<211> LENGTH: 1185
<212> TYPE: DNA
<213> ORGANISM: Artificial Sequence
<220> FEATURE:
<223> OTHER INFORMATION: nucleotide sequence of beta3-AR-V2R chimera

<400> SEQUENCE: 13

| | |
|---|---|
| atggctccgt ggcctcacga gaacagctct cttgccccat ggccggacct ccccacgctg | 60 |
| gcgcccaata ccgccaacac cagtgggctg ccaggggttc cgtgggaggc ggccctagcc | 120 |
| ggggccctgc tggcgctggc ggtgctggcc accgtgggag gcaacctgct ggtcatcgtg | 180 |
| gccatcgcct ggactccgag actccagacc atgaccaacg tgttcgtgac ttcgctggcc | 240 |
| gcagccgacc tggtgatggg actcctggtg gtgccgccgg cggccacctt ggcgctgact | 300 |
| ggccactggc cgttgggcgc cactggctgc gagctgtgga cctcggtgga cgtgctgtgt | 360 |
| gtgaccgcca gcatcgaaac cctgtgcgcc ctggccgtgg accgctacct ggctgtgacc | 420 |
| aacccgctgc gttacggcgc actggtcacc aagcgctgcg cccggacagc tgtggtcctg | 480 |
| gtgtgggtcg tgtcggccgc ggtgtcgttt gcgcccatca tgagccagtg gtggcgcgta | 540 |
| ggggccgacg ccgaggcgca cgcgctgcac tccaacccgc gctgctgtgc cttcgcctcc | 600 |
| aacatgcct acgtgctgct gtcctcctcc gtctccttct accttcctct tctcgtgatg | 660 |
| ctcttcgtct acgcgcgggt tttcgtggtg gctacgcgcc agctgcgctt gctgcgcggg | 720 |
| gagctgggcc gctttccgcc cgaggagtct ccgccggcgc cgtcgcgctc tctggccccg | 780 |
| gccccggtgg ggacgtgcgc tccgcccgaa gggtgcccg cctgcggccg gcggcccgcg | 840 |
| cgcctcctgc ctctccggga acaccggggc ctgtgcacct gggtctcat catgggcacc | 900 |
| ttcactctct gctggttgcc cttctttctg gccaacgtgc tgcgcgccct gggggcccc | 960 |
| tctctagtcc cgggcccggc tttccttgcc ctgaactggc taggttatgc caattctgcc | 1020 |

```
ttcaacccgc tcatctactg ccgcagcccg gactttcgca gcgccttccg ccgtcttctg    1080
tgccgctgcg cggccgcacg gggacgcacc ccacccagcc tgggtcccca agatgagtcc    1140
tgcaccaccg ccagctcctc cctggccaag gacacttcat cgtga                   1185

<210> SEQ ID NO 14
<211> LENGTH: 1089
<212> TYPE: DNA
<213> ORGANISM: Artificial Sequence
<220> FEATURE:
<223> OTHER INFORMATION: nucleotide sequence of Edg1-V2R chimera

<400> SEQUENCE: 14
atggggccca ccagcgtccc gctggtcaag gcccaccgca gctcggtctc tgactacgtc      60
aactatgata tcatcgtccg gcattacaac tacacgggaa agctgaatat cagcgcggac     120
aaggagaaca gcattaaact gacctcggtg gtgttcattc tcatctgctg ctttatcatc     180
ctggagaaca tctttgtctt gctgaccatt tggaaaacca agaaattcca ccgacccatg     240
tactatttta ttggcaatct ggccctctca gacctgttgg caggagtagc ctacacagct     300
aacctgctct tgtctggggc caccacctac aagctcactc ccgcccagtg gtttctgcgg     360
gaagggagta tgtttgtggc cctgtcagcc tccgtgttca gtctcctcgc catcgccatt     420
gagcgctata tcacaatgct gaaaatgaaa ctccacaacg ggagcaataa cttccgcctc     480
ttcctgctaa tcagcgcctg ctgggtcatc tccctcatcc tgggtggcct gcctatcatg     540
ggctggaact gcatcagtgc gctgtccagc tgctccaccg tgctgccgct ctaccacaag     600
cactatatcc tcttctgcac cacggtcttc actctgcttc tgctctccat cgtcattctg     660
tactgcagaa tctactcctt ggtcaggact cggagccgcc gcctgacgtt ccgcaagaac     720
atttccaagg ccagccgcag ctctgagaag tcgctggcgc tgctcaagac cgtaattatc     780
gtcctgagcg tcttcatcgc ctgctgggca ccgctcttca cctgctcct gctggatgtg     840 ggctgcaagg tgaagacctg tgacatcctc ttcagagcgg agtacttcct ggtgttagct     900
gtgctcaact ccgcaccaa ccccatcatt tacactctga ccaacaagga gatgcgtcgg     960
gccttcatcc ggatcatgtc ctgctgcaag tgcgcggccg cacggggacg caccccaccc    1020
agcctgggtc cccaagatga gtcctgcacc accgccagct cctccctggc caaggacact    1080
tcatcgtga                                                           1089

<210> SEQ ID NO 15
<211> LENGTH: 43
<212> TYPE: PRT
<213> ORGANISM: Homo sapiens

<400> SEQUENCE: 15

Asn Pro Ile Val Tyr Ala Phe Arg Ile Gln Lys Phe Arg Val Thr Phe
 1               5                  10                  15

Leu Lys Ile Trp Asn Asp His Phe Arg Cys Gln Pro Ala Pro Pro Ile
             20                  25                  30

Asp Glu Asp Leu Pro Glu Glu Arg Pro Asp Asp
         35                  40

<210> SEQ ID NO 16
<211> LENGTH: 176
<212> TYPE: PRT
<213> ORGANISM: Homo sapiens

<400> SEQUENCE: 16
```

```
Asn Pro Ile Ile Tyr Pro Cys Ser Ser Lys Glu Phe Arg Ala Phe Val
 1               5                  10                  15

Arg Ile Leu Gly Cys Gln Cys Arg Gly Arg Gly Arg Arg Arg Arg Arg
             20                  25                  30

Arg Arg Arg Arg Leu Gly Gly Cys Ala Tyr Thr Tyr Arg Pro Trp Thr
         35                  40                  45

Arg Gly Gly Ser Leu Glu Arg Ser Gln Ser Arg Lys Asp Ser Leu Asp
     50                  55                  60

Asp Ser Gly Ser Cys Leu Ser Gly Ser Gln Arg Thr Leu Pro Ser Ala
65                  70                  75                  80

Ser Pro Ser Pro Gly Tyr Leu Gly Arg Gly Ala Pro Pro Val Glu
                 85                  90                  95

Leu Cys Ala Phe Pro Glu Trp Lys Ala Pro Gly Ala Leu Leu Ser Leu
            100                 105                 110

Pro Ala Pro Glu Pro Pro Gly Arg Arg Gly Arg His Asp Ser Gly Pro
            115                 120                 125

Leu Phe Thr Phe Lys Leu Leu Thr Glu Pro Glu Ser Pro Gly Thr Asp
    130                 135                 140

Gly Gly Ala Ser Asn Gly Gly Cys Glu Ala Ala Ala Asp Val Ala Asn
145                 150                 155                 160

Gly Gln Pro Gly Phe Lys Ser Asn Met Pro Leu Ala Pro Gly Gln Phe
                165                 170                 175

<210> SEQ ID NO 17
<211> LENGTH: 29
<212> TYPE: PRT
<213> ORGANISM: Homo sapiens

<400> SEQUENCE: 17

Asn Pro Val Ile Tyr Thr Ile Phe Asn His Asp Phe Arg Arg Ala Phe
 1               5                  10                  15

Lys Lys Ile Leu Cys Arg Gly Asp Arg Lys Arg Ile Val
             20                  25

<210> SEQ ID NO 18
<211> LENGTH: 29
<212> TYPE: PRT
<213> ORGANISM: Human

<400> SEQUENCE: 18

Asn Pro Val Ile Tyr Thr Ile Phe Asn Gln Asp Phe Arg Arg Ala Phe
 1               5                  10                  15

Arg Arg Ile Leu Cys Arg Pro Trp Thr Gln Thr Ala Trp
             20                  25

<210> SEQ ID NO 19
<211> LENGTH: 31
<212> TYPE: PRT
<213> ORGANISM: Human

<400> SEQUENCE: 19

Asn Pro Val Ile Tyr Thr Val Phe Asn Gln Asp Phe Arg Pro Ser Phe
 1               5                  10                  15

Lys His Ile Leu Phe Arg Arg Arg Arg Arg Gly Phe Arg Gln
             20                  25                  30

<210> SEQ ID NO 20
<211> LENGTH: 105
```

-continued

<212> TYPE: PRT
<213> ORGANISM: Homo sapiens

<400> SEQUENCE: 20

Asn Pro Ile Ile Tyr Cys Arg Ser Pro Asp Phe Arg Lys Ala Phe Gln
1               5                   10                  15

Gly Leu Leu Cys Cys Ala Arg Arg Ala Ala Arg Arg His Ala Thr
            20                  25                  30

His Gly Asp Arg Pro Arg Ala Ser Gly Cys Leu Ala Arg Pro Gly Pro
        35                  40                  45

Pro Pro Ser Pro Gly Ala Ala Ser Asp Asp Asp Asp Val Val
    50                  55                  60

Gly Ala Thr Pro Pro Ala Arg Leu Leu Glu Pro Trp Ala Gly Cys Asn
65                  70                  75                  80

Gly Gly Ala Ala Ala Asp Ser Asp Ser Ser Leu Asp Glu Pro Cys Arg
                85                  90                  95

Pro Gly Phe Ala Ser Glu Ser Lys Val
            100                 105

<210> SEQ ID NO 21
<211> LENGTH: 92
<212> TYPE: PRT
<213> ORGANISM: Homo sapiens

<400> SEQUENCE: 21

Asn Pro Leu Ile Tyr Cys Arg Ser Pro Asp Phe Arg Ile Ala Phe Gln
1               5                   10                  15

Glu Leu Leu Cys Leu Arg Arg Ser Ser Leu Lys Ala Tyr Gly Asn Gly
            20                  25                  30

Tyr Ser Ser Asn Gly Asn Thr Gly Glu Gln Ser Gly Tyr His Val Glu
        35                  40                  45

Gln Glu Lys Glu Asn Lys Leu Leu Cys Glu Asp Leu Pro Gly Thr Glu
    50                  55                  60

Asp Phe Val Gly His Gln Gly Thr Val Pro Ser Asp Asn Ile Asp Ser
65                  70                  75                  80

Gln Gly Arg Asn Cys Ser Thr Asn Asp Ser Leu Leu
                85                  90

<210> SEQ ID NO 22
<211> LENGTH: 120
<212> TYPE: PRT
<213> ORGANISM: Homo sapiens

<400> SEQUENCE: 22

Asn Pro Ile Ile Tyr Ala Phe Asn Ala Asp Phe Arg Lys Ala Phe Ser
1               5                   10                  15

Thr Leu Leu Gly Cys Tyr Arg Leu Cys Pro Ala Thr Asn Asn Ala Ile
            20                  25                  30

Glu Thr Val Ser Ile Asn Asn Asn Gly Ala Ala Met Phe Ser Ser His
        35                  40                  45

His Glu Pro Arg Gly Ser Ile Ser Lys Glu Cys Asn Leu Val Tyr Leu
    50                  55                  60

Ile Pro His Ala Val Gly Ser Ser Glu Asp Leu Lys Lys Glu Glu Ala
65                  70                  75                  80

Ala Gly Ile Ala Arg Pro Leu Glu Lys Leu Ser Pro Ala Leu Ser Val
                85                  90                  95

Ile Leu Asp Tyr Asp Thr Asp Val Ser Leu Glu Lys Ile Gln Pro Ile

```
            100                 105                 110
Thr Gln Asn Gly Gln His Pro Thr
        115                 120

<210> SEQ ID NO 23
<211> LENGTH: 22
<212> TYPE: PRT
<213> ORGANISM: Human

<400> SEQUENCE: 23

Asn Pro Ile Ile Tyr Thr Thr Phe Asn Ile Glu Phe Arg Lys Ala Phe
1               5                   10                  15

Leu Lys Ile Leu His Cys
            20

<210> SEQ ID NO 24
<211> LENGTH: 22
<212> TYPE: PRT
<213> ORGANISM: Human

<400> SEQUENCE: 24

Asn Pro Val Ile Tyr Thr Thr Phe Asn Ile Glu Phe Arg Lys Ala Phe
1               5                   10                  15

Leu Lys Ile Leu Ser Cys
            20

<210> SEQ ID NO 25
<211> LENGTH: 24
<212> TYPE: PRT
<213> ORGANISM: Human

<400> SEQUENCE: 25

Asn Pro Val Ile Tyr Thr Val Phe Asn Ala Glu Phe Arg Asn Val Phe
1               5                   10                  15

Arg Lys Ala Leu Arg Ala Cys Cys
            20

<210> SEQ ID NO 26
<211> LENGTH: 123
<212> TYPE: PRT
<213> ORGANISM: Human

<400> SEQUENCE: 26

Asn Pro Val Ile Tyr Ala Phe Asn Ala Asp Phe Gln Lys Val Phe Ala
1               5                   10                  15

Gln Leu Leu Gly Cys Ser His Phe Cys Ser Arg Thr Pro Val Glu Thr
            20                  25                  30

Val Asn Ile Ser Asn Glu Leu Ile Ser Tyr Asn Gln Asp Ile Val Phe
        35                  40                  45

His Lys Glu Ile Ala Ala Ala Tyr Ile His Met Met Pro Asn Ala Val
    50                  55                  60

Thr Pro Gly Asn Arg Glu Val Asp Asn Asp Glu Glu Gly Pro Phe
65                  70                  75                  80

Asp Arg Met Phe Gln Ile Tyr Gln Thr Ser Pro Asp Gly Asp Pro Val
                85                  90                  95

Ala Glu Ser Val Trp Glu Leu Asp Cys Glu Gly Glu Ile Ser Leu Asp
            100                 105                 110

Lys Ile Thr Pro Phe Thr Pro Asn Gly Phe His
        115                 120
```

-continued

<210> SEQ ID NO 27
<211> LENGTH: 47
<212> TYPE: PRT
<213> ORGANISM: Homo sapiens

<400> SEQUENCE: 27

Asn Pro Met Cys Tyr Ala Leu Cys Asn Lys Ala Phe Arg Asp Thr Phe
1               5                   10                  15

Arg Leu Leu Leu Leu Cys Arg Trp Asp Lys Arg Trp Arg Lys Ile
            20                  25                  30

Pro Lys Arg Pro Gly Ser Val His Arg Thr Pro Ser Arg Gln Cys
        35                  40                  45

<210> SEQ ID NO 28
<211> LENGTH: 31
<212> TYPE: PRT
<213> ORGANISM: Homo sapiens

<400> SEQUENCE: 28

Asn Pro Ala Cys Tyr Ala Leu Cys Asn Ala Thr Phe Lys Lys Thr Phe
1               5                   10                  15

Lys His Leu Leu Met Cys His Tyr Lys Asn Ile Gly Ala Thr Arg
            20                  25                  30

<210> SEQ ID NO 29
<211> LENGTH: 51
<212> TYPE: PRT
<213> ORGANISM: Homo sapiens

<400> SEQUENCE: 29

Asn Pro Val Cys Tyr Ala Leu Cys Asn Lys Thr Phe Arg Thr Thr Phe
1               5                   10                  15

Lys Met Leu Leu Leu Cys Gln Cys Asp Lys Lys Arg Arg Lys Gln
            20                  25                  30

Gln Tyr Gln Gln Arg Gln Ser Val Ile Phe His Lys Arg Ala Pro Glu
        35                  40                  45

Gln Ala Leu
        50

<210> SEQ ID NO 30
<211> LENGTH: 31
<212> TYPE: PRT
<213> ORGANISM: Homo sapiens

<400> SEQUENCE: 30

Asn Pro Ala Cys Tyr Ala Leu Cys Asn Ala Thr Phe Lys Lys Thr Phe
1               5                   10                  15

Arg His Leu Leu Leu Cys Gln Tyr Arg Asn Ile Gly Thr Ala Arg
            20                  25                  30

<210> SEQ ID NO 31
<211> LENGTH: 42
<212> TYPE: PRT
<213> ORGANISM: Artificial Sequence
<220> FEATURE:
<223> OTHER INFORMATION: m5 muscarinic receptor

<400> SEQUENCE: 31

Asn Pro Ile Cys Tyr Ala Leu Cys Asn Arg Thr Phe Arg Lys Thr Phe
1               5                   10                  15

Lys Met Leu Leu Leu Cys Arg Trp Lys Lys Lys Lys Val Glu Glu Lys

```
                    20                  25                  30

Leu Tyr Trp Gln Gly Asn Ser Lys Leu Pro
        35                  40

<210> SEQ ID NO 32
<211> LENGTH: 24
<212> TYPE: PRT
<213> ORGANISM: Homo sapiens

<400> SEQUENCE: 32

Asn Pro Val Ile Tyr Ala Tyr Phe Asn Lys Asp Phe Gln Asn Ala Phe
1               5                   10                  15

Lys Lys Ile Ile Lys Cys Lys Phe
            20

<210> SEQ ID NO 33
<211> LENGTH: 26
<212> TYPE: PRT
<213> ORGANISM: Homo sapiens

<400> SEQUENCE: 33

Asn Pro Ile Ile Tyr Thr Met Ser Asn Glu Asp Phe Lys Gln Ala Phe
1               5                   10                  15

His Lys Leu Ile Arg Phe Lys Cys Thr Ser
            20                  25

<210> SEQ ID NO 34
<211> LENGTH: 24
<212> TYPE: PRT
<213> ORGANISM: Homo sapiens

<400> SEQUENCE: 34

Asn Pro Leu Leu Tyr Thr Ser Phe Asn Glu Asp Phe Lys Leu Ala Phe
1               5                   10                  15

Lys Lys Leu Ile Arg Cys Arg Glu
            20

<210> SEQ ID NO 35
<211> LENGTH: 37
<212> TYPE: PRT
<213> ORGANISM: Artificial Sequence
<220> FEATURE:
<223> OTHER INFORMATION: olfactory receptor 6A1

<400> SEQUENCE: 35

Asn Pro Ile Ile Tyr Cys Leu Arg Asn Gln Glu Val Lys Arg Ala Leu
1               5                   10                  15

Cys Cys Ile Leu His Leu Tyr Gln His Gln Asp Pro Asp Pro Lys Lys
            20                  25                  30

Gly Ser Arg Asn Val
        35

<210> SEQ ID NO 36
<211> LENGTH: 27
<212> TYPE: PRT
<213> ORGANISM: Artificial Sequence
<220> FEATURE:
<223> OTHER INFORMATION: olfactory receptor 2C1

<400> SEQUENCE: 36

Asn Pro Leu Ile Tyr Thr Leu Arg Asn Met Glu Val Lys Gly Ala Leu
1               5                   10                  15
```

```
Arg Arg Leu Leu Gly Lys Gly Arg Glu Val Gly
            20                  25

<210> SEQ ID NO 37
<211> LENGTH: 62
<212> TYPE: PRT
<213> ORGANISM: Homo sapiens

<400> SEQUENCE: 37

Asn Pro Leu Phe Tyr Gly Phe Leu Gly Lys Lys Phe Lys Arg Tyr Phe
1               5                   10                  15

Leu Gln Leu Leu Lys Tyr Ile Pro Pro Lys Ala Lys Ser His Ser Asn
            20                  25                  30

Leu Ser Thr Lys Met Ser Thr Leu Ser Tyr Arg Pro Ser Asp Asn Val
        35                  40                  45

Ser Ser Ser Thr Lys Lys Pro Ala Pro Cys Phe Glu Val Glu
    50                  55                  60

<210> SEQ ID NO 38
<211> LENGTH: 50
<212> TYPE: PRT
<213> ORGANISM: Homo sapiens

<400> SEQUENCE: 38

Asn Pro Phe Leu Tyr Cys Phe Val Gly Asn Arg Phe Gln Gln Lys Leu
1               5                   10                  15

Arg Ser Val Phe Arg Val Pro Ile Thr Trp Leu Gln Gly Lys Arg Glu
            20                  25                  30

Ser Met Ser Cys Arg Lys Ser Ser Ser Leu Arg Glu Met Glu Thr Phe
        35                  40                  45

Val Ser
    50

<210> SEQ ID NO 39
<211> LENGTH: 51
<212> TYPE: PRT
<213> ORGANISM: Homo sapiens

<400> SEQUENCE: 39

Asn Pro Leu Ile Tyr Ala Phe Ile Gly Gln Lys Phe Arg His Gly Leu
1               5                   10                  15

Leu Lys Ile Leu Ala Ile His Gly Leu Ile Ser Lys Asp Ser Leu Pro
            20                  25                  30

Lys Asp Ser Arg Pro Ser Phe Val Gly Ser Ser Ser Gly His Thr Ser
        35                  40                  45

Thr Thr Leu
    50

<210> SEQ ID NO 40
<211> LENGTH: 67
<212> TYPE: PRT
<213> ORGANISM: Artificial Sequence
<220> FEATURE:
<223> OTHER INFORMATION: cx3c chemokine receptor 1 (cx3cr1) (fractalkine
      receptor)

<400> SEQUENCE: 40

Asn Pro Leu Ile Tyr Ala Phe Ala Gly Glu Lys Phe Arg Arg Tyr Leu
1               5                   10                  15

Tyr His Leu Tyr Gly Lys Cys Leu Ala Val Leu Cys Gly Arg Ser Val
            20                  25                  30
```

```
His Val Asp Phe Ser Ser Glu Ser Gln Arg Ser Arg His Gly Ser
            35                  40                  45

Val Leu Ser Ser Asn Phe Thr Tyr His Thr Ser Asp Gly Asp Ala Leu
        50                  55                  60

Leu Leu Leu
65

<210> SEQ ID NO 41
<211> LENGTH: 59
<212> TYPE: PRT
<213> ORGANISM: Human

<400> SEQUENCE: 41

Asn Pro Ile Leu Tyr Asn Leu Val Ser Ala Asn Phe Arg His Ile Phe
1               5                   10                  15

Leu Ala Thr Leu Ala Cys Leu Cys Pro Val Trp Arg Arg Arg Arg Lys
            20                  25                  30

Arg Pro Ala Phe Ser Arg Lys Ala Asp Ser Val Ser Ser Asn His Thr
        35                  40                  45

Leu Ser Ser Asn Ala Thr Arg Glu Thr Leu Tyr
    50                  55

<210> SEQ ID NO 42
<211> LENGTH: 107
<212> TYPE: PRT
<213> ORGANISM: Artificial Sequence
<220> FEATURE:
<223> OTHER INFORMATION: substance-P receptor (SPR) (NK-1 receptor)
      (NK-1R)

<400> SEQUENCE: 42

Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
            20                  25                  30

Gly Leu Glu Met Lys Ser Thr Arg Tyr Leu Gln Thr Gln Gly Ser Val
        35                  40                  45

Tyr Lys Val Ser Arg Leu Glu Thr Thr Ile Ser Thr Val Val Gly Ala
    50                  55                  60

His Glu Glu Glu Pro Glu Asp Gly Pro Lys Ala Thr Pro Ser Ser Leu
65                  70                  75                  80

Asp Leu Thr Ser Asn Cys Ser Ser Arg Ser Asp Ser Lys Thr Met Thr
                85                  90                  95

Glu Ser Phe Ser Phe Ser Ser Asn Val Leu Ser
            100                 105

<210> SEQ ID NO 43
<211> LENGTH: 50
<212> TYPE: PRT
<213> ORGANISM: Homo sapiens

<400> SEQUENCE: 43

Asn Pro Trp Ile Tyr Ala Ser Phe Ser Ser Val Ser Ser Glu Leu Arg
1               5                   10                  15

Ser Leu Leu Cys Cys Ala Arg Gly Arg Thr Pro Pro Ser Leu Gly Pro
            20                  25                  30

Gln Asp Glu Ser Cys Thr Thr Ala Ser Ser Ser Leu Ala Lys Asp Thr
        35                  40                  45
```

-continued

Ser Ser
    50

<210> SEQ ID NO 44
<211> LENGTH: 83
<212> TYPE: PRT
<213> ORGANISM: Human

<400> SEQUENCE: 44

Asn Pro Val Ile Tyr Asn Leu Met Ser Gln Lys Phe Arg Ala Ala Phe
1               5                   10                  15

Arg Lys Leu Cys Asn Cys Lys Gln Lys Pro Thr Glu Lys Pro Ala Asn
            20                  25                  30

Tyr Ser Val Ala Leu Asn Tyr Ser Val Ile Lys Glu Ser Asp His Phe
        35                  40                  45

Ser Thr Glu Leu Asp Asp Ile Thr Val Thr Asp Thr Tyr Leu Ser Ala
    50                  55                  60

Thr Lys Val Ser Phe Asp Asp Thr Cys Leu Ala Ser Glu Val Ser Phe
65                  70                  75                  80

Ser Gln Ser

<210> SEQ ID NO 45
<211> LENGTH: 65
<212> TYPE: PRT
<213> ORGANISM: Human

<400> SEQUENCE: 45

Asn Pro Trp Ile Tyr Met Leu Phe Thr Gly His Leu Phe His Glu Leu
1               5                   10                  15

Val Gln Arg Phe Leu Cys Cys Ser Ala Ser Tyr Leu Lys Gly Arg Arg
            20                  25                  30

Leu Gly Glu Thr Ser Ala Ser Lys Lys Ser Asn Ser Ser Ser Phe Val
        35                  40                  45

Leu Ser His Arg Ser Ser Ser Gln Arg Ser Cys Ser Gln Pro Ser Thr
    50                  55                  60

Ala
65

<210> SEQ ID NO 46
<211> LENGTH: 75
<212> TYPE: PRT
<213> ORGANISM: Homo sapiens

<400> SEQUENCE: 46

Asn Pro Val Leu Tyr Ser Leu Met Ser Ser Arg Phe Arg Glu Thr Phe
1               5                   10                  15

Gln Glu Ala Leu Cys Leu Gly Ala Cys Cys His Arg Leu Arg Pro Arg
            20                  25                  30

His Ser Ser His Ser Leu Ser Arg Met Thr Thr Gly Ser Thr Leu Cys
        35                  40                  45

Asp Val Gly Ser Leu Gly Ser Trp Val His Pro Leu Ala Gly Asn Asp
    50                  55                  60

Gly Pro Glu Ala Gln Gln Glu Thr Asp Pro Ser
65                  70                  75

<210> SEQ ID NO 47
<211> LENGTH: 62
<212> TYPE: PRT
<213> ORGANISM: Homo sapiens

```
<400> SEQUENCE: 47

Asn Pro Leu Val Tyr Cys Phe Met His Arg Phe Arg Gln Ala Cys
1               5                  10                  15

Leu Glu Thr Cys Ala Arg Cys Cys Pro Arg Pro Arg Ala Arg Pro
            20                  25                  30

Arg Ala Leu Pro Asp Glu Asp Pro Thr Pro Ser Ile Ala Ser Leu
        35                  40                  45

Ser Arg Leu Ser Tyr Thr Thr Ile Ser Thr Leu Gly Pro Gly
    50                  55                  60

<210> SEQ ID NO 48
<211> LENGTH: 82
<212> TYPE: PRT
<213> ORGANISM: Homo sapiens

<400> SEQUENCE: 48

Asn Pro Leu Val Tyr Ala Leu Ala Ser Arg His Phe Arg Ala Arg Phe
1               5                  10                  15

Arg Arg Leu Trp Pro Cys Gly Arg Arg Arg His Arg Ala Arg Arg
            20                  25                  30

Ala Leu Arg Arg Val Arg Pro Ala Ser Ser Gly Pro Pro Gly Cys Pro
        35                  40                  45

Gly Asp Ala Arg Pro Ser Gly Arg Leu Leu Ala Gly Gly Gln Gly
    50                  55                  60

Pro Glu Pro Arg Glu Gly Pro Val His Gly Gly Glu Ala Ala Arg Gly
65                  70                  75                  80

Pro Glu

<210> SEQ ID NO 49
<211> LENGTH: 76
<212> TYPE: PRT
<213> ORGANISM: Human

<400> SEQUENCE: 49

Asn Pro Ile Ile Tyr Thr Leu Thr Asn Lys Glu Met Arg Arg Ala Phe
1               5                  10                  15

Ile Arg Ile Met Ser Cys Cys Lys Cys Pro Ser Gly Asp Ser Ala Gly
            20                  25                  30

Lys Phe Lys Arg Pro Ile Ile Ala Gly Met Glu Phe Ser Arg Ser Lys
        35                  40                  45

Ser Asp Asn Ser Ser His Pro Gln Lys Asp Glu Gly Asp Asn Pro Glu
    50                  55                  60

Thr Ile Met Ser Ser Gly Asn Val Asn Ser Ser Ser
65                  70                  75

<210> SEQ ID NO 50
<211> LENGTH: 80
<212> TYPE: PRT
<213> ORGANISM: Homo sapiens

<400> SEQUENCE: 50

Asn Pro Ile Ile Tyr Ala Leu Arg Ser Lys Asp Leu Arg His Ala Phe
1               5                  10                  15

Arg Ser Met Phe Pro Ser Cys Glu Gly Thr Ala Gln Pro Leu Asp Asn
            20                  25                  30

Ser Met Gly Asp Ser Asp Cys Leu His Lys His Ala Asn Asn Ala Ala
        35                  40                  45
```

```
Ser Val His Arg Ala Ala Glu Ser Cys Ile Lys Ser Thr Val Lys Ile
 50                  55                  60

Ala Lys Val Thr Met Ser Val Ser Thr Asp Thr Ser Ala Glu Ala Leu
 65                  70                  75                  80

<210> SEQ ID NO 51
<211> LENGTH: 59
<212> TYPE: PRT
<213> ORGANISM: Human

<400> SEQUENCE: 51

Asn Pro Val Leu Tyr Ala Phe Leu Asp Glu Asn Phe Lys Arg Cys Phe
 1               5                  10                  15

Arg Gln Leu Cys Arg Lys Pro Cys Gly Arg Pro Asp Pro Ser Ser Phe
             20                  25                  30

Ser Arg Pro Arg Glu Ala Thr Ala Arg Glu Arg Val Thr Ala Cys Thr
         35                  40                  45

Pro Ser Asp Gly Pro Gly Gly Arg Ala Ala
     50                  55

<210> SEQ ID NO 52
<211> LENGTH: 58
<212> TYPE: PRT
<213> ORGANISM: Human

<400> SEQUENCE: 52

Asp Pro Phe Val Tyr Tyr Phe Val Ser His Asp Phe Arg Asp His Ala
 1               5                  10                  15

Lys Asn Ala Leu Leu Cys Arg Ser Val Arg Thr Val Lys Gln Met Gln
             20                  25                  30

Val Ser Leu Thr Ser Lys Lys His Ser Arg Lys Ser Ser Ser Tyr Ser
         35                  40                  45

Ser Ser Ser Thr Thr Val Lys Thr Ser Tyr
     50                  55

<210> SEQ ID NO 53
<211> LENGTH: 66
<212> TYPE: PRT
<213> ORGANISM: Rat

<400> SEQUENCE: 53

Asn Gly Glu Val Gln Ala Glu Leu Arg Arg Lys Trp Arg Arg Trp His
 1               5                  10                  15

Leu Gln Gly Val Leu Gly Trp Ser Ser Lys Ser Gln His Pro Trp Gly
             20                  25                  30

Gly Ser Asn Gly Ala Thr Cys Ser Thr Gln Val Ser Met Leu Thr Arg
         35                  40                  45

Val Ser Pro Ser Ala Arg Arg Ser Ser Ser Phe Gln Ala Glu Val Ser
     50                  55                  60

Leu Val
 65

<210> SEQ ID NO 54
<211> LENGTH: 90
<212> TYPE: DNA
<213> ORGANISM: Human

<400> SEQUENCE: 54
gcccggggac gcaccccacc cagcctgggt ccccaagatg agtcctgcac caccgccagc    60
```

```
tcctccctgg ccaaggacac ttcatcgtga                                    90
```

<210> SEQ ID NO 55
<211> LENGTH: 114
<212> TYPE: DNA
<213> ORGANISM: Human

<400> SEQUENCE: 55

```
gcggccgcac ggggacgcac cccacccagc ctgggtcccc aagatgagtc ctgcaccacc   60
gccagctcct ccctggccaa ggacacttca tcgtgaagat ctccgcggtc taga        114
```

<210> SEQ ID NO 56
<211> LENGTH: 31
<212> TYPE: PRT
<213> ORGANISM: Artificial Sequence
<220> FEATURE:
<223> OTHER INFORMATION: carboxy terminus of modified GPCR

<400> SEQUENCE: 56

```
Ala Ala Ala Arg Gly Arg Thr Pro Pro Ser Leu Gly Pro Gln Asp Glu
 1               5                  10                  15

Ser Cys Thr Thr Ala Ser Ser Ser Leu Ala Lys Asp Thr Ser Ser
            20                  25                  30
```

<210> SEQ ID NO 57
<211> LENGTH: 30
<212> TYPE: PRT
<213> ORGANISM: Artificial Sequence
<220> FEATURE:
<223> OTHER INFORMATION: carboxyl-terminal tail of V2R

<400> SEQUENCE: 57

```
Cys Ala Arg Gly Arg Thr Pro Pro Ser Leu Gly Pro Gln Asp Glu Ser
 1               5                  10                  15

Cys Thr Thr Ala Ser Ser Ser Leu Ala Lys Asp Thr Ser Ser
            20                  25                  30
```

<210> SEQ ID NO 58
<211> LENGTH: 20
<212> TYPE: PRT
<213> ORGANISM: Artificial Sequence
<220> FEATURE:
<223> OTHER INFORMATION: V2R mutant receptor

<400> SEQUENCE: 58

```
Cys Ala Arg Gly Arg Thr Pro Pro Ser Leu Gly Pro Gln Asp Glu Ser
 1               5                  10                  15

Cys Thr Thr Ala
            20
```

<210> SEQ ID NO 59
<211> LENGTH: 30
<212> TYPE: PRT
<213> ORGANISM: Artificial Sequence
<220> FEATURE:
<223> OTHER INFORMATION: V2R mutant receptor

<400> SEQUENCE: 59

```
Cys Ala Arg Gly Arg Thr Pro Pro Ser Leu Gly Pro Gln Asp Glu Ser
 1               5                  10                  15

Cys Thr Thr Ala Ala Ala Ala Leu Ala Lys Asp Ala Ala Ala
            20                  25                  30
```

<210> SEQ ID NO 60
<211> LENGTH: 30
<212> TYPE: PRT
<213> ORGANISM: Artificial Sequence
<220> FEATURE:
<223> OTHER INFORMATION: V2R mutant receptor

<400> SEQUENCE: 60

Cys Ala Arg Gly Arg Thr Pro Pro Ser Leu Gly Pro Gln Asp Glu Ser
 1               5                  10                  15

Cys Thr Thr Ala Ser Ser Ser Leu Ala Lys Asp Ala Ala Ala
            20                  25                  30

<210> SEQ ID NO 61
<211> LENGTH: 30
<212> TYPE: PRT
<213> ORGANISM: Artificial Sequence
<220> FEATURE:
<223> OTHER INFORMATION: V2R mutant receptor

<400> SEQUENCE: 61

Cys Ala Arg Gly Arg Thr Pro Pro Ser Leu Gly Pro Gln Asp Glu Ser
 1               5                  10                  15

Cys Thr Thr Ala Ala Ala Ala Leu Ala Lys Asp Thr Ser Ser
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: beta-2AR mutant receptor

<400> SEQUENCE: 62

Cys Ala Arg Gly Arg Thr Pro Pro Ser Leu Gly Pro Gln Asp Glu Ser
 1               5                  10                  15

Cys Thr Thr Ala Ala Ala Ala Leu Ala Lys Asp Thr Ser Ser
            20                  25                  30

<210> SEQ ID NO 63
<211> LENGTH: 73
<212> TYPE: PRT
<213> ORGANISM: Artificial Sequence
<220> FEATURE:
<223> OTHER INFORMATION: carboxyl-terminal tail of beta-2AR

<400> SEQUENCE: 63

Cys Leu Arg Arg Ser Ser Leu Lys Ala Tyr Gly Asn Gly Tyr Ser Ser
 1               5                  10                  15

Asn Gly Asn Thr Gly Glu Gln Ser Gly Tyr His Val Glu Gln Glu Lys
            20                  25                  30

Glu Asn Lys Leu Leu Cys Glu Asp Leu Pro Gly Thr Glu Asp Phe Val
        35                  40                  45

Gly His Gln Gly Thr Val Pro Ser Asp Asn Ile Asp Ser Gln Gly Arg
    50                  55                  60

Asn Cys Ser Thr Asn Asp Ser Leu Leu
65                  70

<210> SEQ ID NO 64
<211> LENGTH: 83
<212> TYPE: PRT
<213> ORGANISM: Artificial Sequence
<220> FEATURE:

<223> OTHER INFORMATION: beta-2AR mutant receptor

<400> SEQUENCE: 64

Cys Leu Arg Arg Ser Ser Leu Lys Ala Tyr Gly Asn Gly Tyr Ser Ser
1               5                   10                  15

Asn Gly Asn Thr Gly Glu Gln Ser Gly Tyr His Val Glu Gln Glu Lys
            20                  25                  30

Glu Asn Lys Leu Leu Cys Glu Asp Leu Pro Gly Thr Glu Asp Phe Val
        35                  40                  45

Gly His Gln Gly Thr Val Pro Ser Asp Asn Ile Asp Ser Gln Gly Arg
    50                  55                  60

Asn Cys Ser Thr Asn Asp Ser Leu Leu Ser Ser Ser Leu Ala Lys Asp
65                  70                  75                  80

Thr Ser Ser

<210> SEQ ID NO 65
<211> LENGTH: 30
<212> TYPE: PRT
<213> ORGANISM: Artificial Sequence
<220> FEATURE:
<223> OTHER INFORMATION: beta-2AR mutant receptor

<400> SEQUENCE: 65

Cys Leu Arg Arg Ser Ser Leu Lys Ala Tyr Gly Asn Gly Tyr Ser Ser
1               5                   10                  15

Asn Gly Asn Thr Ser Ser Ser Leu Ala Lys Asp Thr Ser Ser
            20                  25                  30

<210> SEQ ID NO 66
<211> LENGTH: 51
<212> TYPE: PRT
<213> ORGANISM: Artificial Sequence
<220> FEATURE:
<223> OTHER INFORMATION: carboxyl-terminal tail of V2R

<400> SEQUENCE: 66

Asn Pro Trp Ile Tyr Ala Ser Phe Ser Ser Val Ser Ser Glu Leu
1               5                   10                  15

Arg Ser Leu Leu Cys Cys Ala Arg Gly Arg Thr Pro Pro Ser Leu Gly
            20                  25                  30

Pro Gln Asp Glu Ser Cys Thr Thr Ala Ser Ser Ser Leu Ala Lys Asp
        35                  40                  45

Thr Ser Ser
    50

<210> SEQ ID NO 67
<211> LENGTH: 51
<212> TYPE: PRT
<213> ORGANISM: Artificial Sequence
<220> FEATURE:
<223> OTHER INFORMATION: receptor mutant

<400> SEQUENCE: 67

Asn Pro Trp Ile Tyr Ala Ser Phe Ser Ser Val Ser Ser Glu Leu
1               5                   10                  15

Arg Ser Leu Leu Cys Cys Ala Arg Gly Arg Thr Pro Pro Ser Leu Gly
            20                  25                  30

Pro Gln Asp Glu Ser Cys Thr Thr Ala Ser Ala Ala Ala Ala Lys Asp
        35                  40                  45

Thr Ser Ser

-continued

```
                        50

<210> SEQ ID NO 68
<211> LENGTH: 52
<212> TYPE: PRT
<213> ORGANISM: Artificial Sequence
<220> FEATURE:
<223> OTHER INFORMATION: receptor mutant

<400> SEQUENCE: 68

Asn Pro Trp Ile Tyr Ala Ser Phe Ser Ser Val Ser Ser Glu Leu
  1               5                  10                  15

Arg Ser Leu Leu Cys Cys Ala Arg Gly Arg Thr Pro Pro Ser Leu Gly
             20                  25                  30

Pro Gln Asp Glu Ser Cys Thr Thr Ala Ser Ser Leu Ala Lys Asp
         35                  40                  45

Thr Ala Ala Ala
         50

<210> SEQ ID NO 69
<211> LENGTH: 60
<212> TYPE: PRT
<213> ORGANISM: Artificial Sequence
<220> FEATURE:
<223> OTHER INFORMATION: carboxyl-terminal tail of NTR-1

<400> SEQUENCE: 69

Asn Pro Ile Leu Tyr Asn Leu Val Ser Ala Asn Phe Arg Gln Val Phe
  1               5                  10                  15

Leu Ser Thr Leu Ala Cys Leu Cys Pro Gly Trp Arg His Arg Arg Lys
             20                  25                  30

Lys Arg Pro Thr Phe Ser Arg Lys Pro Asn Ser Met Ser Ser Asn His
         35                  40                  45

Ala Phe Ser Thr Ser Ala Thr Arg Glu Thr Leu Tyr
     50                  55                  60

<210> SEQ ID NO 70
<211> LENGTH: 60
<212> TYPE: PRT
<213> ORGANISM: Artificial Sequence
<220> FEATURE:
<223> OTHER INFORMATION: receptor mutant

<400> SEQUENCE: 70

Asn Pro Ile Leu Tyr Asn Leu Val Ser Ala Asn Phe Arg Gln Val Phe
  1               5                  10                  15

Leu Ser Thr Leu Ala Cys Leu Cys Pro Gly Trp Arg His Arg Arg Lys
             20                  25                  30

Lys Arg Pro Thr Phe Ser Arg Lys Pro Asn Ser Ala Ser Ala Ala His
         35                  40                  45

Ala Phe Ser Thr Ser Ala Thr Arg Glu Thr Leu Tyr
     50                  55                  60

<210> SEQ ID NO 71
<211> LENGTH: 60
<212> TYPE: PRT
<213> ORGANISM: Artificial Sequence
<220> FEATURE:
<223> OTHER INFORMATION: receptor mutant

<400> SEQUENCE: 71

Asn Pro Ile Leu Tyr Asn Leu Val Ser Ala Asn Phe Arg Gln Val Phe
```

```
                1               5                  10                 15
Leu Ser Thr Leu Ala Cys Leu Cys Pro Gly Trp Arg His Arg Arg Lys
                    20                  25                  30

Lys Arg Pro Thr Phe Ser Arg Lys Pro Asn Ser Met Ser Ser Asn His
            35                  40                  45

Ala Phe Ser Ala Ala Ala Thr Arg Glu Thr Leu Tyr
            50                  55                  60

<210> SEQ ID NO 72
<211> LENGTH: 65
<212> TYPE: PRT
<213> ORGANISM: Artificial Sequence
<220> FEATURE:
<223> OTHER INFORMATION: carboxyl-terminal tail of OTR

<400> SEQUENCE: 72

Asn Pro Trp Ile Tyr Met Leu Phe Thr Gly His Leu Phe His Glu Leu
  1               5                  10                  15

Val Gln Arg Phe Leu Cys Cys Ser Ala Ser Tyr Leu Lys Gly Arg Arg
                20                  25                  30

Leu Gly Glu Thr Ser Ala Ser Lys Lys Ser Asn Ser Ser Ser Phe Val
            35                  40                  45

Leu Ser His Arg Ser Ser Ser Gln Arg Ser Cys Ser Gln Pro Ser Thr
        50                  55                  60

Ala
65

<210> SEQ ID NO 73
<211> LENGTH: 65
<212> TYPE: PRT
<213> ORGANISM: Artificial Sequence
<220> FEATURE:
<223> OTHER INFORMATION: receptor mutant

<400> SEQUENCE: 73

Asn Pro Trp Ile Tyr Met Leu Phe Thr Gly His Leu Phe His Glu Leu
  1               5                  10                  15

Val Gln Arg Phe Leu Cys Cys Ser Ala Ser Tyr Leu Lys Gly Arg Ala
                20                  25                  30

Ala Ala Ala Thr Ser Ala Ser Lys Lys Ser Asn Ser Ser Ser Phe Val
            35                  40                  45

Leu Ser His Arg Ser Ser Ser Gln Arg Ser Cys Ser Gln Pro Ser Thr
        50                  55                  60

Ala
65

<210> SEQ ID NO 74
<211> LENGTH: 65
<212> TYPE: PRT
<213> ORGANISM: Artificial Sequence
<220> FEATURE:
<223> OTHER INFORMATION: receptor mutant

<400> SEQUENCE: 74

Asn Pro Trp Ile Tyr Met Leu Phe Thr Gly His Leu Phe His Glu Leu
  1               5                  10                  15

Val Gln Arg Phe Leu Cys Cys Ser Ala Ser Tyr Leu Lys Gly Arg Arg
                20                  25                  30

Leu Gly Glu Thr Ser Ala Ala Ala Ala Ser Asn Ser Ser Ser Phe Val
            35                  40                  45
```

Leu Ser His Arg Ser Ser Gln Arg Ser Cys Ser Gln Pro Ser Thr
        50                  55                  60

Ala
65

<210> SEQ ID NO 75
<211> LENGTH: 65
<212> TYPE: PRT
<213> ORGANISM: Artificial Sequence
<220> FEATURE:
<223> OTHER INFORMATION: receptor mutant

<400> SEQUENCE: 75

Asn Pro Trp Ile Tyr Met Leu Phe Thr Gly His Leu Phe His Glu Leu
1               5                   10                  15

Val Gln Arg Phe Leu Cys Cys Ser Ala Ser Tyr Leu Lys Gly Arg Arg
                20                  25                  30

Leu Gly Glu Thr Ser Ala Ser Lys Lys Ser Asn Ser Ser Ser Phe Val
            35                  40                  45

Leu Ser His Arg Ala Ala Ala Gln Arg Ser Cys Ser Gln Pro Ser Thr
        50                  55                  60

Ala
65

<210> SEQ ID NO 76
<211> LENGTH: 105
<212> TYPE: PRT
<213> ORGANISM: Artificial Sequence
<220> FEATURE:
<223> OTHER INFORMATION: carboxyl-terminal tail of SPR

<400> SEQUENCE: 76

Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
                20                  25                  30

Gly Leu Glu Met Lys Ser Thr Arg Tyr Leu Gln Thr Gln Gly Val Tyr
            35                  40                  45

Lys Val Ser Arg Leu Glu Thr Thr Ile Ser Thr Val Val Gly Ala His
        50                  55                  60

Glu Glu Glu Pro Glu Gly Pro Lys Ala Thr Pro Ser Ser Leu Lys Leu
65                  70                  75                  80

Thr Ser Asn Cys Ser Ser Arg Ser Asp Ser Lys Thr Met Thr Glu Ser
                85                  90                  95

Phe Ser Phe Ser Ser Asn Val Leu Ser
            100                 105

<210> SEQ ID NO 77
<211> LENGTH: 66
<212> TYPE: PRT
<213> ORGANISM: Artificial Sequence
<220> FEATURE:
<223> OTHER INFORMATION: receptor mutant

<400> SEQUENCE: 77

Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
                20                  25                  30

```
Gly Leu Glu Met Lys Ser Thr Arg Tyr Leu Gln Thr Gln Gly Val Tyr
        35                  40                  45
Lys Val Ser Arg Leu Glu Thr Thr Ile Ser Thr Val Val Gly Ala His
    50                  55                  60
Glu Glu
65
```

```
<210> SEQ ID NO 78
<211> LENGTH: 44
<212> TYPE: PRT
<213> ORGANISM: Artificial Sequence
<220> FEATURE:
<223> OTHER INFORMATION: receptor mutant

<400> SEQUENCE: 78

Asn Pro Ile Ile Tyr Cys Cys Leu Asn Asp Arg Phe Arg Leu Gly Phe
1               5                   10                  15
Lys His Ala Phe Arg Cys Cys Pro Phe Ile Ser Ala Gly Asp Tyr Glu
            20                  25                  30
Gly Leu Glu Met Lys Ser Thr Arg Tyr Leu Gln Thr
        35                  40
```

```
<210> SEQ ID NO 79
<211> LENGTH: 20
<212> TYPE: PRT
<213> ORGANISM: Artificial Sequence
<220> FEATURE:
<223> OTHER INFORMATION: receptor mutant

<400> SEQUENCE: 79

Asn Pro Ile Ile Tyr Cys Cys Leu Asn Asp Arg Phe Arg Leu Gly Phe
1               5                   10                  15
Lys His Ala Phe
            20
```

```
<210> SEQ ID NO 80
<211> LENGTH: 69
<212> TYPE: PRT
<213> ORGANISM: Artificial Sequence
<220> FEATURE:
<223> OTHER INFORMATION: receptor mutant

<400> SEQUENCE: 80

Asn Pro Ile Ile Tyr Cys Cys Leu Asn Asp Arg Phe Arg Leu Gly Phe
1               5                   10                  15
Lys His Ala Phe Arg Cys Cys Pro Phe Ile Ser Ala Gly Asp Tyr Glu
            20                  25                  30
Gly Leu Glu Met Lys Ser Thr Arg Tyr Leu Gln Thr Ala Ala Val Ala
        35                  40                  45
Ala Val Ser Arg Leu Glu Thr Thr Ile Ser Thr Val Val Gly Ala His
    50                  55                  60
Glu Glu Glu Pro Glu
65
```

```
<210> SEQ ID NO 81
<211> LENGTH: 68
<212> TYPE: PRT
<213> ORGANISM: Artificial Sequence
<220> FEATURE:
<223> OTHER INFORMATION: receptor mutant

<400> SEQUENCE: 81
```

```
Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
            20                  25                  30

Gly Leu Glu Met Lys Ser Thr Arg Tyr Leu Gln Thr Gln Gly Val Tyr
            35                  40                  45

Lys Val Ser Arg Leu Glu Thr Thr Ile Ser Thr Val Ala Gly Ala Ala
    50                  55                  60

Glu Glu Glu Pro
65

<210> SEQ ID NO 82
<211> LENGTH: 5
<212> TYPE: PRT
<213> ORGANISM: Artificial Sequence
<220> FEATURE:
<223> OTHER INFORMATION: amino acid motif
<220> FEATURE:
<221> NAME/KEY: VARIANT
<222> LOCATION: 3, 4
<223> OTHER INFORMATION: Xaa = Any Amino Acid

<400> SEQUENCE: 82

Asn Pro Xaa Xaa Tyr
1               5
```

MODIFIED G-PROTEIN COUPLED RECEPTORS

This application is a divisional of U.S. application Ser. No. 09/993,844, filed Nov. 5, 2001 now U.S. Pat. No. 7,018,812, which claims the benefit of U.S. Provisional Application No. 60/245,772, filed Nov. 3, 2000 and U.S. Provisional Application No. 60/260,363, filed Jan. 8, 2001; the contents of these applications are hereby incorporated by reference herein in their entirety.

This invention was made with Government support under Grant Nos. HL61365 and NS19576 awarded by the National Institutes of Health. The Government has certain rights in the invention.

FIELD OF THE INVENTION

The present invention relates to modified G-protein coupled receptors (GPCRs). The modified GPCRs of the present invention include GPCRs that have been modified to have carboxyl terminal tails comprising one or more sites of phosphorylation, preferably clusters of phosphorylation sites. This invention also relates to methods of detecting G protein-coupled receptor (GPCR) activity and methods of assaying GPCR activity. The present invention provides methods for identifying compounds that interact with components of the GPCR regulatory pathway and methods for identifying ligands of GPCRs.

BACKGROUND OF THE INVENTION

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

The magnitude of the physiological responses controlled by GPCRs is linked to the balance between GPCR signaling and signal termination. The signaling of GPCRs is controlled by a family of intracellular proteins called arrestins. Arrestins bind activated GPCRs, including those that have been agonist-activated and especially those that have been phosphorylated by G protein-coupled receptor kinases (GRKs).

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See eg., Jurgen Drews, (2000) "Drug Discovery: A Historical Perspective," *Science* 287:1960–1964.

Although only several hundred human GPCRs are known, it is estimated that several thousand GPCRs exist in the human genome. Of these known GPCRs, many are orphan receptors that have yet to be associated with a function or ligands.

There is a need for accurate, easy to interpret methods of detecting G protein-coupled receptor activity and methods of assaying GPCR activity. One method, as disclosed in Barak et al., U.S. Pat. Nos. 5,891,646 and 6,110,693, uses a cell expressing a GPCR and a conjugate of an arrestin and a detectable molecule, the contents of which are incorporated by reference in their entirety.

In some instances, naturally occurring GPCRs do not provide optimal association with arrestin for easy detection. Accordingly, for those receptors that do not exhibit optimal association with arrestin, there is a need to increase affinity of the naturally occurring GPCRs with arrestin to provide for a more sensitive assay.

Therefore, in view of the aforementioned deficiencies attendant with prior art methods of detecting G protein-coupled receptor activity, it should be apparent that there still exists a need in the art for the same. In designing this improved method, it should also be apparent that the identification of molecules which modulate G protein-coupled receptors would likewise be improved.

SUMMARY OF THE INVENTION

A first aspect of the present invention is a modified GPCR. The modified GPCRs of the present invention may have one or more modifications in their carboxyl terminal tail region. The carboxyl-terminal tail region may be modified by discrete point mutations or by exchange.

The present invention relates to the polypeptide sequences of modified GPCRs, the nucleic acid sequences encoding modified GPCRs, expression vectors comprising the nucleic acid sequence encoding a modified GPCR operably linked to an expression control sequence, and host cells expressing one or more modified GPCRs of the present invention.

The modified GPCRs of the present invention include GPCRs that have been modified to have one or more sites of phosphorylation, preferably clusters of phosphorylation sites, properly positioned in their carboxyl terminal tails. The modified GPCRs of the present invention have an increased affinity for arrestin. This increased affinity for arrestin improves their performance in assays that monitor GPCR activity. These modified GPCRs are constructed such that the one or more sites of phosphorylation, preferably clusters of phosphorylation sites, are properly positioned within the carboxyl-terminal tail to enhance the modified GPCR's affinity for arrestin.

In its broadest aspect, the present invention extends to GPCRs which have an increased affinity to arrestin. By increased affinity, the arrestin remains associated with the modified GPCRs of the present invention and traffics with the receptor into endosomes, as opposed to dissociating at or near the plasma membrane.

In a further aspect, the modified GPCR has been modified to contain one or more sites of phosphorylation, preferably clusters of phosphorylation sites, properly positioned within its carboxyl tail.

The present invention relates to all members of the herein disclosed family of GPCRs, examples of which are listed in FIG. 1.

The modified GPCRs of the present invention include GPCRs comprising a NPXXY motif (SEQ ID NO: 82), a putative site of palmitoylation, and a modified carboxyl terminal tail. The carboxyl terminal tail may include one or more additions, substitutions, mutations, or deletions of amino acid residues such that the carboxyl-terminal tail comprises one or more sites of phosphorylation, preferably clusters of phosphorylation sites. The phosphorylation sites are positioned such that they are approximately 15 to 35 (preferably 15 to 25) amino acid residues downstream of the putative site of palmitoylation of the modified GPCR. The modified carboxyl terminal tail may be modified by discrete point mutations.

The modified carboxyl terminal tail may also by modified by exchange such that it comprises a retained portion and a exchanged portion. The retained portion may be fused to a polypeptide comprising one or more sites of phosphorylation, preferably clusters of phosphorylation sites. The portions may be fused such that the one or more clusters of phosphorylation sites are at approximately 15 to 35 (preferably 15 to 25) amino acid residues downstream of the putative site of palmitoylation of the modified GPCR. Furthermore, the retained portion and the polypeptide may be fused at an amino acid residue adjacent to the putative site of palmitoylation.

In a further aspect, the modified GPCRs of the present invention include GPCRs comprising a NPXXY motif (SEQ ID NO: 82) and a carboxyl terminal tail. The carboxyl terminal tail comprises a putative site of palmitoylation and one or more clusters of phosphorylation sites. The carboxyl-terminal tail may comprise a retained portion of a carboxyl-terminus region of a first GPCR fused to a portion of a carboxyl-terminus from a second GPCR. The second GPCR comprises the one or more sites of phosphorylation, preferably clusters of phosphorylation sites. The second GPCR further comprises a putative site of palmitoylation approximately 10 to 25 amino acid residues, preferably approximately 15 to 20 amino acid residues, downstream of a NPXXY motif (SEQ ID NO: 82).

In an additional aspect, the modified GPCRs of the present invention also may include GPCRs comprising a NPXXY motif (SEQ ID NO: 82) and a carboxyl-terminal tail. The carboxyl terminal tail comprises a palmitoylated cysteine residue and one or more sites of phosphorylation, preferably clusters of phosphorylation sites. The carboxyl terminal tail of the modified receptor may comprise a retained portion of a carboxyl-terminus region of a first GPCR fused to a portion of a carboxyl-terminus from a second GPCR. The second GPCR comprises the one or more sites of phosphorylation, preferably clusters of phosphorylation sites. The retained portion of the first GPCR and the second GPCR are fused at an amino acid residue adjacent to the palmitoylated cysteine residue.

An additional aspect of the present invention is a host cell that expresses at least one modified GPCR of the present invention. The host cell may also contain a conjugate of an arrestin protein and a detectable molecule. The host cell may be a mammalian, bacterial, yeast, fungal, plant, insect, or animal cell, and may be deposited on a substrate.

A further aspect of the present invention is a substrate having deposited thereon a plurality of cells that express at least one modified GPCR of the present invention. The host cells deposited on the substrate may also contain a conjugate of an arrestin protein and a detectable molecule.

An additional aspect of the present invention is a membrane preparation isolated from cells comprising the modified GPCRs of the present invention.

A further aspect of the present invention is a method of screening compounds and sample solutions for GPCR agonist, antagonist, inverse agonist, or desensitization activity. Compounds and sample solutions may be screened by a method comprising using a modified GPCR of the present invention. Preferably, a cell is provided that expresses at least one modified GPCR of the present invention and that further comprises a conjugate of an arrestin protein and a detectable molecule. The sample compounds or sample solutions are provided and the cells are exposed to the sample compounds or solutions. Interaction of the arrestin protein with the modified GPCR along the translocation pathway is detected. In the methods of the present invention, the modified GPCRs may also be conjugated with a detectable molecule.

An additional aspect of the present invention is a method for identifying ligands of GPCRs. Such ligands may be agonists or antagonists, and serve to modulate the activity of the GPCR. GPCRs have been implicated in a number of disease states, which are detailed below, and as such, modulation of GPCR activity is useful in the amelioration of effects of those diseases. Likewise, also included in the invention are the compounds identified by the methods.

Another aspect of the invention relates to methods of treating a human or non-human subject suffering from a GPCR-related disease. Such treatment can be performed either by administering to a subject in need of such treatment, an amount of the agonists or antagonists identified by the present method sufficient to treat the GPCR-related disease, or at least to lessen the symptoms thereof. Treatment may also be effected by administering to the subject the naked modified nucleic acid sequences of the invention, such as by direct injection, microprojectile bombardment, delivery via liposomes or other vesicles, or by means of a vector which can be administered by one of the foregoing methods. Gene delivery in this manner may be considered gene therapy.

Yet another aspect of the invention relates to methods of diagnosing a GPCR-related dysfunction or disorder in a human or non-human subject using the modified GPCR of the present invention. Such diagnosis may be performed using a molecule capable of detecting a GPCR or the nucleic acid encoding the GPCR in a sample from a subject. Such molecules include ligands. After exposure to the ligands, the affinity of the GPCR for arrestin can be compared to a normal control subject to determine whether a dysfunction or disorder is present. Likewise, antibodies, either polyclonal or monoclonal, are suitable for this purpose. In addition, nucleic acid probes may be used to detect the sequences encoding a GPCR in a subject, such that alterations in the sequence thereof may be correlated with the dysfunction or disorder.

The present invention also relates to a recombinant DNA molecule or cloned gene, or a degenerate variant thereof, which encodes a modified GPCR. The nucleic acid molecule, in particular a recombinant DNA molecule or cloned gene, encoding the modified GPCR may have a nucleotide sequence or may be complementary to a DNA sequence shown in FIG. 11 (SEQ ID NO: 9 through SEQ ID NO: 14).

The nucleic acid sequences of the modified GPCR of the present invention or portions thereof, may be prepared as probes to screen for complementary sequences and genomic clones in the same or alternate species. The present invention extends to probes so prepared that may be provided for screening cDNA and genomic libraries for GPCRs. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the nucleic acid sequences of the invention, resulting in decreased expression of a sub-optimal GPCR. Correspondingly, the preparation of antisense RNA and ribozymes are included herein.

The present invention also includes modified GPCR proteins having the activities noted herein, and that display the amino acid sequences set forth and described above and selected from SEQ ID NO: 3–SEQ. ID No. 8.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present modified GPCR(s), and more particularly, the complete DNA sequence determined from the sequences set forth above and in SEQ ID NO: 9 through SEQ ID NO: 14.

According to other preferred features of certain preferred embodiments of the present invention, a recombinant expression system is provided to produce biologically active animal or human modified GPCRs.

The concept of the modified GPCR contemplates that specific factors exist for correspondingly specific ligands. Accordingly, the exact structure of each GPCR will understandably vary so as to achieve this ligand and activity specificity. It is this specificity and the direct involvement of the GPCR in the chain of events leading to G protein-linked second messengers, that offers the promise of a broad spectrum of diagnostic and therapeutic utilities.

In addition to identifying agonists and antagonists of the modified GPCR, and correspondingly, to the wild type GPCR exhibiting the same, or nearly the same, ligand binding portion, the present method can also be used for identifying compounds which target membrane-bound proteins, such as GPCRs, to endosomes. Likewise, the method can be used to detect GPCRs with altered endosome targeting, and for detecting endosome-related disease states.

In addition to using the entire GPCR for the aforementioned diagnostic and therapeutic purposes, it may be possible to use only a portion of the GPCR for such purposes, for example by using only the V2R tail.

In another aspect of the invention, the modified GPCR may be used for delivering a molecule or drug into a cell, by binding of the same to the ligand-binding portion of the GPCR, followed by endocytosis of the GPCR-drug complex.

The present invention naturally contemplates several means for preparation of the modified GPCRs, including as illustrated herein known recombinant techniques, and the invention is accordingly intended to cover such synthetic preparations within its scope. The isolation of the cDNA and amino acid sequences disclosed herein facilitates the reproduction of the modified GPCRs by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate GPCR activity of target mammalian cells by interrupting or potentiating the action of the GPCR subsequent to ligand binding. In one instance, the test drug could be administered to a cellular sample with the ligand that activates the GPCRs, or an extract containing the modified GPCR, to determine its effect upon the affinity of GPCR for arrestin, by comparison with a control.

The assay system could more importantly be adapted to identify drugs or other entities that are capable of binding to the GPCRs, either at the plasma membrane or in the cytoplasm, thereby inhibiting or potentiating GPCR activity. Such assay would be useful in the development of drugs that would be specific against particular cellular activity, or that would potentiate such activity, in time or in level of activity.

In yet a further embodiment, the invention contemplates antagonists of the activity of a GPCR. In particular, an agent or molecule that inhibits interaction with a G protein or subsequent activation of second messengers.

The diagnostic utility of the present invention extends to the use of the present modified GPCRs in assays to screen for drugs suitable to treat GPCR-related diseases.

The present invention likewise extends to the development of antibodies against the modified GPCR(s), or more specifically to their modified tails, including naturally raised and recombinantly prepared antibodies. For example, the antibodies could be used to screen expression libraries to obtain the gene or genes that encode GPCR(s). Such antibodies could include both polyclonal and monoclonal antibodies prepared by known genetic techniques, as well as bi-specific (chimeric) antibodies, and antibodies including other functionalities suiting them for additional diagnostic use, or for their use in modulating GPCR-related activity.

In particular, antibodies against specifically phosphorylated GPCR tails can be selected and are included within the scope of the present invention for their particular ability in following activated protein. Thus, activity of the GPCR or of the specific polypeptides believed to be causally connected thereto may therefore be followed directly by the assay techniques discussed later on, through the use of an appropriately labeled quantity of the GPCR or antibodies thereto.

Thus, the modified GPCRs, their analogs and/or analogs, and any agonists, antagonists or antibodies that may be raised thereto, are capable of use in connection with various diagnostic techniques, including immunoassays, such as a radioimmunoassay, using for example, an antibody to the modified GPCR that has been labeled by either radioactive addition, or radioiodination.

In an immunoassay, a control quantity of the ligands or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against specifically phosphorylated GPCR tail may be selected and appropriately employed in the exemplary assay protocol, for the purpose of following activated protein as described above.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention includes an assay system which may be prepared in the form of a test kit for the quantitative analysis of the extent of the presence of the GPCR, and for analysis of the affinity for arrestin thereof, or to identify drugs or other agents that modulate their activity. The system or test kit may comprise a labeled component prepared by one of the radioactive and/or enzymatic techniques discussed herein, coupling a label to the GPCR, their agonists and/or antagonists, or antibodies thereto, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the modified GPCR(s), its (or their) subunits, or active fragments thereof, or upon agents or other drugs determined to possess the same activity. A first therapeutic method is associated with the prevention of the manifestations of conditions causally related to or following from the binding activity of the GPCR or its subunits, and comprises administering an agent capable of modulating the production and/or activity of the GPCR or fragments thereof, either individually or in mixture with each other in an amount effective to prevent the development of those conditions in the host. For example, drugs or other binding partners to the GPCR or proteins may be administered to inhibit or potentiate GPCR activity. Also, the blockade of the action of specific kinases and/or phosphatases in the GPCR-associated cascade of reactions presents a method for potentiating the activity of the GPCR that would concomitantly potentiate therapies based on GPCR activation.

More specifically, the therapeutic method generally referred to herein could include the method for the treatment of various pathologies or other cellular dysfunctions and derangements by the administration of pharmaceutical compositions that may comprise effective inhibitors or enhancers of activation of the GPCR or its subunits or fragments, or other equally effective drugs developed for instance by a drug screening assay prepared and used in accordance with a further aspect of the present invention. For example, drugs or other binding partners to the GPCR, may be administered to inhibit or potentiate GPCR activity. Also, the blockade of the action of specific kinases or phosphatases in the phosphorylation cascade of the GPCR presents a method for modulating the activity of the GPCR that would concomitantly potentiate therapies based on GPCR activation.

In particular, the modified GPCRs, their antibodies, agonists, antagonists, or active fragments thereof, could be prepared in pharmaceutical formulations for administration in instances wherein therapy is appropriate.

Accordingly, it is a principal object of the present invention to provide a modified GPCR and its subunits in purified form that exhibits certain characteristics and activities associated with GPCR binding to a ligand.

It is a further object of the present invention to provide agonists, antagonists, and antibodies to the GPCR and its subunits, and methods for their preparation, including recombinant means.

It is a further object of the present invention to provide a method for detecting the presence of the GPCR, preferably a GPCR having discrete point mutations that increases its affinity for arrestin, and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the GPCR binding to ligands in mammals.

It is a still further object of the present invention to provide a method for the treatment of mammals to control the amount or activity of the GPCR, preferably a GPCR having discrete point mutations that increases its affinity for arrestin, so as to alter the adverse consequences of such presence or activity, or where beneficial, to enhance such activity.

It is a still further object of the present invention to provide a method for the treatment of mammals to control the amount or activity of the GPCR, preferably a GPCR having discrete point mutations that increases its affinity for arrestin, or its subunits, so as to treat or avert the adverse consequences of invasive, spontaneous or idiopathic pathological states.

It is a still further object of the present invention to provide pharmaceutical compositions for use in therapeutic methods Which comprise or are based upon the GPCRs, their carboxyl tails, their binding partner(s), or upon agents or drugs that control the production, or that mimic or antagonize the activities of the GPCRs.

Other objects and advantages will become apparent to those skilled in the art from a review of the ensuing description which proceeds with reference to the following illustrative drawings.

BRIEF DESCRIPTION OF THE DRAWINGS

FIG. 1 is an illustrative, non-limiting list of known GPCRs with which the present invention may be used is contained in FIG. 1. The receptors are grouped according to classical divisions based on structural similarities and ligands.

FIG. 2 is an illustrative, non-limiting list (SEQ ID NOS: 15–53) of known receptors, including the amino acid sequence for their carboxyl terminal tails and appropriate classification. For the Class B receptor examples, the residues that may function as phosphorylation sites in the enhanced affinity motifs are shown in bolded italics.

FIG. 3A shows human V2R nucleic acids (SEQ ID NO: 54) encoding the last 29 amino acids of the human V2R carboxyl terminus and the adjacent stop codon. FIG. 3B (SEQ ID NO: 55) shows the PCR amplified human V2R DNA fragment, incorporating the changes introduced in the PCR primers.

FIG. 4A is a schematic of the pEArrB-1 vector resulting from digestion of the PCR-amplified V2R DNA fragment and cloning into the pcDNA3.1zeo+ vector. FIG. 4B is a schematic of the pEArrB-1/GPCR vector resulting from the insertion of the nucleic acids of the GPCR of interest (after PCR-amplification and digestion of the nucleic acids of the GPCR) into the pEArrB-1 vector. FIG. 4C is the sequence (SEQ ID NO: 56) of the 31 amino acid peptide that will be the carboxy terminus of the modified GPCR. The first two amino acids will be alanine residues, and the last 29 amino acids will be from the V2R carboxyl terminus (V2R amino acids 343–371).

FIG. 5 illustrates cellular trafficking of βarr-2-GFP with the $β_2$AR, V2R, and $β_2$AR-V2R and V2R-$β_2$AR chimeras. FIG. 5 shows confocal microscopic images of βarr-2-GFP fluorescence in the same HEK-293 cells treated with agonist for 0, 2, and 15 min. at 37° C.

FIG. 6 shows confocal visualizations of the receptor immunofluorescence and the βarr-2-GFP fluorescence. Colocalization of the receptor with the βarr-2-GFP is indicated in the overlay.

FIG. 7 shows confocal microscopic images of βarr-2-GFP fluorescence in representative cells.

FIG. 8A shows the amino acid composition of the carboxyl-terminal tails of the V2R, $β_2$AR, and various mutant receptors beginning with the putative sites of palmitoylation in bold (Cys-342 for the V2R constructs 1–5, and Cys-341 for the β2AR constructs 6–9). Underlined are the mutations made by alanine substitution and the last 10 amino acids of the V2R tail when added to the $\beta_2$AR. FIG. 8B shows the carboxyl-terminal tails of the NTR-1, OTR, and SPR (SEQ ID NOS: 76–81) which contain multiple clusters of serine and threonine residues. Receptor mutants resulting from the mutation of individual clusters to alanine residues are indicated below each wild-type receptor. FIG. 8C is a continuation of FIG. 8B.

FIG. 9A shows the amino acid sequence, termed SEQ ID NO:1, of the wild-type V2R receptor. FIG. 9B shows the amino acid sequence, termed SEQ ID NO:2, of the wild-type $\beta_2$AR receptor. FIG. 9C shows the amino acid sequence, termed SEQ ID NO:3, of the $\beta_2$AR-V2R chimera.

FIG. 10A shows the amino acid sequence, termed SEQ ID NO:4, of the MOR-V2R chimera expressed from the pEArrB-1/MOR vector. FIG. 10B shows the amino acid sequence, termed SEQ ID NO:5, of the D1AR-V2R chimera expressed from the pEArrB-1/D1AR vector. FIG. 10C shows the amino acid sequence, termed SEQ ID NO: 6, of the 5HT1AR-V2R chimera expressed from the pEArrB-1/5HT1AR vector. FIG. 10D shows the amino acid sequence, termed SEQ ID NO: 7, of the $\beta_3$AR-V2R chimera expressed from the pEArrB-1/$\beta_3$AR vector. FIG. 10E shows the amino acid sequence, termed SEQ ID NO:8, of the Edg1R-V2R chimera expressed from the pEArrB-1/Edg1R vector.

FIG. 11A shows the nucleic acid sequence, termed SEQ ID NO:9, of the $\beta_2$AR-V2R chimera. FIG. 11B shows the nucleic acid sequence, termed SEQ ID NO:10, of the MOR-V2R chimera. FIG. 11C shows the nucleic acid sequence, termed SEQ ID NO:11, of the D1AR-V2R chimera. FIG. 11D shows the nucleic acid sequence, termed SEQ ID NO:12, of the 5HT1AR-V2R chimera. FIG. 11E shows the nucleic acid sequence, termed SEQ ID NO:13, of the $\beta_3$AR-V2R chimera. FIG. 11F shows the nucleic acid sequence, termed SEQ ID NO:14, of the Edg1-V2R chimera.

FIG. 12 shows confocal microscopic images of βarr-2-GFP fluorescence in the HEK-293 cells.

FIG. 13 shows confocal microscopic images of βarr-2-GFP fluorescence in the HEK-293 cells.

FIG. 14 shows confocal microscopic images of βarr-2-GFP fluorescence in the HEK-293 cells.

FIG. 15 shows confocal microscopic images of βarr-2-GFP fluorescence in the HEK-293 cells.

FIG. 16 shows confocal microscopic images of βarr-2-GFP fluorescence in the HEK-293 cells.

DETAILED DESCRIPTION OF THE PREFERRED EMBODIMENTS

Figure 6:
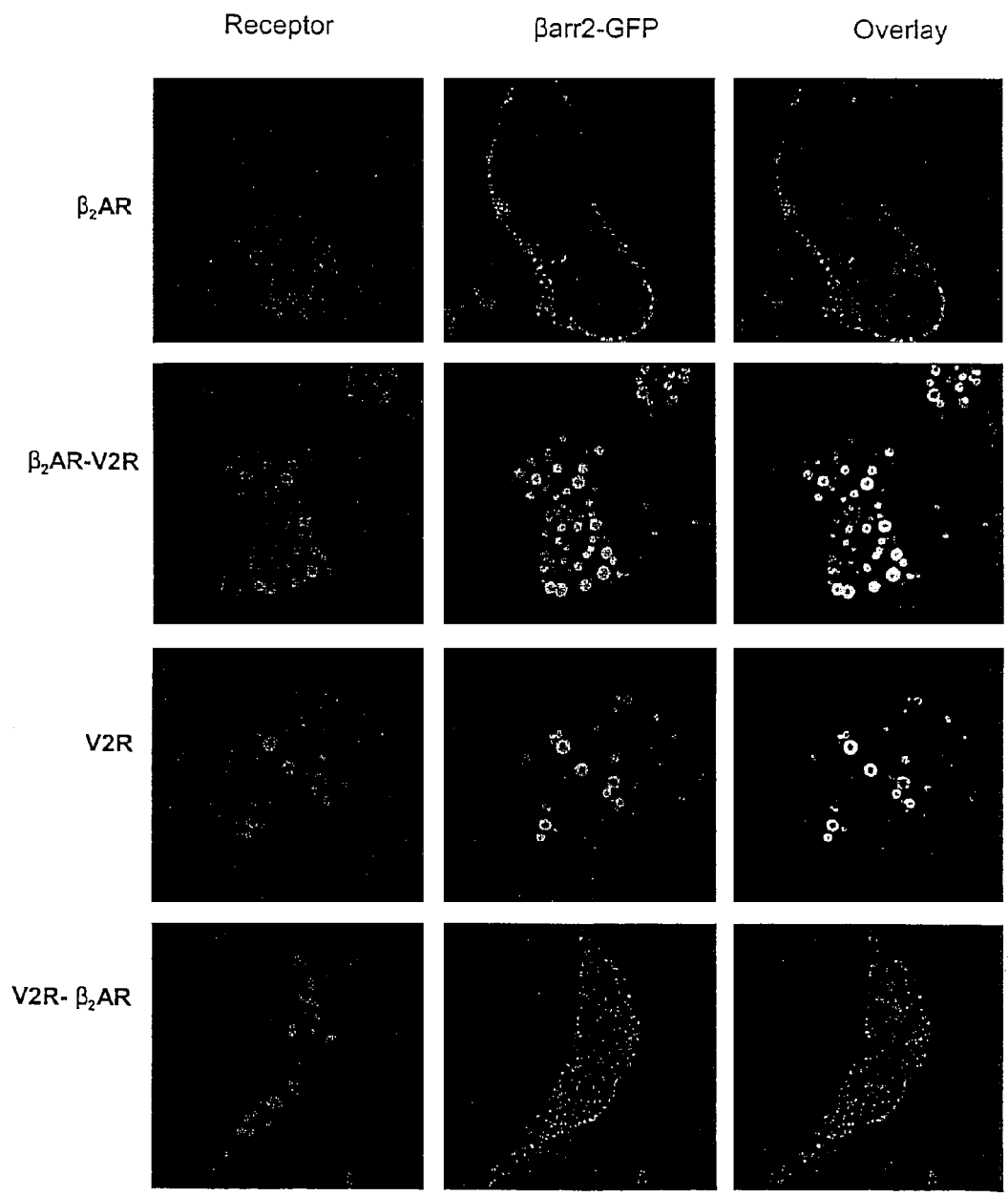
FIG. 6 illustrates colocalization of βarr2-GFP with internalized $β_2$AR, V2R, and $β_2$AR-V2R and V2R-$β_2$AR chimeras.

In accordance with the present invention there may be employed conventional molecular biology, microbiology, and recombinant DNA techniques within the skill of the art. Such techniques are explained fully in the literature. See, e.g., Sambrook et al,"Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (2000)]; "Immobilized Cells And Enzymes" [IRL Press, (1986)]; B. Perbal, "A Practical Guide To Molecular Cloning" (1984).

Unless otherwise stated, the following terms used in the specification and claims have the meanings given below:

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokarotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding GPCRs having the same amino acid sequence as SEQ ID NO: 3–SEQ. ID No. 8, but which are degenerate to SEQ ID NO: 3–SEQ. ID No. 8. By "degenerate to" is meant that a different three-letter codon is used to specify a particular amino acid.

"Arrestin" means all types of naturally occurring and engineered variants of arrestin, including, but not limited to, visual arrestin (sometimes referred to as Arrestin 1), β-arrestin 1 (sometimes referred to as Arrestin 2), and β-arrestin 2 (sometimes referred to as Arrestin 3).

"Carboxyl-terminal tail" means the carboxyl-terminal tail of a GPCR. The carboxyl-terminal tail of many GPCRs begins shortly after the conserved NPXXY motif (SEQ ID NO: 82) that marks the end of the seventh transmembrane domain (i.e. what follows the NPXXY motif (SEQ ID NO: 82) is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent).

"Class A receptor" means a GPCR that does not have one or more sites of phosphorylation, preferably clusters of phosphorylation sites, properly positioned in its carboxyl-terminal tail such that it does not recruit rat β-arrestin-2 to endosomes in HEK-293 cells under conditions as described in U.S. Pat. No. 5,891,646 and Oakley, et al. "Differential Affinities of Visual Arrestin, βArrestin1, and βArrestin2 for G Protein-coupled Receptors Delineate Two Major Classes of Receptors," *Journal of Biological Chemistry*, Vol 275, No. 22, pp 17201–17210, Jun. 2, 2000, the contents of which are hereby incorporated by reference in their entirety. Receptors are classified as Class A on the basis of their interactions with naturally-occurring rat β-arrestin 2 isoforms as described in the above, and may be predicted based on the amino acid residues in their carboxyl-terminal tails.

"Class B receptor" means a GPCR that has one or more sites of phosphorylation, preferably clusters of phosphorylation sites, properly positioned in its carboxyl-terminal tail such that it does recruit rat β-arrestin-2 to endosomes in HEK-293 cells under conditions as described in U.S. Pat. No. 5,891,646 and Oakley, et al. "Differential Affinities of Visual Arrestin, βArrestin1, and βArrestin2 for G Protein-coupled Receptors Delineate Two Major Classes of Receptors," *Journal of Biological Chemistry*, Vol 275, No. 22, pp 17201–17210, Jun. 2, 2000, the contents of which are hereby incorporated by reference in their entirety. Receptors are classified as Class B on the basis of their interactions with naturally-occurring rat β-arrestin 2 isoforms as described in the above, and may be predicted based on the amino acid residues in their carboxyl-terminal tails.

"DACs" mean any desensitization active compounds. Desensitization active compounds are any compounds that influence the GPCR desensitization mechanism by either stimulating or inhibiting the process. DACs influence the GPCR desensitization pathway by acting on any cellular component of the process, as well as any cellular structure implicated in the process, including but not limited to, arrestins, GRKs, GPCRs, AP-2 protein, clathrin, protein phosphatases, and the like. DACs may include but are not limited to, compounds that inhibit arrestin translocating to a GPCR, compounds that inhibit arrestin binding to a GPCR, compounds that stimulate arrestin translocating to a GPCR, compounds that stimulate arrestin binding to a GPCR, compounds that inhibit GRK phosphorylation of a GPCR, compounds that stimulate GRK phosphorylation of a GPCR, compounds that inhibit protein phosphatase dephosphorylation of a GPCR, compounds that stimulate protein phosphatase dephosphorylation of a GPCR, compounds that regulate the release of arrestin from a GPCR, antagonists of a GPCR, inverse agonists and the like. DACs preferably inhibit or stimulate the GPCR desensitization process without binding to the same ligand binding site of the GPCR as traditional agonists and antagonists of the GPCR. DACs act independently of the GPCR, i.e. they do not have high specificity for one particular GPCR or one particular type of GPCRs.

"Detectable molecule" means any molecule capable of detection by spectroscopic, photochemical, biochemical, immunochemical, radiochemical, electrical, and optical means, including but not limited to, fluorescence, phosphorescence, radioactivity, and bioluminescence. Detectable molecules include, but are not limited to GFP, luciferase, rhodamine-conjugated antibody, and the like.

"GFP" means Green Fluorescent Protein which refers to various naturally occurring forms of GFP which may be isolated from natural sources or genetically engineered, as well as artificially modified, GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered or modified, including but not limited to, yellow fluorescent proteins (YFP), red fluorescent proteins (RFP), cyan fluorescent proteins (CFP), UV excitable fluorescent proteins, or any wavelength in between.

"Modified GPCR" means a GPCR that has one or more modifications in the amino acid sequence of its carboxyl-terminal tail. As such, the carboxyl-terminal tail may be modified in whole or in part. These modifications in the amino acid sequence include mutations of one or more amino acids, insertion of one or more amino acids, deletion of one or more amino acids, and substitutions of one or more amino acids in which one or more amino acids are deleted and one or more amino acids are added in place of the deleted amino acids.

"Unknown or Orphan Receptor" means a GPCR whose function and/or ligands are unknown.

"Putative site of palmitoylation" means an expected site of palmitate addition, preferably a cysteine residue. In the GPCRs used in the present invention, the putative site of palmitoylation is preferably 10 to 25, preferably 15 to 20, amino acid residues downstream of the NPXXY motif (SEQ ID NO: 82).

"Clusters of phosphorylation sites" mean clusters of amino acid residues that may be efficiently phosphorylated and thus readily function as phosphorylation sites. The clusters of amino acids occupy two out of two, two out of three, three out of three positions, three out of four positions, four out of four, four out of five positions, five out of five, and the like consecutive amino acid positions in the carboxyl terminal tail of a GPCR. These clusters of phosphorylation sites are preferably clusters of serine (S) and/or threonine (T) residues. Clusters of phosphorylation sites may be substituted, inserted, or added on to a GPCR sequence so that the resulting modified GPCR binds arrestin with sufficient affinity to recruit arrestin into endosomes.

"NPXXY motif (SEQ ID NO: 82) means a conserved amino acid motif that marks the end of the seventh transmembrane domain. The conserved amino acid motif begins with asparagine and proline followed by two unspecified amino acids and then a tyrosine. The two unspecified amino acids may vary among GPCRs but the overall NPXXY motif (SEQ ID NO: 82) is conserved.

"Downstream" means toward a carboxyl-terminus of an amino acid sequence, with respect to the amino-terminus.

"Upstream" means toward an amino-terminus of an amino acid sequence, with respect to the carboxyl-terminus.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce some feature of pathology such as for example, elevated blood pressure, respiratory output, etc.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

The present invention is related to modified GPCRs, polypeptides of modified GPCRs, nucleic acid molecules that encode the modified GPCRs, vectors containing the nucleic acid molecules which encode the modified GPCRs, vectors enabling the nucleic acid construction of the modified GPCRs, and cells containing modified GPCRs. The invention further relates to assay systems using the modified GPCRs, assay systems using the cells containing modified GPCRs, compounds identified using the assay systems, methods of treatment using the compounds identified, methods of disease diagnosis using the assay systems, and kits containing assay reagents of the present invention and cells of the present invention. The invention also may relate to antisense and treatment techniques using the modified GPCR nucleic acids.

Mutations can be made in the GPCR or modified GPCR such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

In a particular embodiment, the modified GPCRs of the present invention include GPCRs that have been modified to have one or more sites of phosphorylation, preferably clusters of phosphorylation sites, properly positioned in its carboxyl-terminal tail. These modified GPCRs recruit arrestin to endosomes within approximately 30 minutes of agonist stimulation.

The modified GPCRs of the present invention comprise one or more sites of phosphorylation, preferably one or more clusters of phosphorylation sites, properly positioned in its carboxyl-terminal tail. The present inventors have discovered that GPCRs containing one or more sites of phosphorylation, preferably clusters of phosphorylation sites, properly positioned in its carboxyl-terminal tail have an increased affinity for arrestin and colocalize with arrestin in endosomes after stimulation with agonist. The present inventors have also discovered that the one or more sites of phosphorylation, preferably clusters of phosphorylation sites, must be optimally positioned within the GPCR tail for the GPCR to have an increased affinity for arrestin. Therefore, the modified GPCRs may be constructed such that the one or more sites of phosphorylation, preferably clusters of phosphorylation sites, are optimally positioned within the carboxyl-terminal tail. The portions of polypeptides, which are to be fused together to form the modified GPCR, are chosen such that the one or more sites of phosphorylation, preferably clusters of phosphorylation sites, are reliably positioned properly within the carboxyl-terminal tail. In the alternative, the location of discrete point mutations to create the modified GPCR may be chosen so that the one or more sites of phosphorylation, preferably clusters of phosphorylation sites, are properly positioned within the carboxyl-terminal tail.

The present inventors have discovered that the modified GPCRs of the present invention are useful in assays for screening compounds that may alter G protein-coupled receptor (GPCR) activity. Examples of assays in which the present invention may be used include, but are not limited to, those as described in U.S. Pat. Nos. 5,891,646 and 6,110,693, the disclosures of which are hereby incorporated by reference in their entireties. Additional examples of assays in which the present invention may be used include, but are not limited to, assays using Fluorescent Resonance Energy Transfer (FRET) and assays using Bioluminescence Resonance Energy Transfer (BRET) technology as described in Angers, S., Salahpour, A., Joly, E., Hilairet, S., Chelsky, "β2-adrenergic receptor dimerization in living cells using bioluminescence resonance energy transfer (BRET)," *Proc. Natl. Acad. Sci.* USA 97, 7: 3684–3689.

An illustrative, non-limiting list of known GPCRs with which the present invention may be used is contained in FIG. 1. The receptors are grouped according to classical divisions based on structural similarities and ligands.

By way of example, the present inventors have identified three major classes of GPCRs for known receptors: Class A receptors, Class B receptors, and receptors with virtually non-existant carboxyl-terminal tails. The receptors are classified accordingly based on their interactions with and affinity for rat β-arrestin-2 in HEK-293 cells as described above, and may be predicted based on the amino acid residues in their carboxyl-terminal tail and the length of their carboxyl-terminal tail. As defined above, Class B receptors have one or more sites of phosphorylation, preferably clusters of phosphorylation sites, properly positioned in their carboxyl-terminal tails such that they recruit rat β-arrestin-2 to endosomes in HEK-293 cells. Also as defined above, Class A receptors do not have one or more sites of phosphorylation, preferably clusters of phosphorylation sites, properly positioned in their carboxyl-terminal tails such that they do not recruit β-arrestin-2 to endosomes in HEK-293 cells. Receptors with virtually non-existent carboxyl-terminal tails include, for example, olfactory and taste receptors. In FIG. 2 is an illustrative, non-limiting list of known receptors, including the amino acid sequence for their carboxyl terminal tails and appropriate classification. For the Class B receptor examples, the residues that may function as clusters of phosphorylation sites are shown in bolded italics.

It has been discovered that after agonists bind and activate GPCRs, G protein-coupled receptor kinases (GRKs) phosphorylate clusters of serine and threonine residues located in the third intracellular loop or the carboxyl-terminal tail of the GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a non-signaling, desensitized receptor.

The arrestin bound to the desensitized GPCR targets the GPCR to clathrin-coated pits for endocytosis by functioning as an adaptor protein, which links the GPCR to components of the endocytic machinery, such as adaptor protein-2 (AP-2) and clathrin. The internalized GPCRs are dephosphorylated in the endosomes and are recycled back to the cell surface resensitized.

The present inventors have discovered that the stability of the interaction of arrestin with the GPCR dictates the rate of GPCR dephosphorylation, recycling, and resensitization. When the GPCR has an enhanced affinity for arrestin, the GPCR/arrestin complex is stable, remains intact and is internalized into endosomes. When the GPCR does not have an enhanced affinity for arrestin, the GPCR/arrestin complex tends not to be stable and arrestin is not recruited into endosomes with the GPCR. GPCRs, which have an enhanced affinity for arrestin and thus the GPCR/arrestin complex remains intact, dephosphorylate, recycle and resensitize slowly. In contrast, GPCRs that dissociate from arrestin at or near the plasma membrane dephosphorylate and recycle rapidly.

The present inventors have discovered that the ability of the arrestin to remain associated with the GPCRs is mediated by one or more sites of phosphorylation, preferably clusters of phosphorylation sites, properly positioned within the carboxyl-terminal tail. These clusters of phosphorylation sites are preferably serine and threonine residues located in the carboxyl-terminal tail of the GPCR. The present inventors have discovered that these clusters are remarkably conserved in their position within the carboxyl-terminal tail domain and serve as primary sites of agonist-dependent phosphorylation.

The present inventors have discovered that GPCRs, which do not naturally recruit arrestin to endosomes or do not even naturally recruit arrestin to the plasma membrane, may be modified to comprise one or more sites of phosphorylation, preferably clusters of phosphorylation sites, properly positioned in their carboxyl-terminal tail. This modification allows the modified GPCR to form a stable complex with an arrestin that will internalize into endosomes. These modified GPCRs may be useful in methods of assaying GPCR activity.

GRCRs have been implicated in a number of disease states, including, but not limited to cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, neurodegenerative diseases such as Parkinson's Disease and Alzheimer's Disease, multiple sclerosis, Epstein-Barr infection and cancer. As such, modulation of GPCR activity and affinity for arrestin is a mechanism for ameliorating these disease states.

Modified GPCRs

The present invention is related to modified GPCRs. Modified GPCRs of the present invention may comprise one or more modifications in their carboxyl-terminal tail. These modifications may comprise inserting one or more sites of phosphorylation, preferably clusters of phosphorylation sites, within certain regions of the carboxyl-terminal tail. As such, the carboxyl-terminal tail may be modified in whole or in part. The carboxyl-terminal tail of many GPCRs begins shortly after a conserved NPXXY motif (SEQ ID NO: 82) that marks the end of the seventh transmembrane domain (i.e. what follows the NPXXY motif (SEQ ID NO: 82) is the carboxyl-terminal tail of the GPCR). The carboxyl-terminal tail of many GPCRs comprises a putative site of palmitoylation approximately 10 to 25 amino acid residues, preferably 15 to 20 amino acid residues, downstream of the NPXXY motif (SEQ ID NO: 82). This site is typically one or more cysteine residues. The carboxyl-terminal tail of a GPCR may be relatively long, relatively short, or virtually non-existent. The present inventors have determined that the carboxyl-terminal tail of a GPCR determines the affinity of arrestin binding.

The present inventors have discovered that specific amino acid motifs in the carboxyl-terminal tail promote formation of a stable GPCR/arrestin complex and thus ultimately may promote recruitment of arrestin to endosomes. These amino acid motifs comprise one or more amino acids, preferably clusters of amino acid residues, that may be efficiently phosphorylated and thus readily function as phosphorylation sites. The clusters of amino acids may occupy two out of two, two out of three, three out of three, three out of four positions, four out of four, four out of five positions, five out of five, and the like consecutive amino acid positions. Accordingly, the clusters of amino acids that promote formation of a stable GPCR/arrestin complex are "clusters of phosphorylation sites." These clusters of phosphorylation sites are preferably clusters of serine and threonine residues.

GPCRs that form stable complexes with arrestin comprise one or more sites of phosphorylation, preferably clusters of phosphorylation sites. In addition to the presence of the one or more sites of phosphorylation, preferably clusters of phosphorylation sites, it has been discovered that the sites must be properly positioned within the carboxyl-terminal tail to promote formation of a stable GPCR/arrestin complex. To promote formation of a stable GPCR/arrestin complex, the one or more sites of phosphorylation, preferably one or more clusters of phosphorylation, may be approximately 15 to 35 (preferably 15 to 25) amino acid residues downstream of a putative site of palmitoylation of the GPCR. In addition, the one or more sites of phosphorylation, preferably one or more clusters of phosphorylation, may be approximately 20 to 55 (preferably 30 to 45) amino acid residues downstream of the NPXXY motif (SEQ ID NO: 82) of the GPCR. GPCRs containing one or more sites of phosphorylation, preferably clusters of phosphorylation sites, properly positioned are typically Class B receptors.

By way of example, it has been discovered that the V2R receptor comprises a cluster of phosphorylation sites (SSS) that promotes formation of a stable GPCR/arrestin complex at 19 amino acid residues downstream of the putative site of palmitoylation and 36 amino acid residues downstream of the NPXXY motif (SEQ ID NO: 82). The NTR-2 receptor comprises a cluster of phosphorylation sites (STS) that promotes formation of a stable GPCR/arrestin complex at 26 amino acid residues downstream of the putative site of palmitoylation and 45 amino acid residues downstream of the NPXXY motif (SEQ ID NO: 82). The oxytocin receptor (OTR) receptor comprises two clusters of phosphorylation sites (SSLST and STLS) that promote formation of a stable GPCR/arrestin complex, one at 20 amino acid residues downstream of the putative site of palmitoylation and the other at 29 amino acid residues downstream of the putative site of palmitoylation, and one at 38 amino acid residues downstream of the NPXXY motif (SEQ ID NO: 82) and the other at 47 amino acid residues downstream of the NPXXY motif (SEQ ID NO: 82), respectively. The substance P receptor (SPR, also known as the neurokinin-1 receptor) comprises a cluster of phosphorylation sites (TTIST) that promotes formation of a stable GPCR/arrestin complex at 32 amino acid residues downstream of the putative site of palmitoylation and 50 amino acid residues downstream of the NPXXY motif (SEQ ID NO: 82).

The present inventors have determined that GPCRs that lack one or more sites of phosphorylation, preferably clusters of phosphorylation, properly positioned within the carboxyl terminal tail form GPCR/arrestin complexes that are less stable and dissociate at or near the plasma membrane. These GPCRs are typically Class A receptors, olfactory receptors, taste receptors, and the like. However, the present inventors have discovered that stable GPCR/arrestin complexes may be achieved with GPCRs naturally lacking one or more sites of phosphorylation and having a lower affinity for arrestin by modifying the carboxyl-terminal tails of these receptors. Preferably, the carboxyl-terminal tails are modified to include one or more sites of phosphorylation, preferably one or more clusters of phosphorylation sites, properly positioned within the carboxyl terminal tail.

The present invention includes the polypeptide sequences of these modified GPCRs. The modified GPCRs of the present invention include GPCRs that have been modified to have one or more sites of phosphorylation, preferably one or more clusters of phosphorylation, properly positioned in their carboxyl terminal tails. The polypeptide sequences of the modified GPCRs of the present invention also include sequences having one or more additions, deletions, substitutions, or mutations. These mutations are preferably substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes which do not significantly alter the activity or binding characteristics of the resulting protein.

The modified GPCRs of the present invention include GPCRs containing a NPXXY motif (SEQ ID NO: 82), a putative site of palmitoylation approximately 10 to 25 amino acid residues (preferably 15 to 20 amino acids) downstream of the NPXXY motif (SEQ ID NO: 82), and a modified carboxyl-terminal tail. The modified carboxyl-terminal tail has one or more sites of phosphorylation, preferably one or more clusters of phosphorylation sites, such that the phosphorylation sites are approximately 15 to 35, preferably 15 to 25, amino acid residues downstream of the putative site of palmitoylation of the modified GPCR. The modified carboxyl-terminal tail may have one or more sites of phosphorylation, preferably one or more clusters of phosphorylation sites, such that the phosphorylation sites are approximately 20 to 55, preferably 30 to 45, amino acid residues downstream of the NPXXY (SEQ ID NO: 82) of the modified GPCR.

The present invention further includes isolated nucleic acid molecules that encode modified GPCRs. It should be appreciated that also within the scope of the present invention are DNA sequences encoding modified GPCRs which code for a modified GPCR having the same amino acid sequence as the modified GPCRs, but which are degenerate. By "degenerate to" it is meant that a different three-letter codon is used to specify a particular amino acid.

As one of skill in the art would readily understand, the carboxyl-tail of many GPCRs may be identified by the conserved NPXXY motif that marks the end of the seventh transmembrane domain.

To create a modified GPCR containing a modified carboxyl-terminus region according to the present invention, a GPCR lacking phosphorylation sites or clusters of phosphorylation sites or with a lower or unknown affinity for arrestin may have one or more additions, substitutions, deletions, or mutations of amino acid residues in its carboxyl-terminal tail. These additions, substitutions, deletions, or mutations are performed such that the carboxyl-terminal tail is modified to comprise one or more sites of phosphorylation, preferably clusters of phosphorylation sites. By way of example, discrete point mutations of the amino acid residues may be made to provide a modified GPCR. By way of example three consecutive amino acids may be mutated to serine residues to provide a modified GPCR. These mutations are made such that the one or more sites of phosphorylation, preferably clusters of phosphorylation sites, are properly positioned within the carboxyl terminal tail.

In addition, to create a modified GPCR containing a modified carboxyl-terminal tail region, mutations may be made in a nucleic acid sequence of a GPCR lacking sites of phosphorylation or clusters of phosphorylation sites or with a lower or unknown affinity for arrestin such that a particular codon is changed to a codon which codes for a different amino acid, preferably a serine or threonine. Such a mutation is generally made by making the fewest nucleotide changes possible. A substitution mutation of this sort can be made to change an amino acid in the resulting protein to create one or more sites of phosphorylation, preferably clusters of phosphorylation sites. Also by way of example, discrete point mutations of the nucleic acid sequence may be made. The phosphorylation sites are positioned such that they are located approximately 15 to 35 amino acid residues downstream of the putative site of palmitoylation of the modified GPCR.

The carboxyl-terminal tail used for the exchange may be from a second GPCR having one or more properly positioned clusters of phosphorylation sites and having a putative site of palmitoylation approximately 10 to 25 (preferably 15 to 20) amino acid residues downstream of a NPXXY motif (SEQ ID NO: 82). The tail as identified may be exchanged, after or including the conserved NPXXY motif (SEQ ID NO: 82). As an alternative, a putative site of palmitoylation of a GPCR may be identified at approximately 10 to 25 (preferably 15 to 20) amino acid residues downstream of the conserved NPXXY motif (SEQ ID NO: 82), and the tail may be exchanged after or including the palmitoylated cysteine(s). Preferably, the carboxyl-terminal tail of a GPCR having clusters of phosphorylation sites is exchanged at an amino acid residue in close proximity to a putative site of palmitoylation. More preferably, the carboxyl-terminal tail of a GPCR having clusters of phosphorylation sites is exchanged at a putative site of palmitoylation approximately 10 to 25 (preferably 15 to 20) amino acid residues downstream of the NPXXY motif (SEQ ID NO: 82), such that the portion of the carboxyl-terminal tail containing the clusters of phosphorylation sites begins at the amino acid residue immediately downstream of the palmitoylated cysteine residue. Exchanging in the preferred manner allows the clusters of phosphorylation sites to be reliably positioned properly within the carboxyl-terminal tail of the modified GPCR. The carboxyl-terminal tail having clusters of phosphorylation sites used for the exchange may have a detectable molecule conjugated to the carboxyl-terminus. The tails may be exchanged and the modified GPCRs may be constructed accordingly by manipulation of the nucleic acid sequence or the corresponding amino acid sequence.

In addition, the carboxyl-terminal tail portion used for the exchange may originate from a polypeptide synthesized to have an amino acid sequence corresponding to an amino acid sequence from a GPCR having one or more sites of phosphorylation, preferably one or more clusters of phosphorylation sites. The synthesized polypeptide may have a putative site of palmitoylation approximately 10 to 25 (preferably 15 to 20) amino acid residues downstream of a NPXXY motif (SEQ ID NO: 82). The synthesized polypeptide may have one or more additions, substitutions, mutations, or deletions of amino acid residues that does not affect or alter the overall structure and function of the polypeptide.

Furthermore, the carboxyl-terminal tail portion used for the exchange may originate from a naturally occurring polypeptide recognized to have an amino acid sequence corresponding to an amino acid sequence from a GPCR having one or more clusters of phosphorylation sites. The polypeptide may have a putative site of palmitoylation approximately 10 to 25 (preferably 15 to 20) amino acid residues downstream of a NPXXY motif (SEQ ID NO: 82). The polypeptide may have one or more additions, substitutions, mutations, or deletions of amino acid residues that does not affect or alter the overall structure and function of the polypeptide.

A modified GPCR containing a modified carboxyl-terminus region may be created by fusing a first carboxyl-terminal tail portion of a GPCR lacking properly positioned clusters of phosphorylation sites or with a lower or unknown affinity for arrestin with a second carboxyl-terminal tail portion of a GPCR or polypeptide having one or more clusters of phosphorylation sites. The second GPCR or polypeptide used for the exchange may have a putative site of palmitoylation approximately 10 to 25 (preferably 15 to 20) amino acid residues downstream of a NPXXY motif (SEQ ID NO: 82). Accordingly, the modified carboxyl-terminus region of the modified GPCR comprises a portion of a carboxyl-terminal tail from a GPCR lacking properly positioned clusters of phosphorylation sites or with a lower or unknown affinity for arrestin fused to a portion of a carboxyl-terminal tail of a GPCR or polypeptide having clusters of phosphorylation sites. The tail of a GPCR lacking properly positioned clusters of phosphorylation sites may be exchanged after or including the conserved NPXXY motif (SEQ ID NO: 82), and fused to a carboxyl-terminal tail containing clusters of phosphorylation sites, after or including the conserved NPXXY motif (SEQ ID NO: 82). As an alternative, the tail of a GPCR lacking properly positioned clusters of phosphorylation sites may be exchanged after or including the palmitoylated cysteine(s), and fused to a tail containing clusters of phosphorylation sites, after or including the palmitoylated cysteine(s). The tails may be exchanged and the modified GPCRs may be constructed accordingly by manipulation of the nucleic acid sequence or the corresponding amino acid sequence.

In a further alternative, the carboxyl-tail of a GPCR, for example a GPCR not containing the NPXXY motif (SEQ ID NO: 82), may be predicted from a hydrophobicity plot and exchanged accordingly. The site of exchange may be selected according to the hydrophobicity plot. Based on a hydrophobicity plot, one of skill in the art may predict a site where it is expected that the GPCR may anchor in the membrane and then predict where to introduce a putative site of palmitoylation accordingly. Using this technique GPCRs having neither a NPXXY motif (SEQ ID NO: 82) nor a putative site of palmitoylation may be modified to create a point of reference (e.g. a putative site of palmitoylation). The introduced putative site of palmitoylation may be then used to position a tail exchange. After introduction of a putative site of palmitoylation, the resulting tail may be fused with a second carboxyl-terminal tail portion of a GPCR or polypeptide having one or more clusters of phosphorylation sites and having a putative site of palmitoylation approximately 10 to 25 (preferably 15 to 20) amino acid residues downstream of a NPXXY motif (SEQ ID NO: 82).

Preferably, the modified carboxyl-terminus region of the modified GPCR is fused at amino acid residues in close proximity to a putative site of palmitoylation. More preferably, the modified carboxyl-terminus region of the modified GPCR is fused such that the portion from the first GPCR with a lower affinity for arrestin comprises amino acid residues from the NPXXY motif (SEQ ID NO: 82) through a putative site of palmitoylation approximately 10 to 25 (preferably 15 to 20) amino acid residues downstream of the NPXXY motif (SEQ ID NO: 82) and the portion from the second GPCR having clusters of phosphorylation sites and a putative site of palmitoylation approximately 10 to 25 (preferably 15 to 20) amino acid residues downstream of a NPXXY motif (SEQ ID NO: 82) comprises amino acid residues beginning with an amino acid residue immediately downstream of the putative site of palmitoylation of the second GPCR extending to the end of the carboxyl-terminus. This fusion is preferred because the clusters of phosphorylation sites are reliably positioned properly within the carboxyl-terminal tail and the modified GPCR maintains its structure and ability to function.

By way of example, a Class A receptor or an orphan receptor may have a portion of its carboxyl-terminal tail exchanged with a portion of a carboxyl-terminal tail from a known Class B receptor. Further, receptors having virtually non-existent carboxyl-terminal tails, for example, olfactory receptors and taste receptors, may have a portion of their carboxyl-terminal tails exchanged with a portion of a carboxyl-terminal tail from a known Class B receptor. The Class B receptor tail used for these exchanges may have a detectable molecule fused to the carboxyl-terminus.

Modified GPCRs may be generated by molecular biological techniques standard in the genetic engineering art, including but not limited to, polymerase chain reaction (PCR), restriction enzymes, expression vectors, plasmids, and the like. By way of example, vectors, such as a pEArrB (enhanced arrestin binding), may be designed to enhance the affinity of a GPCR lacking clusters of phosphorylation sites for arrestin. To form a vector, such as a pEArrB vector, PCR amplified DNA fragments of a GPCR carboxyl-terminus, which forms stable complexes with arrestin, may be digested by appropriate restriction enzymes and cloned into a plasmid. A schematic of one such plasmid is illustrated in FIG. 4A. The DNA of a GPCR, which is to be modified, may also be PCR amplified, digested by restriction enzymes at an appropriate location, and subcloned into the vector, such as pEArrB, as illustrated in FIG. 4B. When expressed, the modified GPCR will contain a polypeptide fused to the carboxyl-terminus. The polypeptide will comprise clusters of phosphorylation sites. Preferably, the polypeptide originates from the GPCR carboxyl-terminus of a receptor that forms stable complexes with arrestin.

Such modified GPCRs may also occur naturally as the result of aberrant gene splicing or single nucleotide polymorphisms. Such naturally occurring modified GPCRs would be predicted to have modified endocytic targeting. These naturally occurring modified GPCRs may be implicated in a number of GPCR-related disease states.

As shown in FIG. 9C, a portion of a $\beta_2$AR, a Class A receptor, may be fused to a portion of a V2R receptor (a Class B receptor). Accordingly, the first 341 amino acids of the $\beta_2$AR, Met-1 through Cys-341 (a putative site of palmitoylation) were fused to the last 29 amino acids of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

As shown in FIG. 10A, a portion of a mu opioid receptor (MOR), a Class A receptor, may be fused to a portion of a V2R receptor (a Class B receptor). Accordingly, the first 351 amino acids of the MOR, Met-1 through Cys-351 (a palmitoylated cysteine residue), were fused to the last 29 amino acid of the V2R carboxyl-terminus (Ala-343 through Ser-371; Ala-343 is immediately following a palmitoylated, cysteine). This fusion properly positions the V2R cluster of phosphorylation sites (SSS) within the modified GPCR's tail.

Also as shown in FIG. 10B, a portion of a dopamine D1A receptor (D1AR), a Class A receptor, may be fused to a portion of a V2R receptor. Accordingly, the first 351 amino acids of the D1AR, Met-1 through Cys-351 (a palmitoylated cysteine) were fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

Further as shown in FIG. 10C, a portion of a 5-hydroxytryptamine 1A receptor (5HT1AR), a Class A receptor, may be fused to a portion of a V2R receptor (a Class B receptor). Accordingly, the first 420 amino acids of the 5HT1AR, Met-1 through Cys-420 (a palmitoylated cysteine) were fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

As shown in FIG. 10D, a portion of a $\beta$3-adrenergic receptor ($\beta$3AR), a Class A receptor, may be fused to a portion of a V2R receptor (a Class B receptor). Accordingly, the first 363 amino acids of the $\beta$3AR, Met-1 through Cys-363 (a palmitoylated cysteine) were fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

Finally as shown in FIG. 10E, a portion of a endothelial differentiation, sphingolipid GPCR 1 (Edg1R), a Class A receptor, may be fused to a portion of a V2R receptor (a Class B receptor). Accordingly, the first 331 amino acids of the Edg1R, Met-1 through Cys-331 (a palmitoylated cysteine) were fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

As may be shown by standard receptor binding assays, the modified receptors are essentially indistinguishable from their wild-type counterparts except for an increased affinity for arrestin and thus an increased stability of their complex with arrestin and in their ability to traffic with arrestin and in their ability to recycle and resensitize. For example, the modified receptors are appropriately expressed at the membrane, possess similar affinity for agonists or ligands, and provide the appropriate downstream signaling in response to agonist activation. However, the modified GPCRs have an increased affinity for arrestin and thus form a more stable complex with arrestin than their wild-type counterparts and may remain bound to arrestin when trafficking to endosomes.

Methods of Assaying GPCR Activity

The modified GPCRs of the present invention are useful in methods of assaying GPCR activity. The modified GPCRs of the present invention may be used in assays to study GPCRs that have weaker than desired interactions or associations with arrestins and GPCRs that have unknown interactions or associations with arrestins. Methods of the present invention that use the modified GPCRs provide a sensitive assay and may provide for enhanced detection, for example, of arrestin/GPCRs in endosomes. The assays using the modified GPCRs of the present invention may be useful for screening compounds and sample solutions for ligands, agonists, antagonists, inverse agonists, desensitization active compounds, and the like. Once identified, these compounds may be useful as drugs capable of modulating GPCR activity and useful in the treatment of one or more of the disease states in which GPCRs have been implicated.

In a preferred assay according to the present invention, cells are provided that express modified GPCRs of the present invention and these cells may further contain a conjugate of an arrestin and a detectable molecule.

Arrestin coupled to a detectable molecule may be detected and monitored as it functions in the GPCR pathway. The location of the arrestin may be detected, for example, evenly distributed in the cell cytoplasm, concentrated at a cell membrane, concentrated in clathrin-coated pits, localized on endosomes, and the like. In response to agonist stimulation, the proximity of arrestin to a GPCR may be monitored, as well as the proximity to any other cell structure. For example, in response to agonist stimulation arrestin may be detected in proximity to GPCRs at a cell membrane, concentrated with GPCRs in clathrin-coated pits, colocalized with a GPCR on endosomes, and the like.

The modified GPCRs of the present invention have an increased affinity for arrestin and provide a stable complex of the GPCR with arrestin, and thereby promote colocalization of the GPCR with arrest in into endosomes. In the methods of assaying of the present invention, arrestin may be detected, for example, in the cytoplasm, concentrated in proximity to GPCRs at a cell membrane, concentrated in proximity to GPCRs in clathrin-coated pits, colocalized with a GPCR on endosomes, and the like. Preferably the arrestin may be detected colocalized with a GPCR on endosomes.

The association of arrestin with a GPCR at a cell membrane may be rapidly detected after agonist addition, for example, approximately 1 second to 2 minutes. The colocalization of arrestin with GPCR on endosomes may be detected within several minutes of agonist addition, for example, approximately 3 to 15 minutes, and may persist for extended periods of time, for example, after 1 hour. The association of arrestin with GPCR on endosomes may give a strong, readily recognizable signal. Under magnification of 40× objective lens, the signal may be doughnut-like in appearance. The signal resulting from the compartmentalization of arrestin and GPCR colocalized in endosomes vesicles is typically easy to detect and may persist for extended periods of time.

A preferred method of assessing GPCR pathway activity of the present invention comprises (a) providing a cell that expresses at least one modified GPCR of the present invention and that further comprises a conjugate of an arrestin and a detectable molecule; (b) inducing translocation of the arrestin; and (c) detecting interaction of the arrestin with the modified GPCR along the translocation pathway.

Interaction of the arrestin with the modified GPCR may be detected, for example, in endosomes, in clathrin-coated pits, concentrated in proximity to a cell membrane, and the like. Preferably, interaction of the arrestin with the modified GPCR is detected in endosomes. Interaction of arrestin with a GPCR in endosomes may be detected within several minutes of agonist addition, for example, approximately 3 to 15 minutes, and may persist for extended periods of time, for example, after 1 hour. The association of arrestin with a GPCR in endosomes may give a strong, readily recognizable signal that persists for extended periods of time.

In a method of screening compounds for GPCR activity of the present invention a cell that expresses at least one modified GPCR is provided. The cell further contains arrestin conjugated to a detectable molecule. The cell is exposed to the compounds to be tested. The location of the arrestin within the cell is detected. The location of the arrestin within the cell in the presence of the compound is compared to the location of the arrestin within the cell in the absence of the compound, and a difference is correlated between (1) the location of the arrestin within the cell in the presence of the compound and (2) the presence of the location of the arrestin within the cell in the absence of the compound.

By way of example, compounds and sample solutions may be screened for GPCR agonist activity using the modified GPCRs of the present invention. In this method, cells that express at least one modified GPCR of the present invention and that further comprise a conjugate of an arrestin and a detectable molecule are provided. The cells are exposed to compounds or sample solutions to be tested. It is detected whether interaction of the arrestin with the modified GPCR is increased after exposure to the test compound or solution, an increase in interaction being an indication that the compound or solution has GPCR agonist activity. Interaction of the arrestin with the GPCR may be detected in endosomes, in clathrin-coated pits, in proximity to a cell membrane, and the like. The modified GPCR may also be conjugated to a detectable molecule, preferably at the carboxyl-terminus. As explained above modifications to GPCRs as in the present invention should not affect the GPCRs natural affinity for agonists or ligands.

Also by way of example, compounds and sample solutions may be screened for GPCR antagonist or inverse agonist activity using the modified GPCRs of the present invention. Cells that express at least one modified GPCR of the present invention and that further comprise a conjugate of an arrestin and a detectable molecule are provided. The cells are exposed to compounds or sample solutions to be tested and to a known agonist for the GPCR. It is detected whether interaction of the arrestin with the modified GPCR is decreased after exposure to the test compound or solution, a decrease in interaction being an indication that the compound or solution has GPCR antagonist or inverse agonist activity. Interaction of the arrestin with the GPCR may be detected in endosomes, in clathrin-coated pits, in proximity to a cell membrane, and the like. The modified GPCR may also be conjugated to a detectable molecule, preferably at the carboxyl-terminus. As explained above modifications to GPCRs as in the present invention should not affect the GPCRs' natural affinity for antagonists or inverse agonists.

Further by way of example, compounds and sample solutions may be screened for GPCR desensitization activity using the modified GPCRs of the present invention. First cells that express at least one first modified GPCR of the present invention and that further comprise a conjugate of an arrestin and a detectable molecule are provided. The first cells are exposed to compounds or sample solutions to be tested and to a known agonist for the first GPCR. It is detected whether interaction of the arrestin with the first modified GPCR is decreased or not increased after exposure to the test compound or solution, a decrease or lack of increase in interaction being an indication that the compound or solution has GPCR desensitization activity. Interaction of the arrestin with the GPCR may be detected in endosomes, in clathrin-coated pits, in proximity to a cell membrane, and the like. Then second cells that express at least one second modified GPCR of the present invention and that further comprise a conjugate of an arrestin and a detectable molecule are provided. The second modified GPCR is not related to the first modified GPCR. The second cells are exposed to the compounds or sample solutions to be tested and to a known agonist for the second GPCR. It is detected whether interaction of the arrestin with the second modified GPCR is decreased or not increased after exposure to the test compound or solution, a decrease or lack of increase in interaction being an indication that the compound or solution has GPCR desensitization activity independent of the GPCR expressed. Interaction of the arrestin with the GPCR may be detected in endosomes, in clathrin-coated pits, in proximity to a cell membrane, and the like. Preferably, the first detection step detects interaction of the arrestin with the GPCR in endosomes and the second detection step detects interaction of the arrestin with the GPCR in clathrin-coated pits or in proximity to a cell membrane.

The methods of assessing GPCR pathway activity of the present invention also include cell-free assays. In cell-free assays of the present invention, a substrate having deposited thereon a modified GPCR of the present invention is provided. A fluid containing a conjugate of an arrestin and a detectable molecule is also provided. Translocation of the arrestin is induced and interaction of the arrestin with the GPCR is detected. The GPCR and arrestin may be obtained from whole cells and used in the cell-free assay after purification. The modified GPCR has arrestin binding sites and agonist binding sites and may be supported in a multilayer or bilayer lipid vesicle. The vesicle supporting the modified GPCR may be deposited on the substrate, and the modified GPCR may be supported in the lipid vesicle and deposited on the substrate such that the arrestin binding sites are exposed to arrestin and the receptor binding sites are accessible to agonists. The substrate may be any artificial substrate on which the GPCR may be deposited, including but not limited to, glass, plastic, diamond, ceramic, semiconductor, silica, fiber optic, diamond, biocompatible monomer, biocompatible polymer, polymer beads (including organic and inorganic polymers), and the like.

The present invention relates to the compounds identified as ligands, agonists, antagonists, inverse agonists, or DACs by the methods of assaying of the present invention. These compounds may be used to treat any one of the disease states in which GPCRs have been implicated. The compounds identified may be administered to a human or a non-human in therapeutically effective doses to treat or ameliorate a condition, disorder, or disease in which GPCRs have been implicated. A therapeutically effective dose refers to that amount of the compound sufficient to result in amelioration of symptoms of such a condition, disorder or disease.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds which exhibit toxic side effects may be used, care should be taken to design a delivery system which targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the compound (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to, the severity of the disease or condition, disorder, or disease, previous treatments, the general health and/or age of the subject, and other diseases present. Moreover, treatment of a subject with a therapeutically effective amount of the compounds can include a single treatment or, preferably, can include a series of treatments. In a preferred example, a subject is treated with the compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the compound used for treatment may increase or decrease over the course of a particular treatment. Changes in dosage may result and become apparent from the results of diagnostic assays as described herein.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The Conjugates

The cells used in the methods of assaying of the present invention may comprise a conjugate of an arrestin protein and a detectable molecule. In the cells and methods of the present invention, the cells may also comprise a conjugate of a modified GPCR of the present invention and a detectable molecule.

All forms of arrestin, naturally occurring and engineered variants, including but not limited to, visual arrestin, β-arrestin 1 and β-arrestin 2, may be used in the present invention. The modified GPCRs of the present invention may interact to a detectable level with all forms of arrestin.

Detectable molecules that maybe used to conjugate with the arrestin include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the ability of the arrestin to interact with the GPCR system and the interaction of the arrestin with the GPCR system must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the arrestin protein by methods as described in Barak et al. (U.S. Pat. Nos. 5,891,646 and 6,110,693). The detectable molecule may be conjugated to the arrestin at the front-end, at the back-end, or in the middle.

The modified GPCRs of the present invention may also be conjugated with a detectable molecule. Preferably, the carboxyl-terminus of the modified GPCR is conjugated with a detectable molecule. A carboxyl-terminal tail conjugated or attached to a detectable molecule can be used in a carboxyl-terminal tail exchange to provide the modified GPCRs of the present invention.

If the GPCR is conjugated with a detectable molecule, proximity of the GPCR with the arrestin may be readily detected. In addition, if the GPCR is conjugated with a detectable molecule, compartmentalization of the GPCR with the arrestin may be readily confirmed. The detectable molecule used to conjugate with the GPCRs may include those as described above, including, for example, optically detectable molecules, such that they may be excited chemically, mechanically, electrically, or radioactively to emit fluorescence, phosphorescence, or bioluminescence. Preferred optically detectable molecules may be detected by immunofluorescence, luminescence, fluorescence, and phosphorescence.

For example, the GPCRs may be antibody labeled with an antibody conjugated to an immunofluorescence molecule or the GPCRs may be conjugated with a luminescent donor. In particular, the GPCRs may be conjugated with, for example, luciferase, for example, Renilla luciferase, or a rhodamine-conjugated antibody, for example, rhodamine-conjugated anti-HA mouse monoclonal antibody. Preferably, the carboxyl-terminal tail of the GPCR may be conjugated with a luminescent donor, for example, luciferase. The GPCR, preferably the carboxyl-terminal tail, also may be conjugated with GFP as described in L. S. Barak et al. Internal Trafficking and Surface Mobility of a Functionally Intact $\beta_2$-Adrenergic Receptor-Green Fluorescent Protein Conjugate, *Mol. Pharm.* (1997) 51, 177–184.

Cell Types and Substrates

The cells of the present invention express at least one modified GPCR of the present invention. The cells may further comprise a conjugate of an arrestin protein and a detectable molecule. Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, and various primary mammalian cells. An animal model expressing a conjugate of an arrestin and a detectable molecule throughout its tissues or within a particular organ or tissue type, may also be used in the present invention.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Methods of Detection

Methods of detecting the intracellular location of the conjugate of arrestin and a detectable molecule, the intracellular location of a GPCR fused to a detectable molecule, or interaction of the arrestin, which is conjugated to a detectable molecule, with a GPCR or any other cell structure, including for example, the concentration of arrestin at a cell membrane, colocalization of arrestin with GPCR in endosomes, and concentration of arrestin in clathrin-coated pits, and the like, will vary dependent upon the detectable molecule(s) used. One skilled in the art readily will be able to devise detection methods suitable for the detectable molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In a preferred embodiment arrestin may be conjugated to GFP and the arrestin-GFP conjugate may be detected by confocal microscopy. In another preferred embodiment, arrestin may conjugated to a GFP and the modified GPCR may be conjugated to an immunofluorescent molecule, and the conjugates may be detected by confocal microscopy. In an additional preferred embodiment, arrestin may conjugated to a GFP and the carboxy-terminus of the GPCR may be conjugated to a luciferase and the conjugates may be detected by bioluminescence resonance emission technology. In a further preferred embodiment arrestin may be conjugated to a luciferase and GPCR may be conjugated to a GFP, and the conjugates may be detected by bioluminescence resonance emission technology. The methods of the present invention are directed to detecting GPCR activity. The methods of the present invention allow enhanced monitoring of the GPCR pathway in real time.

Diagnostic and Therapeutic Treatments

The possibilities of both diagnostic and therapeutic that are raised by the existence of the GPCR derive from the fact that the factors appear to participate in direct and causal protein-protein interaction between a ligand thereto, and those factors that thereafter initiate an intracellular signal. As discussed earlier and elaborated further on herein, the present invention contemplates pharmaceutical intervention in the cascade of reactions in which the GPCR is implicated, to modulate the activity initiated by the GPCR.

Thus, in instances where it is desired to reduce or inhibit the activity resulting from a particular stimulus or factor, an appropriate inhibitor of the GPCR could be introduced to block the interaction of the GPCR with a ligand. Correspondingly, instances in which insufficient activation of a G protein or second messenger is taking place could be remedied by introduction of additional quantities of the GPCR or its chemical or pharmaceutical cognates, analogs, fragments and the like.

As discussed earlier, the GPCRs or their binding partners or other ligands or agents exhibiting either mimicry or antagonism to the GPCRs or control over their production, may be prepared in pharmaceutical compositions, with a suitable carrier and at a strength effective for administration by various means to a patient experiencing an adverse medical condition associated with GPCR activity for the treatment thereof. A variety of administrative techniques may be utilized, among them parenteral techniques such as subcutaneous, intravenous and intraperitoneal injections, catheterizations and the like. Average quantities of the GPCR agonist or antagonist may vary and in particular should be based upon the recommendations and prescription of a qualified physician or veterinarian.

Also, antibodies including both polyclonal and monoclonal antibodies, and drugs that modulate the production or activity of the GPCRs and/or their fragments or subunits may possess certain diagnostic applications and may for example, be utilized for the purpose of detecting and/or measuring conditions such as viral infection or the like. For example, the modified GPCR or fragments or subunits thereof may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the GPCR of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against GPCR peptides can be screened for various properties; i.e., isotype, epitope, affinity, etc. Of particular interest are monoclonal antibodies that neutralize the activity of the GPCR or its subunits. Such monoclonals can be readily identified in GPCR assays. High affinity antibodies are also useful when immunoaffinity purification of native or recombinant modified GPCRs is possible.

Preferably, the anti-GPCR antibody used in the diagnostic methods of this invention is an affinity purified polyclonal antibody. More preferably, the antibody is a monoclonal antibody (mAb). In addition, it is preferable for the anti-GPCR antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a GPCR/protein, such as an anti-GPCR antibody, preferably an affinity-purified polyclonal antibody, and more preferably a mAb. In addition, it is preferable for the anti-GPCR antibody molecules used herein be in the form of Fab, Fab', F(ab')$_2$ or F(v) portions or whole antibody molecules. As previously discussed, patients capable of benefitting from this method include those suffering from cancer, a pre-cancerous lesion, a viral infection or other like pathological derangement. Methods for isolating the GPCR and inducing anti-GPCR antibodies and for determining and optimizing the ability of anti-GPCR antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a GPCR.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present GPCR and their ability to inhibit specified GPCR activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-GPCR antibodies are also well-known in the art. See Niman et al., *Proc. Natl. Acad. Sci. USA*, 80:4949–4953 (1983). Typically, the present GPCR or a peptide analog is used either alone or conjugated to an immunogenic carrier, as the immunogen in the before described procedure for producing anti-GPCR monoclonal antibodies. The hybridomas are screened for the ability to produce an antibody that immunoreacts with the GPCR or peptide analog.

The present invention further contemplates therapeutic compositions useful in practicing the therapeutic methods of this invention. A subject therapeutic composition includes, in admixture, a pharmaceutically acceptable excipient (carrier) and one or more of an agonist, antagonist, or DAC of the GPCR, as described herein as an active ingredient. In a preferred embodiment, the composition comprises a drug capable of modulating the specific binding of the present GPCR with a ligand on a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A GPCR agonist, antagonist, or DAC can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of modulation of GPCR activity desired. Precise amounts of active ingredient required to be administered depend on the judgment of the practitioner and are peculiar to each individual. However, suitable dosages may range from about 0.001 to 30, preferably about 0.01 to about 25, and more preferably about 0.1 to 20 milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the GPCR agonist, antagonist, or DAC and one or more of the following active ingredients: an antibiotic, a steroid, and the like.

Expression of the Modified GPCRs

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, plant cells, nematode cells, and animal cells, such as HEK-293, CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that modified GPCR analogs may be prepared from nucleotide sequences of the protein complex/subunit derived within the scope of the present invention. Analogs, such as fragments, may be produced, for example, by pepsin digestion of GPCR material. Other analogs, such as muteins, can be produced by standard site-directed mutagenesis of GPCR coding sequences. Analogs exhibiting "GPCR activity" such as small molecules, whether functioning as promoters or inhibitors, may be identified by known in vivo and/or in vitro assays.

As mentioned above, a DNA sequence encoding a modified GPCR can be prepared synthetically rather than cloned. The DNA sequence can be designed with the appropriate codons for the GPCR amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express GPCR analogs or "muteins". Alternatively, DNA encoding muteins can be made by site-directed mutagenesis of native or modified GPCR genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182–188 (April 1989). This method may be used to create analogs with unnatural amino acids.

Antisense

The present invention extends to the preparation of antisense oligonucleotides and ribozymes that may be used to interfere with the expression of a modified GPCR at the translational level. Preferably, the antisense and ribozymes may be used to interfere with the expression of a modified GPCR having discrete point mutations that increases its affinity for arrestin in suspect target cells. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, Sci Am. 1990 January;262(1): 40–6; Marcus-Sekura, Anal Biochem. 1988 Aug. 1;172(2): 289–95). In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into GPCR-producing cells. Antisense methods have been used to inhibit the expression of many genes in vitro (Marcus-Sekura, 1988; Hambor et al., J Exp Med. 1988 Oct. 1;168(4):1237–45).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, Gene. 1988 Dec. 20;73(2): 259–71). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for GPCRs and their ligands. In particular, the antisense molecules and ribozymes may be particularly useful for GPCRs having point mutations that increase their affinity for arrestin.

Diagnostic Applications

The present invention also relates to a variety of diagnostic applications, including methods for detecting the presence of stimuli such as the earlier referenced polypeptide ligands, by reference to their ability to elicit the activities which are mediated by the present GPCRs. As mentioned earlier, the GPCRs can be used to produce antibodies to itself by a variety of known techniques, and such antibodies could then be isolated and utilized as in tests for the presence of particular GPCR activity in suspect target cells. In particular, the antibodies may be utilized as in tests for the present of GPCRs having point mutations that increase their affinity for arrestin in suspect target cells.

As described in detail above, antibody(ies) to the GPCR, preferably a GPCR having point mutations that increases its affinity for arrestin, can be produced and isolated by standard methods including the well known hybridoma techniques. For convenience, the antibody(ies) to the GPCR will be referred to herein as $Ab_1$ and antibody(ies) raised in another species as $Ab_2$.

The presence of GPCRs, preferably GPCRs having point mutations that increase their affinity for arrestin, in cells can be ascertained by the usual immunological procedures applicable to such determinations. A number of useful procedures are known. Three such procedures which are especially useful utilize either the GPCR labeled with a detectable label, antibody $Ab_1$ labeled with a detectable label, or antibody $Ab_2$ labeled with a detectable label. The procedures may be summarized by the following equations wherein the asterisk indicates that the particle is labeled:

$$GPCR^* + Ab_1 = GPCR^*Ab_1 \quad \text{A.}$$

$$GPCR + Ab^* = GPCRAb_1^* \quad \text{B.}$$

$$GPCR + Ab_1 + Ab_2^* = GPCRAb_1Ab_2^* \quad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. No. RE 31,006 and U.S. Pat. No. 4,016,043. Still other procedures are known such as the "double antibody," or "DASP" procedure.

In each instance, the GPCR forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-GPCR antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue, GFP and Lucifer Yellow. A particular detecting material is anti-rabbit antibody prepared in goats and conjugated with fluorescein through an isothiocyanate.

The GPCR or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the GPCR may be radiolabeled and combined, for example, with antibodies or other inhibitors thereto, after which binding studies would be carried out. Solutions would then be prepared that contain various quantities of labeled and unlabeled uncombined GPCR, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest (e.g., a GPCR) when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

Test Kits

In a further embodiment of this invention, commercial test kits suitable for use by a medical specialist may be prepared to determine the presence or absence of predetermined GPCR activity or predetermined GPCR activity capability in suspected target cells. In accordance with the testing techniques discussed above, one class of such kits will contain at least the labeled GPCR or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined GPCR activity, comprising:

(a) a predetermined amount of at least one labeled immunochemically reactive component obtained by the direct or indirect attachment of the present GPCR or a specific binding partner thereto, to a detectable label;

(b) other reagents; and (c) directions for use of said kit.

More specifically, the diagnostic test kit may comprise:

(a) a known amount of the GPCR as described above (or a binding partner, or in the alternative, bound to a suitable tag, or plural such end products, etc. (or their binding partners) one of each, (b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the GPCR to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the GPCR and a specific binding partner thereto.

In accordance with the above, an assay system for screening potential drugs effective to modulate the activity of the GPCR may be prepared. The modified GPCRs may be introduced into a test system, and the prospective drug may also be introduced into the resulting cell culture, and the culture thereafter examined to observe any changes in the GPCR activity (e.g., signaling, recycling, affinity for arrestin, and the like) in the cells.

The following examples are presented in order to more fully illustrate the preferred embodiments of the invention. They should in no way be construed, however, as limiting the broad scope of the invention.

EXAMPLES

The invention will be further explained by the following illustrative examples which are intended to be non-limiting.

Materials—Isoproterenol and arginine vasopressin (AVP) were obtained from Sigma Chemicals (St. Louis, Mo.). The anti-HA 12CA5 mouse monoclonal antibody and the rhodamine-conjugated anti-HA 12CA5 mouse monoclonal antibody were purchased from Roche Molecular Biochemicals (Indianapolis, Ind.). [$^{125}$I]Cyanopindolol, [$^{3}$H]AVP, [$^{3}$H]adenine, [$^{14}$C]cAMP, [$^{32}$P]ATP, [$^{3}$H]ATP, [$^{3}$H]cAMP, and [$^{32}$P]orthophosphate were purchased from NEN Life Science Products (Boston, Mass.). The HA-tagged V2R cDNA was kindly provided by Dr. Jurgen Wess (National Institutes of Health, Bethesda, Md.).

Cell Culture and Transfection—HEK-293 and COS-7 cells were grown as described in Ferguson, S. S. G., Menard, L., Barak, L. S., Koch, W. J., Colapietro, A. M., and Caron, M. G. (1995), *J. Biol. Chem.*, 270:24782–24789. The cells were seeded at a density of $2 \times 10^6$ cells/100-min dish and $5 \times 10^5$ cells/100-mm. dish, respectively. Transient transfections were performed using a modified calcium phosphate co-precipitation method as described in Ferguson et al., *J. Biol. Chem.*, 270:24782–24789.

Data Analysis—The mean and standard error of the mean were expressed for values obtained from the number of independent experiments indicated. Statistical significance was determined using a two-tailed t test. Binding and dose-response data were analyzed using GraphPad Prism software.

Example 1

Construction of Plasmid DNA

Construction of plasmids containing the hemagglutinin epitope (HA)-tagged $\beta_2$AR, $\beta$arr2-GFP, $\beta$arr1-GFP, $\beta$-arrestin1, and $\beta$-arrestin2 as described in Ferguson, S. S., Downey, W. E., 3$^{rd}$, Colapietro, A. M., Barak, L. S., Menard, L., and Caron, M. G. (1996) *Science,* 271:363–366; Zhang, J., Barak, L. S., Anborgh, P. H., Laporte, S. A., Caron, M. G., and Ferguson, S. S. (1999) *J. Biol. Chem.,* 274:10999–11006; Barak, L. S., Tiberi, M., Freedman, N. J., Kwatra, M. M., Lefkowitz, R. J., and Caron, M. G. (1994) *J. Biol. Chem.,* 269:2790–2795; Barak, L. S., Ferguson, S. S., Zhang, J., and Caron, M. G. (1997) *J. Biol. Chem.,* 272:27497–27500.

Other constructs were generated by polymerase chain reaction following standard protocols and contain the HA epitope. Chimeric receptors were constructed in which the carboxyl-terminal tails of the $\beta_2$AR and V2R were exchanged (FIG. 9, A and B), one for the other, after the putative sites of palmitoylation. The $\beta_2$AR-V2R chimera contains the first 341 amino acids of the $\beta_2$AR (Met-1 to Cys-341) fused to the last 29 amino acids of the V2R (Ala-343 to Ser-371) (FIG. 9C, Seq ID No.3). The V2R-$\beta_2$AR chimera contains the first 342 amino acids of the V2R (Met-1 to Cys-342) fused to the last 72 amino acids of the $\beta_2$AR (Leu-342 to Leu-413). The V2R-S362X truncation mutant was generated by replacing nucleotides CCG encoding Ser-362 of the V2R with nucleotides TAA encoding a stop codon. The V2R-SSSTSS/AAAAAA mutant was generated by replacing Ser-362, Ser-363, Ser-364, Thr-369, Ser-370, and Ser-371 of the V2R with alanine residues. The V2R-TSS/AAA mutant was generated by replacing Thr-369, Ser-370, and Ser-371 of the V2R with alanine residues. The V2R-SSS/AAA and $\beta$2Ar-V2R-SSS/AAA mutants were generated by replacing Ser-362, Ser-363, and Ser-364 of the V2R with alanine residues. The $\beta$2AR413-V2R10 chimera contains the full-length $\beta_2$AR (Met-1 to Leu-413) fused to the last 10 amino acids of the V2R (Ser-362 to Ser-371). The $\beta_2$AR360-V2R10 chimera contains the first 360 amino acids of the $\beta_2$AR (Met-1 to Thr-360) fused to the last 10 amino acids of the V2R (Ser-362 to Ser-371). Sequences of the DNA constructs were confirmed by DNA sequencing.

The pEArrB-1 Vector:

The pEArrB (enhanced arrestin binding) vectors were designed to enhance the affinity of the GPCR/arrestin interaction by modifying the receptor carboxyl terminus. The modification involves fusing a portion of the carboxyl terminus of a class B receptor, such as the vasopressin V2 receptor (V2R), neurotensin-1 receptor (NTR-1), or substance P receptor (SPR), to selected sites within the carboxyl terminus of the GPCR of interest, preferably immediately downstream of a palmitoylated cysteine 10 to 25 (preferably 15 to 20) amino acids downstream of the NPXXY. For example, the pEArrB-1 vector fuses the last 29 amino acids of the human V2R carboxyl terminus (Ala-343 through Ser-371) to the GPCR of interest.

The nucleic acids encoding the last 29 amino acids of the human V2R carboxyl terminus and the adjacent stop codon were amplified using specific PCR primers that introduced the following changes to the amplified DNA fragment (FIG. 3, A and B). First, three restriction enzyme sites (Bgl II, Sac II, and Xba I) were added to the 3' end of the DNA fragment immediately downstream of the stop codon. Second, a Not I restriction site (sequence=gcggccgc) was incorporated into the 5' end of the DNA fragment such that the last two nucleic acids in the Not I site (gc) are contributed by the first two nucleic acids of the V2R DNA fragment. Finally, the first codon of the V2R DNA fragment (gcc) was changed (gca) to eliminate a Sma I restriction site but preserve the encoded amino acid (Ala-343).

The PCR-amplified V2R DNA fragment (FIG. 3B) was digested with Not I and Xba I restriction enzymes and cloned into the pcDNA3.1zeo+ vector (Invitrogen) that was also digested with the Not I and Xba I restriction enzymes. A schematic of the resulting pEArrB-1 vector is shown in FIG. 4A.

Generation of Modified GPCRs with Enhanced Affinity for Arrestin Using the pEArrB-1 Vector:

The nucleic acids of the GPCR of interest were PCR-amplified with primers that introduced a Not I restriction enzyme site (gcggccgc) immediately after the codon for a cysteine residue (a putative site of palmitoylation) 10 to 25 amino acids (preferably 15 to 20) downstream of the NPXXY (SEQ ID NO: 82) that is to be fused to the V2R carboxyl terminus. The amplified receptor DNA fragment was then subcloned into the pEArrB-1 vector using the Not I restriction enzyme site and an additional restriction enzyme site upstream of the receptor atg start codon. A schematic of the resulting pEArrB-1/GPCR vector is shown in FIG. 4B. When expressed, the modified GPCR will contain a 31 amino acid peptide fused to the receptor carboxyl terminus. The first two amino acids will be Ala residues contributed by the Not I site, and the last 29 amino acids will be from the V2R carboxyl terminus (see FIG. 4C).

For the MOR-V2R construct, the MOR nucleic acids encoding the first 351 amino acids of the receptor were PCR-amplified with primers that introduced a Not I restriction enzyme site (gcggccgc) immediately after the codon for Cys-351. The amplified receptor DNA fragment was then subcloned into the pEArrB-1 vector using the Not I restriction enzyme site and an EcoR I restriction enzyme site upstream of the receptor atg start codon.

For the D1AR-V2R construct, the D1AR nucleic acids encoding the first 351 amino acids of the receptor were PCR-amplified with primers that introduced a Not I restriction enzyme site (gcggccgc) immediately after the codon for Cys-351. The amplified receptor DNA fragment was then subcloned into the pEArrB-1 vector using the Not I restriction enzyme site and an BamH I restriction enzyme site upstream of the receptor atg start codon.

For the 5HT1AR-V2R construct, the 5HT1AR nucleic acids encoding the first 420 amino acids of the receptor were PCR-amplified with primers that introduced a Not I restriction enzyme site (gcggccgc) immediately after the codon for Cys-420. The amplified receptor DNA fragment was then subcloned into the pEArrB-1 vector using the Not I restriction enzyme site and an EcoR I restriction enzyme site upstream of the receptor atg start codon.

For the $\beta$3AR-V2R construct, the $\beta$3AR nucleic acids encoding the first 363 amino acids of the receptor were PCR-amplified with primers that introduced a Not I restriction enzyme site (gcggccgc) immediately after the codon for Cys-363. The amplified receptor DNA fragment was then subcloned into the pEArrB-1 vector using the Not I restriction enzyme site and an EcoR I restriction enzyme site upstream of the receptor atg start codon.

For the Edg1R-V2R construct, the Edg1R nucleic acids encoding the first 331 amino acids of the receptor were PCR-amplified with primers that introduced a Not I restriction enzyme site (gcggccgc) immediately after the codon for Cys-331. The amplified receptor DNA fragment was then subcloned into the pEArrB-1 vector using the Not I restriction enzyme site and a BamH I restriction enzyme site upstream of the receptor atg start codon.

Example 2

Quantitative Measures of Receptor Binding, Sequestration, Recycling, and Resensitization of $\beta_2AR$, V2R, V2R-$\beta_2AR$, and $\beta_2AR$-V2R Chimeras A. Receptor Binding Receptor binding assays demonstrated that the chimeric receptors were essentially indistinguishable from their wild-type counterparts with respect to their affinity for agonist and level of expression.

Wild-type and chimeric receptor expression levels were measured on whole cells as described in Ferguson et al., *J. Biol. Chem.*, 270:24782–24789. Transfected HEK-293 cells expressing the V2R and V2R-$\beta_2AR$ chimera were incubated 2 h on ice in PBS containing 2% BSA with a saturating concentration of [$^3$H]AVP, and bound radioactivity was extracted with 0.1 M NaOH. Nonspecific binding was determined under each respective conditions in the presence of 10 μM propranolol, or 10 μm unlabeled AVP. Receptor expression levels varied between 2000 and 4000 fmol/mg of whole cell protein for experiments with βarr2-GFP and between 500 and 1500 fmol/mg of whole cell protein for all other experiments.

Method for Membrane Binding Assay:

To analyze receptor affinity for agonist, membrane binding assays were performed as described in Hausdorff, W. P., Hnatowich, M., O'Dowd, B. F., Caron, M. G., and Lefkowitz, R. J., (1990) *J. Biol. Chem.* 265, 1388–1393. The affinities of $\beta_2AR$ and $\beta_2AR$-V2R for the $\beta_2AR$ agonist, isoproterenol, were measured by determining the decrease in [$^{125}$I]cyanopindolol (another $\beta_2AR$ agonist) bound to membrane proteins in the presence of increasing concentrations of isoproterenol; the affinities of V2R and V2R-$\beta_2AR$ for the V2R agonist AVP were determined by quantitating [$^3$H]AVP bound to membrane proteins. Membrane proteins (2 μg) from transfected HEK-293 cells expressing the $\beta_2AR$ and $\beta_2AR$-V2R chimera were incubated in phosphate-buffered saline (PBS) containing 0.1% bovine serum albumin (BSA) at room temperature in the presence of 15 pM [$^{125}$I]cyanopindolol and increasing concentrations of isoproterenol (10 pM to 30 μM). Membrane proteins (10 μg) from transfected HEK-293 cells expressing the V2R and V2R-$\beta_2AR$ chimera were incubated in PBS containing 2% BSA at room temperature with increasing concentrations of [$^3$H]AVP (0.5 nM to 16.0 nM). Binding was terminated by rapid filtration and consecutive washes with ice-cold wash buffer (120 mM NaCl, 50 mM Tris-HCl, pH=7.2).

B. Receptor Sequestration

The dependence of receptor sequestration on β-arrestin and clathrin-mediated endocytosis was assessed, demonstrating that the $\beta_2AR$, V2R, and their chimeras all internalize in a β-arrestin and clathrin-mediated endocytosis pathway. Each receptor was transfected into HEK-293 cells, either alone, with the β-arrestin1 dominant negative mutant V53D (V53D) which blocks β2AR sequestration (34), or with the dynaminI dominant negative mutant K44A (K44A) which blocks clathrin-mediated endocytosis (34). Receptor sequestration, defined as the removal of cell surface receptors from the plasma membrane after exposure to agonist, renders receptors inaccessible to antibodies from outside the cell, and thus was assessed by flow cytometry as described in Barak, L. S., Tiberi, M., Freedman, N. J., Kwatra, M. M., Lefkowitz, R. J., and Caron M. G. (1994) *J. Bio. Chem.* 269:2790–2795. Agonist-induced sequestration of the $\beta_2AR$, V2R, and their chimeras was blocked by overexpression of V53D or K44A, indicating β-arrestin dependence and clathrin-mediated endocytosis, respectively.

C. Recycling of the $\beta_2AR$, V2R, and $\beta_2AR$-V2R Chimeras

Comparisons of the recycling of internalized β-arrestin-free and β-arrestin-complexed receptors revealed that receptors free of β-arrestin remained internalized, whereas receptors complexed with β-arrestin recycled back to the plasma membrane.

Transfected HEK-293 cells were treated with agonist for a period of 30 min to promote receptor sequestration. Agonist was then removed and, after sixty minutes, flow cytometry analyses measured the return of sequestered receptors to the cell surface. 65±6% of the internalized $\beta_2AR$ (free of β-arrestin) recycled back to the plasma membrane, whereas only 23±5% of the internalized V2R (complexed with β-arrestin) recycled back to the membrane. By switching the carboxyl-terminal tails of the $\beta_2AR$ and V2R and thus altering their ability to recruit β-arrestin into endocytic vesicles, the ability of these two receptors to recycle was reversed: 89±7% of the internalized V2R-$\beta_2AR$ chimera (free of β-arrestin), but only 11±4% of the internalized $\beta_2AR$-V2R chimera (complexed with β-arrestin) recycled back to the plasma membrane.

Method for Recycling Assay:

Flow cytometry, as described in Barak, L. S., Tiberi, M., Freedman, N. J., Kwatra, M. M., Lefkowitz, R. J., and Caron M. G. (1994) *J. Bio. Chem.* 269:2790–2795.

D. Resensitization of the $\beta_2AR$, V2R, and $\beta_2AR$-V2R Chimeras

Resensitization, the regain of the ability to respond to agonist, was determined for the different transfected cells by measuring adenylyl cyclase activity (adenylyl cyclase activity is a downstream result of agonist binding GPCR). Cells containing β-arrestin-free receptors were fully resensitized, whereas cells containing receptors complexed with β-arrestin were impaired in their resensitization.

Receptor-expressing HEK-293 cells were treated with vehicle for 15 min (Naive), with agonist for 15 min (Desensitized), or with agonist for 15 min and allowed to recover for 60 min in agonist-free medium (Resensitized). Cell membranes were then prepared and agonist-mediated adenylyl cyclase activity was measured for each condition. For both the $\beta_2AR$ and $\beta_2AR$-V2R chimera, desensitization was characterized by a decrease in the maximal velocity ($V_{max}$) of adenylyl cyclase activity. One hour after agonist removal, the $\beta_2AR$ had fully resensitized as indicated by the complete recovery in $V_{max}$ (100±3% of $V_{max}$ measured under Naive conditions). In contrast, recovery of the $V_{max}$ for the $\beta_2AR$-V2R chimera was impaired by 66±3%.

Similar results were obtained for the V2R and V2R-$\beta_2AR$ chimera. Desensitization was characterized for both receptors by decrease $V_{max}$ and a rightward shift in the $EC_{50}$. One hour after agonist removal, the V2R-$\beta_2AR$ chimera fully resensitized as indicated by the complete recovery in $V_{max}$ (102±2% of $V_{max}$ measured under Naive conditions). In contrast, recovery of the $V_{max}$ for the V2R was impaired by 54±1%. Thus, differences in the ability of the wild-type and chimeric receptors to interact with β-arrestin and to recycle lead to corresponding differences in the ability of these receptors to resensitize and re-establish agonist responsiveness.

Method for Cyclase Assay:

Whole cell cyclase assays were performed on transfected HEK-293 cells using varying concentrations of isoproterenol ($1\times10^{-12}$ M to $1\times10^{-5}$ M) or AVP ($1\times10^{-12}$ M to $1\times10^{-5}$ M) as described in Zhang, J., Barak, L. S., Winkler, K. E., Caron, M. G., and Ferguson, S. S. G. (1997) *J. Biol. Chem.*, 272: 27005–27014. For membrane adenylyl cyclase assays, transfected HEK-293 cells were harvested by scraping in ice-cold lysis buffer (10 nM Tris-HCl, 5 mM EDTA, pH=7.4) and membranes were prepared by disruption with a Polytron homogenizer for 20 s at 20,000 rpm followed by centrifugation at 40,000×g. The cell membrane was resuspended in lysis buffer by Polytron homogenization for 15 s at 20,000 rpm, centrifuged, and resuspended in ice-cold assay buffer (75 mM Tris-HCl, 2 mM EDTA, 15 mM $MgCl_2$, pH=7.4) to a final concentration of 1–2 µg/µl membrane protein. Equivalent amounts of membrane protein in 20-µl aliquots, were assayed for agonist-stimulated adenylyl cyclase activity in a final volume of 50 µl as described in Zhang, J. et al. *J. Biol. Chem.*, 272: 27005–27014.

Example 3

Visualization of βarr-GRP Trafficking

βarr Association with β2AR vs V2R in Presence and Absence of Agonist

By confocal microscopy, the trafficking of βarr2-GFP and the co-trafficking with $β_2AR$ or V2R (detected with GPCR-fluorescent antibodies) were visualized. These experiments demonstrated that 1.) β-arrestin binds β2AR and V2R at the plasma membrane, 2.) the β-arrestin dissociates from the β2AR at or close to the plasma membrane and is absent from endocytic vesicles containing β2AR, whereas, 3.) the βarr remains associated with the V2R in the endocytic vesicles. 4.) The βarr/V2R complex remains in the vesicles. 5.) The β2AR recycles to the plasma membrane. 6.) The βarr association is mediated by the C-terminal tail of the GPCR.

β-Arrestin Internalization into Endocytic Vesicles Visualized with Arr-GFP

To determine whether β-arrestin internalized into endocytic vesicles, agonist-induced redistribution of the receptor and βarr2-GFP in the same living HEK-293 cell was examined. The homogenous βarr2-GFP fluorescence indicates the even distribution of βarr2-GFP, in the absence of agonist, throughout the cytoplasm of cells expressing either the $β_2AR$ or the V2R (FIG. 5, A and C, 0 min). Rapid redistribution of βarr2-GFP from the cytosol to the $β_2AR$ at the plasma membrane was promoted by the addition of isoproterenol (FIG. 5A, 2 min). The punctate pattern of βarr2-GFP fluorescence at the plasma membrane reflects its localization with the receptor in clathrin-coated pits.

Upon activation of the V2R with AVP, βarr2-GFP rapidly redistributed from the cytoplasm to the receptor and with the plasma membrane in the same time frame and with the same punctate pattern as that observed for the $β_2AR$ (FIG. 5C, 2 min).

Figure 15:
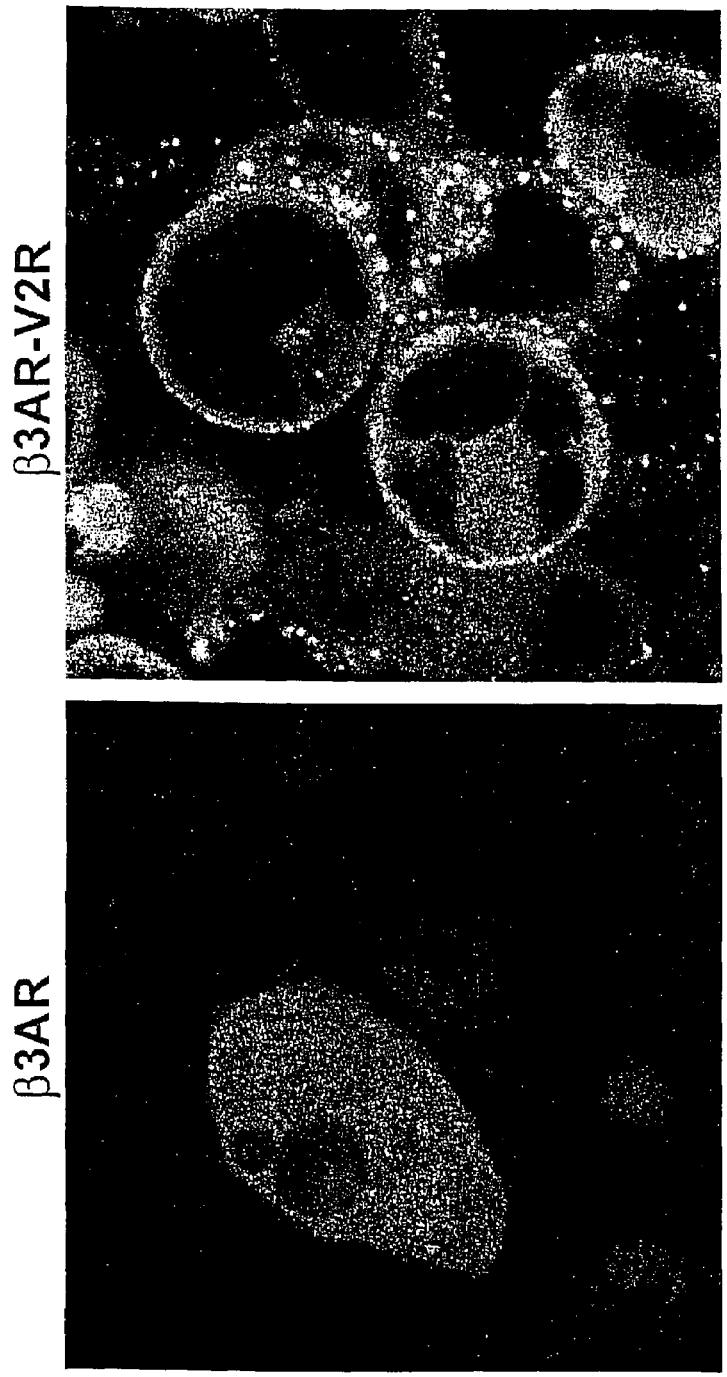
FIG. 15 shows the βarr2-GFP translocation to the $\beta_3$AR and $\beta_3$AR-V2R chimera in response to isoproterenol.

Striking differences in the trafficking of β-arrestin were observed upon a more prolonged exposure to the agonist. In cells expressing the V2R, βarr2-GFP redistributed to endocytic vesicles within 3 to 15 min of agonist stimulation and remained in these vesicles even after 1 h of agonist treatment (FIG. 5C, 15 min). In contrast, in cells expressing the $β_2AR$, βarr2-GFP remained at the plasma membrane even after 1 h of agonist treatment (FIG. 5A, 15 min). However, when the carboxyl-terminal tails of these two receptors were switched to form $β_2AR$-V2R and V2R-$β_2AR$ chimeras, βarr2-GFP localized according to the carboxyl-terminal tails. In cells expressing the $β_2AR$-V2R chimera, βarr2-GFP redistributed to endocytic vesicles in cells, whereas βarr2-GFP remained at the plasma membrane in cells expressing the V2R-$β_2AR$ chimera (FIG. 5, B and D, compare 15 min. images). Similar results were found using a functional βarr1-GFP.

β-Arrestin Cotrafficking with Receptors upon Agonist-induction

Redistribution of the receptor and βarr2-GFP in the same living HEK-293 cell was examined, upon agonist-induction, to determine whether β-arrestin colocalized with the receptors in endocytic vesicles. Cell surface receptors were pre-labeled with fluorescent antibodies prior to agonist stimulation.

The V2R-β-arrestin complex remains intact and is internalized into endocytic vesicles: following 15-min of stimulation with agonist, an extensive colocalization (yellow) of the V2R immunofluorescence (red) and the βarr2-GFP fluorescence (green) was observed in endocytic vesicles (FIG. 6C). In contrast, the $β_2AR$-β-arrestin complex dissociates at or close to the plasma membrane, and β-arrestin is excluded from receptor-bearing endocytic vesicles: βarr2-GFP fluorescence (green) did not colocalize with $β_2AR$ immunofluorescence (red) emanating from endocytic vesicles (FIG. 6A).

Switching the carboxyl-terminal tails of these two receptors completely reversed these phenotypes. βarr2-GFP colocalized with the $β_2AR$-V2R chimera in endocytic vesicles but did not colocalize with vesicles containing the V2R-$β_2AR$ chimera (FIG. 6, B and D). Similar results were found using a functional βarr1-GFP.

These results demonstrate that the endocytic pathways of the $β_2AR$ and V2R share a common recruitment of β-arrestin to the receptor at the plasma membrane during the initial stages of clathrin-mediated endocytosis but then diverge. Moreover, these results demonstrate that the differential trafficking of β-arrestin to endosomes is mediated by the carboxyl-terminal tails of these two receptors. The ability of arrestin-GFP to remain associated with the receptor and traffic with it into endocytic vesicles markedly enhances the ability to detect receptor acitivity and provides a more sensitive assay.

βarr2-GFP Trafficking Following Agonist Removal

The fate of βarr2-GFP following agonist removal was also examined in the wild-type and chimeric receptors. β-arrestin remains associated, even 1 hour after agonist removal, in endocytic vesicles with the V2R and the $β_2AR$-V2R chimera. The stable interaction, of β-arrestin with the V2R carboxy-terminal tail, and trafficking into endocytic vesicles provides: 1.) a signal that enhances the ability to detect agonist-activation of the receptor, and 2) a signal of greater duration, thus providing a sensitive assay. Also, $β_2AR$ and the V2R-$β_2AR$ chimera have a reduced affinity interaction and β-arrestin does not traffic with the $β_2AR$ and V2R-$β_2AR$ chimera into endocytic vesicles.

Figure 7A:
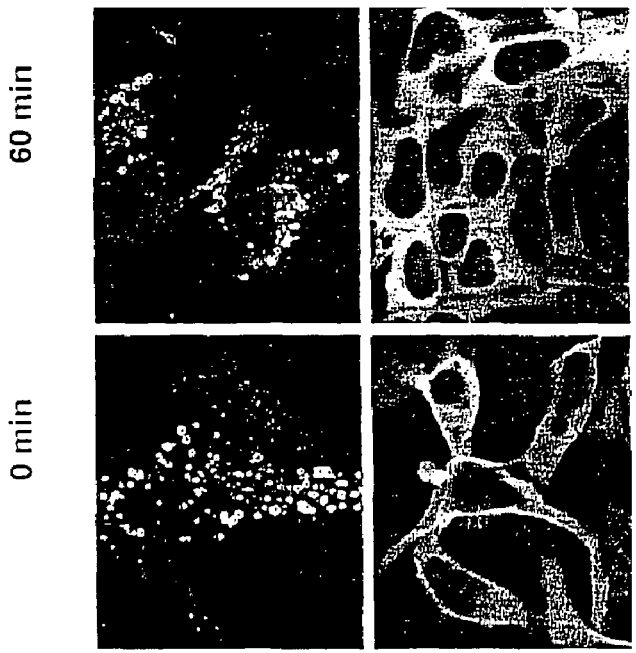
FIG. 7 illustrates receptor recycling and redistribution of βarr-2-GFP following agonist removal. The distribution of βarr-2-GFP fluorescence was visualized in cells immediately before agonist removal (0 min.) and immediately after the 60 min. recovery period (60 min.).
Figure 7B:
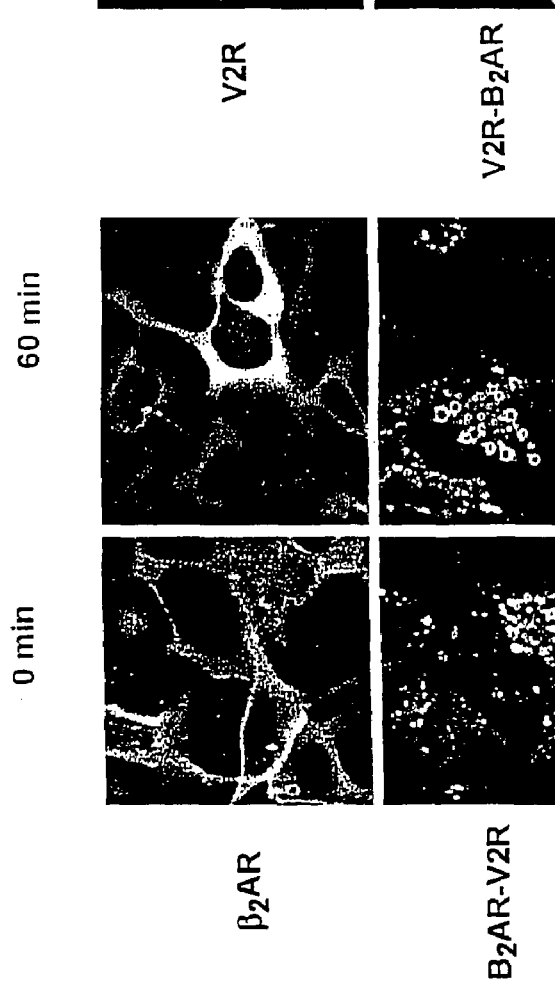

After a 30-min treatment with agonist, βarr2-GFP fluorescence was observed in a punctate pattern at the plasma membrane of cells expressing the $β_2AR$ and V2R-$β_2AR$ chimera, but localized to endocytic vesicles in cells expressing the V2R and $β_2AR$-V2R chimera (FIG. 7, A and B, 0 min).

The cells were then washed to remove agonist, and βarr2-GFP fluorescence was re-evaluated after a 60-min recovery period. In cells expressing the $β_2AR$ and V2R-$β_2AR$ chimera, βarr2-GFP redistributed from the plasma membrane back to the cytoplasm, as reflected by the homogeneous βarr2-GFP fluorescence (FIG. 7, A and B, 60 min).

In contrast, in cells expressing the V2R and $β_2AR$-V2R chimera, βarr2-GFP remained localized with the receptor in endocytic vesicles (FIG. 7, A and B, 60 min).

Method for Confocal Microscopy:

βarr2-GFP trafficking was visualized in transfected HEK-293 cells on a heated (37° C.) microscope stage as described in Barak, L. S., Ferguson, S. S., Zhang, J., and Caron, M. G. (1997) *J. Biol. Chem.*, 272:27497–27500. Images were collected sequentially using single line excitation (488 nm) with a Zeiss laser scanning confocal microscope (LSM-510). For experiments assessing βarr2-GFP trafficking after agonist removal, cells were washed as described above to remove agonist and returned to a 37° C. incubator for 60 min. Colocalization of βarr2-GFP with rhodamine-labeled receptors was performed on transfected cells pre-incubated in serum-free medium containing a rhodamine-conjugated anti-HA 12CA5 mouse monoclonal antibody (1:100) for 45 min. at 37° C. Cells were then washed three times with serum-free medium, treated with the appropriate agonist at 37° C. for 30 min, and imaged by confocal microscopy. βarr2-GFP and rhodamine-labeled receptor fluorescence were performed using dual excitation (488, 568 nm) and emission (515–540 nm, GFP; 590–610 nm, rhodamine) filter sets.

Example 4

Receptor Phosphorylation and Dephosphorylation Dependence on βarr Association

The dephosphorylation of the phosphorylated GPCR was analyzed to determine the effect of βarr association on dephosphorylation of the GPCR. βarr association prevented proper dephosphorylation of the GPCR, as demonstrated by the lack of dephosphorylation of the V2R and $β_2AR$-V2R receptors, but marked dephosphorylation of the $β_2AR$ and $β_2AR$-V2R receptors. Cells were grown in the presence of [$^{32}P$]orthophosphate, resulting in $^{32}P$-labeling of the GPCRs upon agonist stimulation. After agonist removal, the dephosphorylation could then be monitored. GPCRs were immunoprecipitated, equivalent amounts of protein separated on SDS gels, and $^{32}P$ incorporation was quantitated by autoradiography.

Each of the-wild-type and chimeric receptors expressed in HEK-293 cells were phosphorylated after 10 min of agonist treatment. To assess the rate of receptor dephosphorylation, receptor-expressing cells were treated for 10 min with agonist, washed to remove agonist, and either maintained on ice (Desensitized) or returned to a 37° C. incubator for 30 or 60 min (Resensitized). A 48±5% reduction in the phosphorylation of the $β_2AR$ and a 67±7% reduction in the phosphorylation of the V2R-$β_2AR$ chimera were observed 60 min after agonist removal. In contrast, very little dephosphorylation was observed for the V2R (3±6% decrease) and no dephosphorylation was observed for the $β_2AR$-V2R chimera (12±13% increase) after the 60-min recovery period. These data suggest that the stability of the β-arrestin interaction with the carboxyl-terminal tail of GPCRs dictates the rate of receptor dephosphorylation.

Method of Whole Cell Phosphorylation—Receptor phosphorylation was performed as described in Zhang, J., Barak, L. S., Winkler, K. E., Caron, M. G., and Ferguson, S. S. G. (1997) *J. Biol. Chem.*, 272:27005–27014. In brief, transfected HEK-293 cells were labeled for 1 h at 37° C. with [$^{32}P$]orthophosphate (100 μCi/ml) in phosphate-free medium. Cells were stimulated with agonist for 10 min at 37° C. and then washed three times on ice with ice-cold PBS. For resensitization experiments, cells were washed to remove agonist as described above and either maintained on ice or allowed to recover at 37° C. All cells were scraped in radioimmune precipitation buffer (150 mM NaCl, 50 mM Tris, 5 mM EDTA, 10 mM NaF, 10 mM disodium pyrophosphate, 1% Nonidet P-40, 0.5% deoxycholate, 0.1% SDS) containing protease inhibitors and solubilized for 1 h at 4° C. After centrifugation, supernatants were collected and assayed for protein concentration (Bio-Rad DC protein assay kit). HA-tagged receptors were immunoprecipitated at 4° C. using the anti-HA 12CA5 mouse monoclonal antibody. Equivalent amounts of receptor, as determined by receptor expression and the amount of solubilized protein in each sample, were subjected to SDS-polyacrylamide gel electrophoresis and processed for autoradiography. Receptor phosphorylation was quantitated using a Molecular Dynamics PhosphorImager and ImageQuant software.

Example 5

Identification of Residues within the V2R Carboxyl Terminus that Allow β-Arrestin to Remain Associated with Receptors in Endocytic Vesicles To identify residues in the V2R tail that stabilize the receptor's interaction with β-arrestin, mutations were made in the putative phosphate acceptor sites (FIG. 8A). Mutations of the phosphate acceptor sites prevented β-arrestin trafficking to the endocytic vesicles with the mutant receptor.

These mutant receptors expressed in HEK-293 cells sequestered to levels similar to that observed for the wild-type V2R and induced translocation of βarr2-GFP to the plasma membrane upon agonist activation. Removal of the two clusters of serine/threonine residues contained within the last 10 amino acids of the V2R tail, either by truncation or alanine substitution, produced mutant receptors (V2R-S362X and V2R-SSSTSS/AAAAA) that did not recruit β-arrestin into endocytic vesicles. Removal of the cluster of serine/threonine residues at the end of the V2R tail by alanine substitution produced a mutant receptor (V2R-TSS/AAA) that still recruited β-arrestin into endocytic vesicles. However, removal of the more proximal cluster of serine residues (Ser-362, Ser-363, and Ser-364) by alanine substitution produced a mutant receptor (V2RSSS/AAA) that failed to recruit β-arrestin into endocytic vesicles.

Similar results were found when thus V2R serine cluster was mutated to alanines in the $β_2AR$-V2R chimera ($β_2AR$-V2R-SSS/AAA). The importance of this serine cluster for recruiting β-arrestin into endocytic vesicles was further tested by adding only the last 10 amino acids of the V2R to the end of the full-length $β_2AR$. βarr2-GFP translocated to this mutant receptor ($β_2AR413$-V2R10) at the plasma membrane upon agonist activation but did not internalize with the receptor into endocytic vesicles. Similar results were found when the last 29 amino acids of the V2R were added to the end of the full-length β$_2$AR.

However, when the last 10 amino acids of the V2R were positioned closer to the putative palmitoylated cysteine of the β$_2$AR, the mutant receptor β$_2$AR360-V2R10 gained the ability to recruit β-arrestin into endocytic vesicles. These findings identify a cluster of three serine residues located in the V2R carboxyl terminus that mediate the trafficking of β-arrestin with the V2R into endocytic vesicles. Moreover, they suggest that the position of the serine cluster within the receptor carboxyl-terminal tail is critical for the formation of a stable receptor-β-arrestin complex that internalizes into endocytic vesicles.

Whole cell phosphorylation assays were performed on HEK-293 cells expressing the wild-type or mutant V2Rs in order to assess whether the proximal cluster of three serine residues is actually phosphorylated. Agonist-induced phosphorylation of the V2R-SSSTSS/AAAAAA mutant, in which both the proximal and distal clusters of serine/ threopine residues were mutated, was reduced 86.3±1.4% compared with the wild-type V2R. Agonist-induced phosphorylation of the V2R-TSS/AAA mutant, in which only the distal cluster of serine/threonine residues was mutated, was reduced 4.7±6.9%. However, agonist-induced phosphorylation of the V2R-SSS/AAA mutant, in which only the proximal cluster of three serine residues was mutated, was reduced 84.2±0.6%. Therefore, the proximal cluster of three serine residues, which mediates the formation of stable V2R-βarrestin complexes that internalize into endocytic vesicles, was the principal site of V2R phosphorylation.

Example 6

Identification of Residues within the Carboxyl Terminus that Allow β-Arrestin to Remain Associated with Other Receptors in Endocytic Vesicles Mutations in the phosphate acceptors of other GPCRs with serine/threonine sites downstream of putative palmitoylation sites also prevented βarr trafficking to endocytic vesicles. The possible phosphorylation sites of NTR-1, OTR, and SPR, other GPCRs with serine/threonine clusters which are downstream of putative sites of palmitoylation, were mutated to alanine residues as for V2R (FIG. 8B). Upon agonist stimulation of HEK-293 cells which were transiently transfected with βarr2-GFP, βarr redistributed to the endocytic vesicles with wild-type NTR-1, OTR, and SPR. The NTR1-SMSS/AMAA mutant does not alter the ability of βarr to traffic with the receptor to the endocytic vesicles. However, β-arrestin does not traffic to the endocytic vesicles with the NTR1-SSS/AAA mutant receptor. The OTR-TSAS/AAAA mutant does not prevent β-arrestin trafficking into the endocytic vesicles. However, βarr does not traffic to the endocytic vesicles with either the OTR-SSS/AAA-1 or the OTR-SSS/AAA-2 mutants. The SPR-TPSS/APAA mutant does not alter the ability of βarr to traffic with the receptor to the endocytic vesicles. However, βarr's ability to traffic to the endocytic vesicles was impaired with the SPR-TTIST/AAIAA mutant.

To determine whether the identified serine/threonine clusters are actually phosphorylated, whole cell phosphorylation assays were performed on HEK-293 cells expressing the wild-type or mutant NTR-1 or OTR. Agonist-induced phosphorylation of the NTR1-SSS/AAA mutant was reduced by 95%, the agonist-induced phosphorylation of the OTR-SSS/ AAA-1 and the OTR-SSS/AAA-2 mutants was each reduced by 95%, as compared with their wild-type counterparts. Therefore, the serine/threonine clusters responsible for βarrestin trafficking to endocytic vesicles are the principal sites of phosphorylation.

Example 7

Enhanced Arrestin Affinity Modified GPCR: MOR-V2R

Figure 12:
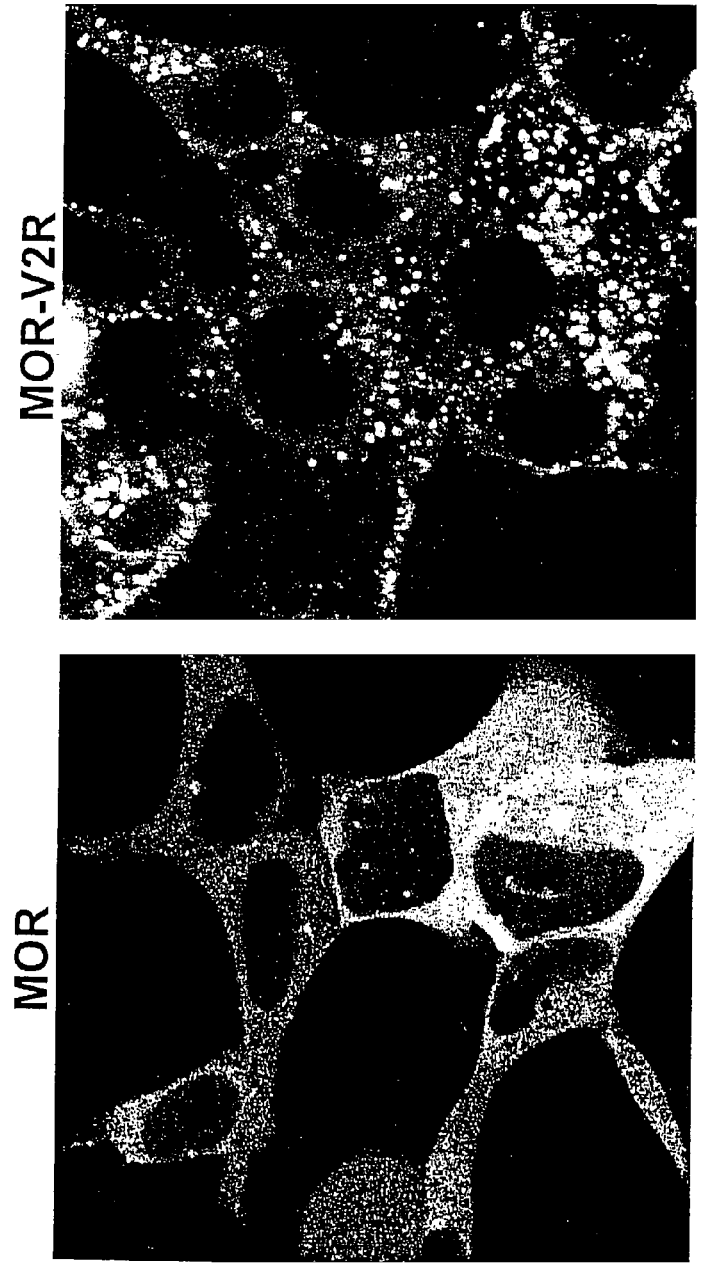
FIG. 12 shows the βarr2-GFP translocation to the MOR and MOR-V2R chimera in response to morphine.

The agonist activated mu opioid receptor (MOR), a class A GPCR, has very low affinity for βarrestins. βArrestin2-GFP will translocate to this receptor at the plasma membrane upon treatment with opioid agonists such as etorphine or DAMGO, but the extent of translocation is very weak and is difficult to detect (Zhang et al. 1999, Oakley et al. 2000). Moreover, no βarrestin translocation is observed to the MOR expressed in HEK-293 cells in response to the opioid agonist morphine unless GRKs are overexpressed (Zhang et al. 1999). To enhance the affinity of the agonist-activated MOR for βarrestin (and thereby enhance the detection of the agonist-activated MOR), we fused the first 351 amino acids of the MOR (Met-1 through Cys-351) to the 29 amino acid V2R carboxyl terminus. Cys-351 was chosen for the site of fusion because it properly positions the V2R serine cluster (SSS) within the modified receptor's carboxyl terminal tail (Oakley et al., 2001). When expressed, the MOR-V2R chimera contains the first 351 amino acids of the MOR (Met-1 through Cys-351), two Ala residues contributed by the Not I site, and the last 29 amino acids of the V2R carboxyl terminus (Ala-343 through Ser-371). The sequence of the MOR-V2R chimera is shown in FIG. 10A. In response to etorphine, DAMGO, or morphine, βarrestin2-GFP shows robust translocation to the MOR-V2R at the plasma membrane and profound internalization with the MOR-V2R into endocytic vesicles, as shown in FIG. 12. The ability of barrestin2-GFP to remain associated with the MOR-V2R chimera and traffic with it into endocytic vesicles markedly enhances the ability to detect receptor acitivity of the MOR.

Example 8

Enhanced Arrestin Affinity Modified GPCR: D1AR-V2R

Figure 13:
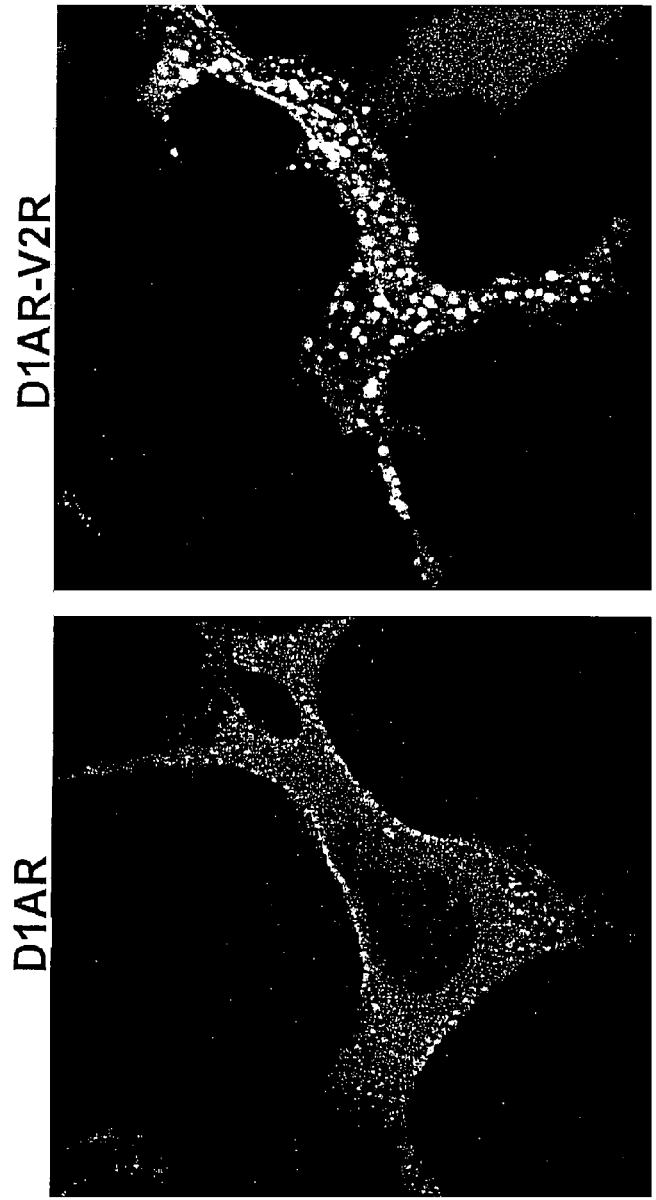
FIG. 13 shows the βarr2-GFP translocation to the D1AR and D1AR-V2R chimera in response to dopamine.

The agonist activated dopamine D1A receptor (D1AR), a class A GPCR, binds barrestin with low affinity. βArrestin2-GFP will translocate to this receptor at the plasma membrane upon treatment with dopamine, but the extent of translocation is weak (Oakley et al. 2000). To enhance the affinity of the agonist-activated D1AR for βarrestin (and thereby enhance the detection of the agonist-activated D1AR), we fused the first 351 amino acids of the D1AR (Met-1 through Cys-351) to the 29 amino acid V2R carboxyl terminus. Cys-351 was chosen for the site of fusion because it properly positions the V2R serine cluster (SSS) within the modified receptor's carboxyl terminal tail (Oakley et al., 2001). When expressed, the D1AR-V2R chimera contains the first 351 amino acids of the D1AR (Met-1 through Cys-351), two Ala residues contributed by the Not I site, and the last 29 amino acids of the V2R carboxyl terminus (Ala-343 through Ser-371). The sequence of the D1AR-V2R chimera is shown in FIG. 10B. In response to dopamine, βarrestin2-GFP shows robust translocation to the D1AR-V2R at the plasma membrane and profound internalization with the D1AR-V2R into endocytic vesicles, as shown in FIG. 13. The ability of βarrestin2-GFP to remain associated with the D1AR-V2R chimera and traffic with it into endocytic vesicles markedly enhances the ability to detect receptor acitivity of the D1AR.

Example 9

Enhanced Arrestin Affinity Modified GPCR: 5HT1AR-V2R

Figure 14:
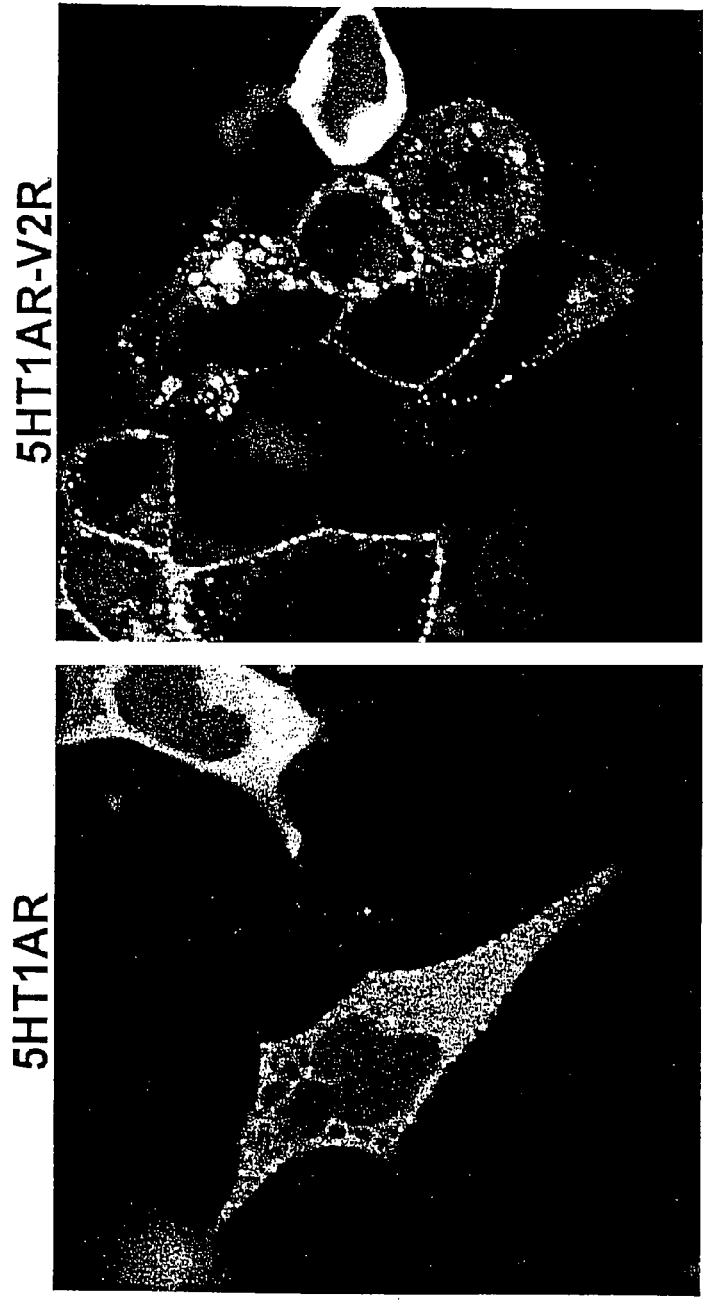
FIG. 14 shows the βarr2-GFP translocation to the 5HT1AR and 5HT1AR-V2R chimera in response to serotonin.

The agonist activated 5-hydroxytryptamine 1A receptor (5HT1AR, serotonin receptor), a class A GPCR, binds βarrestin with very low affinity. bArrestin2-GFP will translocate to this receptor at the plasma membrane upon treatment with serotonin, but the extent of translocation is very weak. To enhance the affinity of the agonist-activated 5HT1AR for βarrestin (and thereby enhance the detection of the agonist-activated 5HT1AR), we fused the first 420 amino acids of the 5HT1AR (Met-1 through Cys-420) to the 29 amino acid V2R carboxyl terminus. Cys-420 was chosen for the site of fusion because it properly positions the V2R serine cluster (SSS) within the modified receptor's carboxyl terminal tail (Oakley et al., 2001). When expressed, the 5HT1AR-V2R chimera contains the first 420 amino acids of the 5HT1AR (Met-1 through Cys-420), two Ala residues contributed by the Not I site, and the last 29 amino acids of the V2R carboxyl terminus (Ala-343 through Ser-371). The sequence of the 5HT1AR-V2R chimera is shown in FIG. 10C. In response to serotonin, βarrestin2-GFP shows robust translocation to the 5HT1AR-V2R at the plasma membrane and profound internalization with the 5HT1AR-V2R into endocytic vesicles, as shown in FIG. 14. The ability of βarrestin2-GFP to remain associated with the 5HT1AR-V2R chimera and traffic with it into endocytic vesicles markedly enhances the ability to detect receptor acitivity of the 5HT1AR.

Example 10

Enhanced Arrestin Affinity Modified GPCR: β3AR-V2R-V2R

The agonist activated β3-adrenergic receptor (β3AR) has been reported not to desensitize and not to bind βarrestin (Cao et al. 2000). bArrestin2-GFP does not translocate to this receptor at the plasma membrane upon treatment with isoproterenol or the selective β3AR agonist, CL316,243 (Cao et al. 2000). To enable the agonist-activated β3AR to be detected by the binding of barrestin, we fused the first 363 amino acids of the β3AR (Met-1 through Cys-363) to the 29 amino acid V2R carboxyl terminus. Cys-363 was chosen for the site of fusion because it properly positions the V2R serine cluster (SSS) within the modified receptor's carboxyl terminal tail (Oakley et al., 2001). When expressed, the β3AR-V2R chimera contains the first 363 amino acids of the β3AR (Met-1 through Cys-363), two Ala residues contributed by the Not I site, and the last 29 amino acids of the V2R carboxyl terminus (Ala-343 through Ser-371). The sequence of the β3AR-V2R chimera is shown in FIG. 10D. In response to isoproterenol, barrestin2-GFP shows robust translocation to the β3AR-V2R at the plasma membrane and profound internalization with the β3AR-V2R into endocytic vesicles, as shown in FIG. 15. The ability of barrestin2-GFP to bind the β3AR-V2R and traffic with it into endocytic vesicles provides an assay for detecting receptor activity of the β3AR.

Example 11

Enhanced Arrestin Affinity Modified GPCR: Edg1R-V2R

Figure 16:
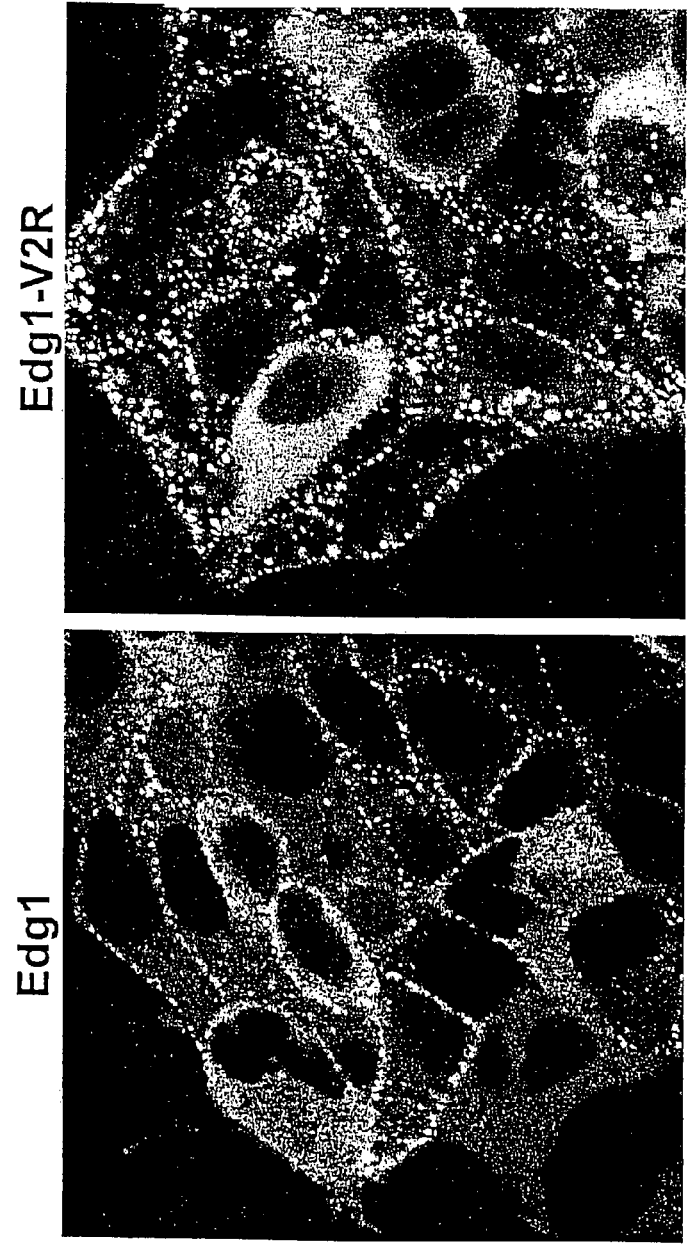
FIG. 16 shows the βarr2-GFP translocation to the Edg1 and Edg1-V2R chimera in response to sphingosine-1-phosphate.

The agonist activated endothelial differentiation, sphingolipid GPCR 1 (Edg1R), a class A GPCR, binds barrestin with low affinity. βArrestin2-GFP will translocate to this receptor at the plasma membrane upon treatment with sphingosine-1-phosphate, but the extent of translocation is weak. To enhance the affinity of the agonist-activated Edg1R for βarrestin (and thereby enhance the detection of the agonist-activated Edg1R), we fused the first 331 amino acids of the Edg1R (Met-1 through Cys-331) to the 29 amino acid V2R carboxyl terminus. Cys-331 was chosen for the site of fusion because it properly positions the V2R serine cluster (SSS) within the modified receptor's carboxyl terminal tail (Oakley et al., 2001). When expressed, the Edg1R-V2R chimera contains the first 331 amino acids of the Edg1R (Met-1 through Cys-331), two Ala residues contributed by the Not I site, and the last 29 amino acids of the V2R carboxyl terminus (Ala-343 through Ser-371). The sequence of the Edg1R-V2R chimera is shown in FIG. 10E. In response to sphingosine-1-phosphate, βarrestin2-GFP shows robust translocation to the Edg1R-V2R at the plasma membrane and profound internalization with the Edg1R-V2R into endocytic vesicles, as shown in FIG. 16. The ability of βarrestin2-GFP to remain associated with the Edg1R-V2R chimera and traffic with it into endocytic vesicles markedly enhances the ability to detect receptor activity of the Edg1R.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

Attramadal, H., Arriza, J. L., Aoki, C., Dawson, T. M., Codina, J., Kwatra, M. M., Snyder, S. H., Caron, M. G. & Lefkowitz, R. J. (1992) *J. Biol. Chem.* 267, 17882–17890

Oakley et al (2001) J. Biol. Chem. 276:19452–19460

Barak, L. S., Oakley, R. H., Laporte, S. A. and Caron, M. G. (2001) *Proc. Natl. Acad. Sci. USA* 98, 93–98

Barak, L. S., Warabi, K., Feng, X., Caron, M. G. & Kwatra, M. M. (1999) *J. Biol. Chem.* 274, 7565–7569

Barak, L. S., Ferguson, S. S., Zhang, J. & Caron, M. G. (1997) *J. Biol. Chem.* 272, 27497–27500

Barak, L. S., Ferguson, S. S., Zhang, J., Martenson, C., Meyer, T. & Caron, M. G. (1997) *Mol. Pharmacol.* 51, 177–184

Barak, L. S., Menard, L., Ferguson, S. S., Colapietro, A. M. & Caron, M. G. (1995) *Biochemistry* 34, 15407–15414

Ferguson, S. S., Barak, L. S., Zhang, J. & Caron, M. G. (1996) *Can. J. Physiol. Pharmacol.* 74, 1095–1110

Ferguson, S. S., Menard, L., Barak, L. S., Koch, W. J., Colapietro, A. M. & Caron, M. G. (1995) *J. Biol. Chem.* 270, 24782–24789

Kim, K.-M., Valenzano, K. J., Robinson, S. R., Yao, W. D., Barak, L. S., Caron, M. G. (2001) *J. Biol. Chem.* 276: 37409–37414

Laporte, S. A., Oakley, R. H., Holt, J. A., Barak, L. S. & Caron, M. G. (2000) *J. Biol. Chem.* 275, 23120–23126

Laporte, S. A., Oakley, R. H., Zhang, J., Holt, J. A., Ferguson, S. S., Caron, M. G. & Barak, L. S. (1999) *Proc. Natl. Acad. Sci. USA* 96, 3712–3717

Menard, L., Ferguson, S. S., Zhang, J., Lin, F. T., Lefkowitz, R. J., Caron, M. G. & Barak, L. S. (1997) *Mol. Pharmacol.* 51, 800–808

Mhaouty-Kodja, S., Barak, L. S., Scheer, A., Abuin, L., Diviani, D., Caron, M. G. & Cotecchia, S. (1999) *Mol. Pharmacol.* 55, 339–347

Oakley, R. H., Laporte, S. A., Holt, J. A., Barak, L. S., Caron, M. G. (2001). *J. Biol. Chem.* 276: 19452–19460

Oakley, R. H., Laporte, S. A., Holt, J. A., Caron, M. G. & Barak, L. S. (2000) *J. Biol. Chem.* 275, 17201–17210

Oakley, R. H., Laporte, S. A., Holt, J. A., Barak, L. S. & Caron, M. G. (1999) *J. Biol. Chem.* 274, 32248–32257

Zhang, J., Barak, L. S., Anborgh, P. H., Laporte, S. A., Caron, M. G. & Ferguson, S. S. (1999) *J. Biol. Chem.* 274, 10999–11006

Zhang, J., Barak, L. S., Winkler, K. E., Caron, M. G. & Ferguson, S. S. (1997) *J. Biol. Chem.* 272, 27005–27014

---

What is claimed is:

1. A method of screening compounds for GPCR activity comprising the steps of:
   (a) providing a cell that expresses at least one GPCR comprising an amino acid sequence of a first GPCR modified by substitution of a carboxyl terminal tail portion of the first GPCR with a carboxyl terminal tail portion from a different GPCR, the substitution located downstream of an NPXXY (SEQ ID NO:82) motif of the first GPCR, wherein the carboxyl terminal tail portion of the different GPCR comprises one or more clusters of phosphorylation sites, and wherein the GPCR further comprises a putative site of palmitoylation 10 to 25 amino acid residues downstream of the NPXXY motif (SEQ ID NO:82),
   wherein said cell further comprises arrestin conjugated to a detectable molecule;
   (b) exposing the cell to the compound;
   (c) detecting location of the arrestin within the cell;
   (d) comparing the location of the arrestin within the cell in the presence of the compound to the location of the arrestin within the cell in the absence of the compound; and
   (e) correlating a difference between (1) the location of the arrestin within the cell in the presence of the compound and (2) the presence of the location of the arrestin within the cell in the absence of the compound.

2. The method of claim 1, wherein the arrestin is detected in endosomes.

3. A kit for identifying a molecule that modulates the activity of a GPCR, comprising a cell that expresses at least one GPCR comprising an amino acid sequence of a first GPCR modified by substitution of a carboxyl terminal tail portion of the first GPCR with a carboxyl terminal tail portion from a different GPCR, the substitution located downstream of an NPXXY (SEQ ID NO:82) motif of the first GPCR, wherein the carboxyl terminal tail portion of the different GPCR comprises one or more clusters of phosphorylation sites, and wherein the GPCR further comprises a putative site of palmitoylation 10 to 25 amino acid residues downstream of the NPXXY motif (SEQ ID NO:82), wherein said cell further comprises arrestin conjugated to a detectable molecule.

\* \* \* \* \*